United States Patent [19]

Wolze

[11] Patent Number: 5,457,626
[45] Date of Patent: Oct. 10, 1995

[54] BIMODAL LIQUID CHROMATOGRAPHY PUMP EMPLOYING ARTIFICIAL INTELLIGENCE LOGIC FEEDBACK CONTROL

[75] Inventor: David A. Wolze, San Jose, Calif.

[73] Assignee: Dionex Corporation, Sunnyvale, Calif.

[21] Appl. No.: 299,988

[22] Filed: Sep. 1, 1994

[51] Int. Cl.[6] .......................... G06F 15/46; B01D 15/08
[52] U.S. Cl. ........................ 364/152; 364/166; 364/180; 210/198.2; 210/656
[58] Field of Search .................................. 364/148, 152, 364/160, 166, 180, 509, 510; 395/900, 906; 210/101, 198.2, 656, 657, 658; 417/43, 45

[56] References Cited

U.S. PATENT DOCUMENTS

| | | | |
|---|---|---|---|
| 4,775,481 | 10/1988 | Allington | 210/656 |
| 4,869,374 | 9/1989 | Allington. | |
| 4,986,919 | 1/1991 | Allington. | |
| 5,040,126 | 8/1991 | Allington | 364/510 |
| 5,076,761 | 12/1991 | Krohn et al. | 417/45 |
| 5,158,675 | 10/1992 | Allington et al. | 210/198.2 |
| 5,182,826 | 2/1993 | Thomas et al. | 417/44 |
| 5,234,587 | 8/1993 | Allington | 210/198.2 |

Primary Examiner—Roy N. Envall, Jr.
Assistant Examiner—Thomas E. Brown
Attorney, Agent, or Firm—Flehr, Hohbach, Test Albritton & Herbert

[57] ABSTRACT

Flowrate in a precision pump used for liquid chromatography employs a digital control system incorporating artificial intelligence. The pump system operates in a default flow mode, wherein real-time pressure feedback is not used to control motor speed, or in pressure mode, wherein motor speed is controlled by the pump system pressure point. The artificial intelligence commands mode changes to pressure mode when the constant displacement flow measurement time is within a threshold relative to commanded flowrate, and when the higher pressure piston is being measured. Flow mode pressure ripple is minimized by monitoring pressure points and commanding motor speed change at appropriate positions during the motor cam rotation. Pressure mode uses the higher pressurized piston as a reference for constant displacement flow measurement and provides accurate flowrate even if one piston is leaky. In pressure mode, the artificial intelligence monitors for intake cycle oscillation and optimizes a highest system pressure gain dynamically. By determining the duration of hydraulic intake and activating proportioning only during the constant intake flow portion of an intake cycle, constant flowrate proportioning is provided. The present invention compensates for a variety of system and environmental variables including leaky valves, air bubbles, a leaky cylinder head, pressure changes, and variations in anticipated compliance and can maintain a flowrate constant within about ±1% without using real-time pressure feedback.

9 Claims, 7 Drawing Sheets

BIMODAL LIQUID CHROMATOGRAPHY PUMP EMPLOYING ARTIFICIAL INTELLIGENCE LOGIC FEEDBACK CONTROL

FIELD OF THE INVENTION

This invention relates to precision control of flowrate and accurate proportioning of solvents in an analytical procedure, and more specifically to flowrate control in liquid chromatography analysis.

BACKGROUND OF THE INVENTION

Many applications require the controlled mixing and/or delivery of fluid eluents, liquid chromatography ("LC") for example. In LC, a flowing stream of liquid solvent in a mobile phase carries a liquid sample containing components to be analyzed. A precision pump mechanism causes the liquid solvent to pass through a chromatography column typically packed with ion exchange particles in a stationary phase. While passing through the column, components within the liquid sample are differentially adsorbed and desorbed from the stationary phase. These individual components then elute from the column at different times and are separately detected and quantified as they flow through a detector. In this fashion, analytical information is provided as to the constituents present in the liquid sample.

Even more effective separations result from high performance liquid chromatography systems ("HPLC"), wherein mixtures of solvents are used as the mobile phase. When the components of the mixture are held constant, an isocratic mode results. By contrast, gradient chromatography results when the composition of the liquid changes over time while being pumped to the column, for example, a composition going from 100% water to 100%, methanol.

FIG. 1 depicts a generic liquid chromatography system that may be operated in an HPLC mode, wherein differential analysis may be provided It is the purpose of precision pump mechanism 10 to deliver a liquid solvent via an output port 12 at a constant flowrate to a column 14 or other downstream analytical apparatus. In the HPLC mode, there are at least two sources of liquid input, 16A, 16B, each of which may contain different constituents.

In FIG. 1, liquid input sources 16A, 16B are coupled to a proportioning valve 17 whose operation is controlled by the digital control system 28. Through a "T-connector", valve 17 outputs liquid to inlet check valves 32A and 32B. Of course in non-differential analysis, there is a single liquid input source, e.g., 16A or 16B.

In FIG. 1, a rotary motor mechanism 18 receives an input voltage from a driver amplifier 20, and outputs rotary shaft motion in response to the input voltage. A tachometer mechanism 22 senses the rotary speed of the motor mechanism shaft 24 and provides this information as an input to the driver amplifier 20 in a closed feedback loop configuration.

As is known in the art, affixed to motor shaft 24 is a disk 26A that contains precisely located slots through which light may pass and be sensed by a sensor unit 26B that typically includes light emitting diode and detector pairs. At the motor shaft 24 rotates with speed ω, the light sensors detect a digital pattern of light and no-light, which information is coupled to a digital control system 28. Other precision mechanisms for detecting rotary shaft speed and position could of course be used.

Digital control system 28 contains a control panel (not shown) permitting an operator to set a desired liquid flowrate at the output port 12. The output control signal from digital control system 28 is then provided as an additional input to the driver amplifier 20.

A mechanism 30 translates the rotary motion of shaft 24 to a reciprocating back-and-forth motion that is mechanically coupled to at least two piston heads (or "ends") 34A, 34B associated with surrounding cylinders (not shown). Where, as shown, two piston heads are used, they reciprocate 180° out of phase. One piston intakes liquid while the other piston exhausts or outputs liquid, the intake cycle being shorter than the exhaust cycle. This two piston configuration uses a point of cross-over during which both pistons are pumping simultaneously so as to maintain system pressure without a dead zone. In this pressure mode of operation, to maintain constant system pressure and therefore constant flowrate at cross-over requires approximately halving motor speed. At cross-over, one piston is ending its exhaust cycle while the remaining piston is commencing its exhaust cycle. However, the prior art cannot accurately predict when during the system cycle motor speed should be halved to avoid significant pressure fluctuations.

In non-precision, non-proportioning applications a single reciprocating end may be used. In contrast to parallel-coupled 180° out-of-phase ends, it is also known in the art to use a single motor that operates two series-coupled lead-screw heads to pump eluent to a column.

In response to the reciprocating motion provided by mechanism 30, ends 34A, 34B cause liquid from the respective liquid inputs 16A, 16B, after passing through respective unidirectional intake and exhaust check valves 32A, 32B, and 36A, 36B to be mixed at a "T"-connector proportioning valve 38. The thus-mixed liquids pass through a pressure transducer 40, through output port 12 and to the first stage of the downstream analytical apparatus, e.g., liquid chromatography column 14. As shown in FIG. 1, the output pressure measured by transducer 40 is coupled as an input to the digital control system 28 in an attempt to regulate the flowrate of the liquid exiting output port 12. Total flowrate is indirectly derived from the measured output pressure.

The real time use of output pressure data from transducer 40 to control flowrate in pump 10 is termed a pressure mode of operation. Pressure mode operation minimizes pressure ripple, and is advantageous for ion detection by conductivity or other detector. Such detection is relatively sensitive to pressure variations. However, pressure mode operation is disadvantageous where viscosity changes rapidly, or where other dynamic conditions are presented (e.g., column switching, injection, high speed operation). In the presence of such dynamically changing conditions, the lagging behind of feedback information precludes pump 10 from responding with sufficient speed to achieve the correction.

Under certain steady state conditions with normal pump speeds, even prior art pressure feedback can reduce pressure ripple effectively. However, under dynamic conditions, due to viscosity changes, high speed operation, or rapid change in system parameters as in switching columns or during an injection, the present invention reduces cross-over ripple, whereas prior art techniques cannot.

Unfortunately, prior art pump 10 cannot operate in a flow mode, wherein output flowrate is regulated without making real time use of output pressure data. Were it possible, a flow mode operation would provide superior flowrate performance in the presence of rapidly changing viscosity gradients.

The analysis application and the flowrate at output port 12 determine the liquid pressure. In practice, standard bore piston heads or ends 34A, 34B operate at 1 piston stroke every six second, which delivers approximately 1 ml/minute, whereas so-called microbore pistons deliver approximately 250 μl/minute operating at the same piston stroke rate. Pressure at outlet port 12 is typically in the range 300 psi to 5,000 psi and is determined substantially by the column 14 or other apparatus downstream from the outlet port 12 of the pump 10.

In liquid chromatography, a detector (not shown) detects separated components in the eluent (solvent) passing through column 14 by outputting a peak signal. These signal peaks are then integrated as a function of time to arrive at meaningful analytical information. It is therefore important that the flowrate of the liquid at output port 12 and passing through the column 14 be a constant.

Unfortunately, prior art pump systems such as shown in FIG. 1 cannot reliably maintain a desired flowrate within an acceptable tolerance. For example, a leaky valve or piston seal will cause the pump 10 to output at less than the desired flowrate commanded by digital control system 28. Even if the valves and seals are not leaky, output flowrate can vary due to a differential change in compliance, e.g., variations in material expansion under pressure.

Further, production variations in manufacturing tolerances associated with cylinder heads, plastic or stainless steel fluid-carrying tubing, valves and other components can cause undesired deviations in the output flowrate, as can the presence of a bubble within the fluid flow path within pump 10. For example, a piston head attempting to compress liquid might in fact be compressing an air bubble, with the result that less liquid is pumped, with an attendant drop in output flowrate at port 12. Prior art control systems do not recognize such conditions, cannot distinguish between the output of each piston head, and cannot, for example, cause the higher pressure-delivering piston head to compensate for the remaining, lower-pressure, piston head.

In addition, the compliance (e.g., expandability) of the tubing, piston seals, and components comprising pump 10 may change with time, or material changes may be made, such as substituting stainless steel tubing for plastic tubing. If for whatever reason fluid-coupling components within pump 10 expand, the flowrate at outlet port 12 will be less than what digital control system 28 (and the system operator) believe to be present. Further, ambient environmental pressure or temperature, as well as changes in the liquid viscosity or compressibility can alter the output flowrate. Maintaining a constant output flowrate during chromatography using a gradient eluent is especially challenging because viscosity of the liquid mixture can rapidly vary by a factor of three.

A persistent problem in attempting to run with eluents of rapidly changing gradients is that in a conventional pressure mode system, there will always be several motor revolution cycles lagging of the necessary corrective action, while viscosity continues to change. Also, as viscosity changes, the inherent system pressure changes and the prior pressure control system undesirably changes flowrate (e.g., motor speed) to compensate for the change in pressure. Further, the prior art's reliance upon pressure parameters alone has a deleterious effect as pressure and flowrate tend to counter each other when attempting to make adjustments.

Thus, prior art systems cannot control flowrate to better than about 10% to 15% during rapid gradient change, although the error will be consistent for repeated runs. Thus, because of its relative consistency, the prior art can compensate for flowrate variation in repeated runs. Alternatively, a syringe-type lead screw system capable of only a single flowrate will be employed in the prior art during fast gradient analyses.

To recapitulate, existing pump systems operate in pressure mode, and cannot adequately compensate for variations in equipment, viscosity, pressure, compliance, temperature, the presence of air bubbles, and other variables likely to be experienced. Such systems measure and make real time use of total pressure indirectly derive flowrate. However, the total pressure under measurement will reflect leakage flow components, compliance-variable components, in addition to the actual eluent fluid flow. Simply stated, the prior art cannot distinguish or even recognize the various error components that contribute to undesired variations in output flowrate.

Thus, there is a need for a control mechanism that can control output flowrate in a precision pump despite the presence of variables including a leaky valve, an air bubble, a leaky cylinder head, variations in pressure, and compliance variations. Preferably such mechanism should permit pump system operation in flow mode, in pressure mode, and in an intelligent combination of each mode.

Such mechanism should provide acceptable flowrate control even if only one piston head is operating according to specification, wherein the correctly operating piston head compensates for the remaining piston head. In addition, such mechanism should maintain a pressure characteristic substantially free of peaks or dips over the approximate range 300 psi to 5,000 psi.

Further, such mechanism should provide experimenters with a constant fluid sample characteristic that is independent of system variables such as compliance, system fabrication tolerances, and ambient environmental changes, including transient changes. Such mechanism should reduce cross-over pressure ripple despite dynamic flow conditions, and should control flowrate even during a rapidly changing viscosity gradient experiment to within about ±5% or better.

The present invention provides such a control mechanism.

SUMMARY OF THE PRESENT INVENTION

The present invention provides a precision pump used for liquid chromatography and the like with bimodal operation, flow mode and pressure mode. In flow mode, a constant flowrate is maintained by operating the motor at a chosen one of two speeds without using real-time pressure feedback. As such, flow mode is especially advantageous for pressure-sensitive runs, e.g., those involving varying viscosity. In pressure mode, a constant flowrate is maintained by continuously adjusting motor speed in response to real-time pressure data. As such, pressure mode is advantageous for experiments dictating minimum pressure ripple.

The present invention regulates flowrate in such a pump system by providing a digital control system that incorporates artificial intelligence to regulate the pump motor speed.

In a first aspect, the pump system can operate bimodally, in a flow mode or in a pressure mode. The system user can manually select the mode of operation, and the pump system can automatically switch between modes as required to maintain constant flowrate. In the default flow mode, pump motor operates at a constant speed without using real-time pressure feedback data to control motor speed. This is in stark contrast to the prior art.

Flow mode is implemented by a fuzzy logic routine controlling the digital control system, wherein pressure ripple is minimized by precisely varying the rotational speed of the pump motor between one of two speeds. By monitoring output pressure and encoder disk-derived motor position, applicant's algorithm predicts when the motor speed should be increased or decreased during motor driven cam rotation. Decreasing motor speed (preferably by 50%) during piston overlap relative to the speed during piston intake stroke results in a substantially constant flowrate. Because real-time output pressure data is not used to control flowrate, flow mode is especially useful in experimental runs wherein sudden viscosity changes or gradients occur in the liquid being pumped.

When the user selects pressure mode, the pump system automatically changes from the default flow mode to pressure mode when three conditions are met. These conditions are that motor speed is within a preferably 3% threshold of the commanded flowrate, the piston being measured is at a higher pressure than the remaining piston, and two cam cycles have elapsed. In entering pressure mode, the higher pressurized piston will now be used as the reference piston for monitoring system pressure. By contrast, in the prior art the monitored piston is arbitrarily selected without regard to piston pressure. Motor' speed is measured by angular displacement on an encoder disk mounted on the motor shaft. This measurement occurs during a constant displacement portion of the pump cycle wherein one piston is pressurized and operating in steady-state.

Pressure mode uses the higher pressurized piston as a reference for constant displacement flow measurement, with the operating pressure set point updated every other piston cycle. In this manner, flowrate is accurately controlled even when the system includes a leaky piston. In pressure mode, if flow rate deviates by more than a desired tolerance, the control system automatically returns the pump system to default flow mode. Reinitialization then occurs, and after two cycles if the desired flowrate regime is again attained, pressure mode is re-entered.

In yet another aspect, the artificial intelligence functions in pressure mode to determine the optimum highest system pressure gain, independently of piston head type or system application. During intake, pressure is monitored for the presence of oscillation. If oscillation is detected, pressure gain is decremented until a highest stable pressure gain is reached. This ability to dynamically adjust pressure gain on the fly advantageously permits changing-from microbore to standard bore operation, as well as compensating for system variables including compliance.

In this manner, flowrate is controlled during flow mode operation, which is commonly used for analysis involving rapidly changing eluent viscosity or gradients, or other varying system parameters. However, flowrate is also controlled for pressure mode operation, a mode wherein pressure ripple is especially minimized. Pressure mode is commonly used for chromatography runs that use detectors that are highly sensitive to pressure variations, e.g., ion chromatography with suppressed conductivity suppression detection, or HPLC with amperometry detection.

In either mode, the present invention can compensate for a variety of system and environmental variables including leaky valves, air bubbles, a leaky cylinder head, pressure changes, and variations in anticipated compliance. In either mode, a flowrate can be established and maintained within about ±1%, even when one of the pistons is leaky.

In a third aspect, the present invention determines the onset and duration of hydraulic intake and permits proportioning during the constant intake flow portion of an intake cycle. In this fashion, proportioning occurs with constant flowrate over a wide pressure regime, thus providing a more accurately mixed output eluent.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 2A:
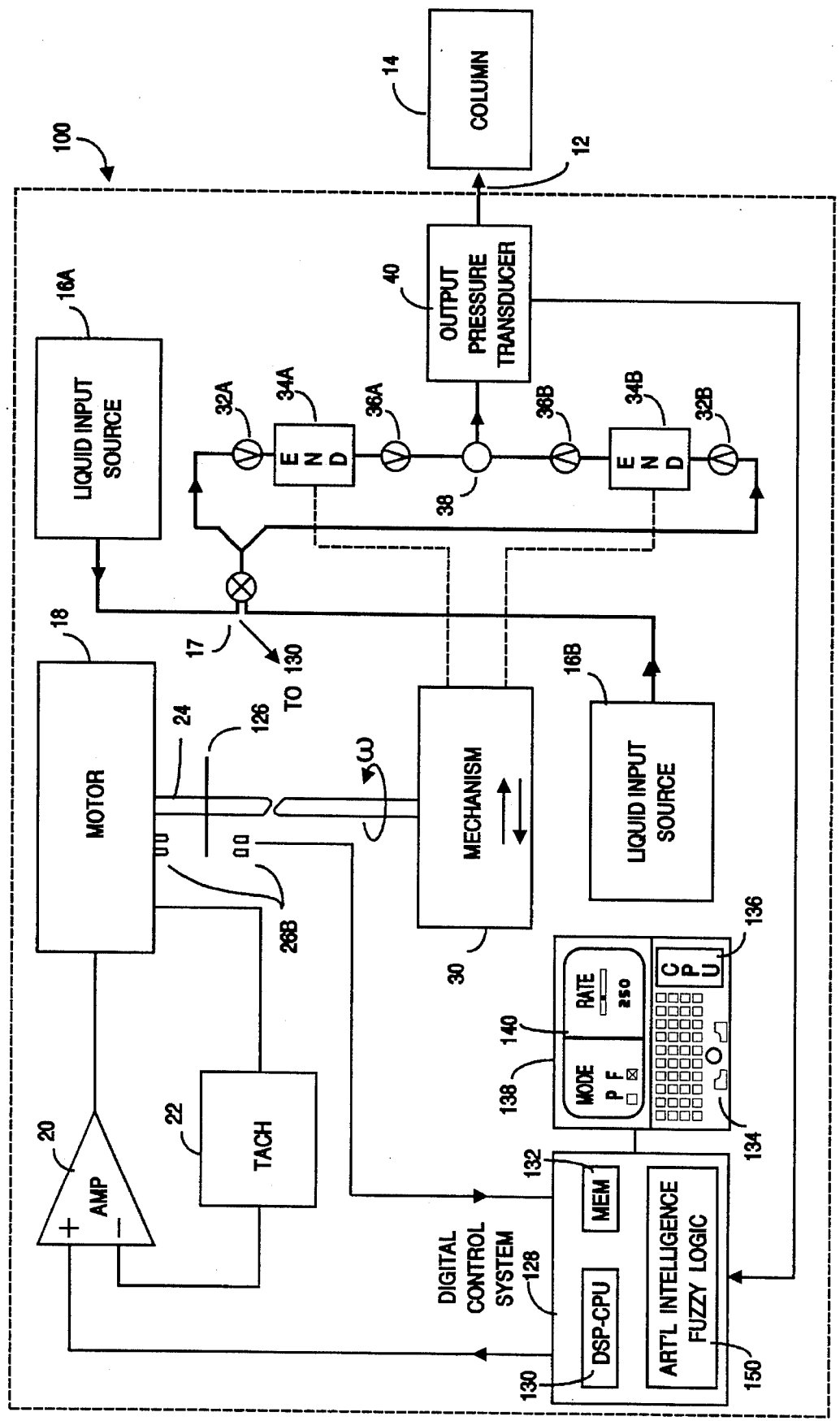
FIG. 2A depicts a fuzzy-logic digitally controlled precision pump suitable for liquid chromatography, according to the present invention.
Figure 2B:
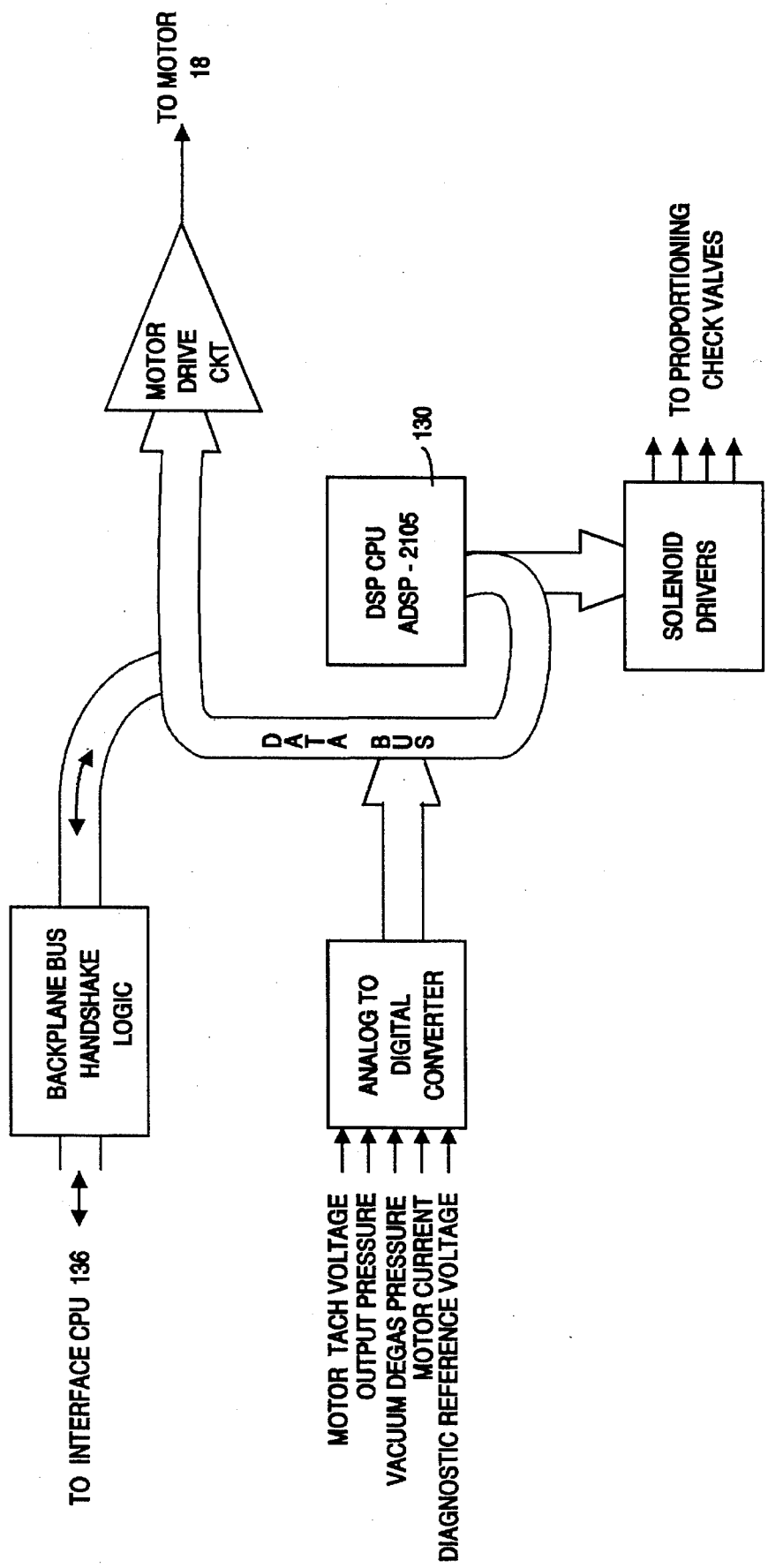
FIG. 2B is a block diagram showing information flow to the digital signal processing CPU, according to the present invention.

The present invention is shown in FIG. 2A as a digital control system 128 including an artificial intelligence or fuzzy logic unit 150 and control unit 138. FIG. 2A. FIG. 2B is a more detailed block diagram showing implementation within digital control system 128.

Figure 1:
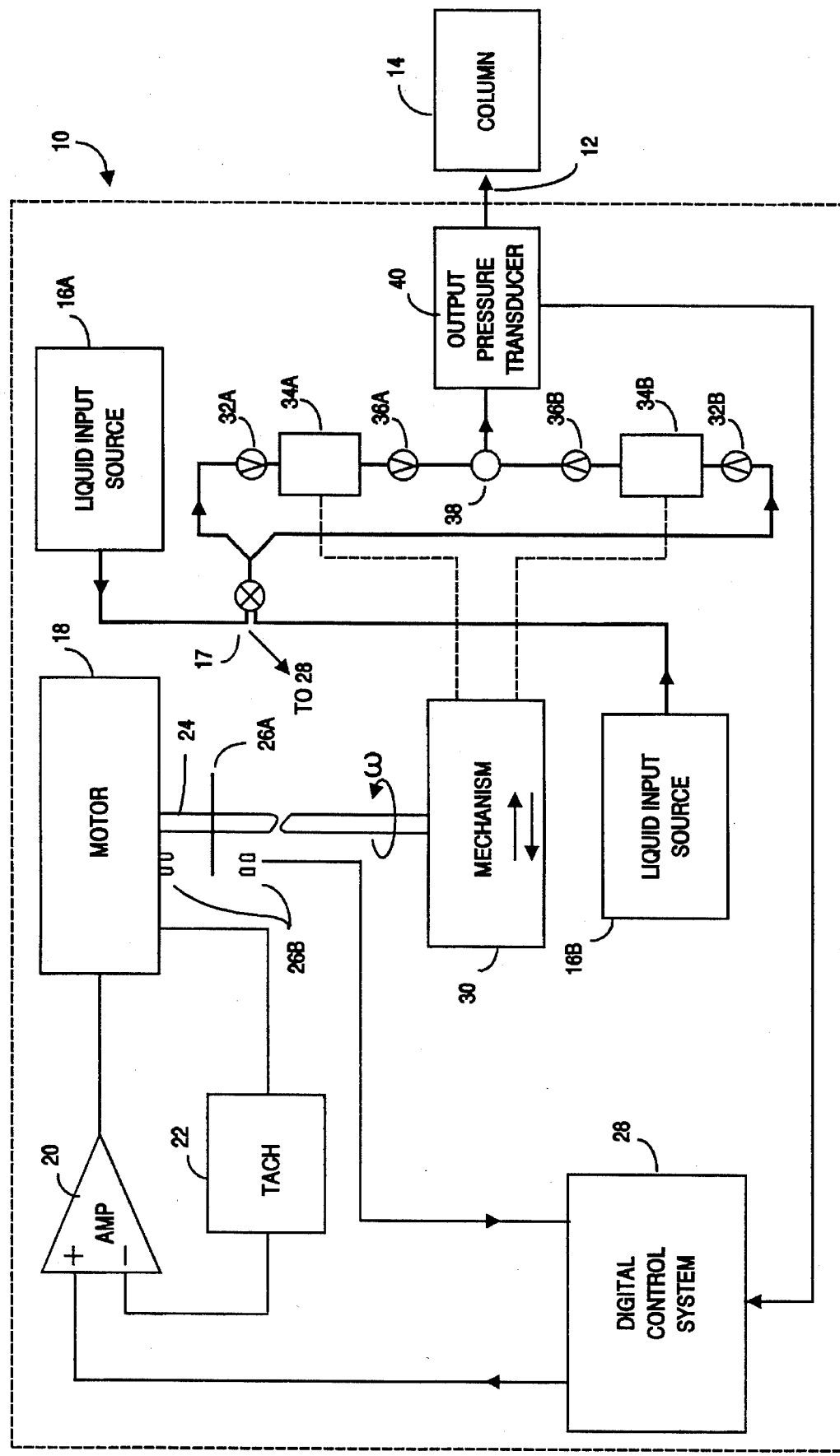
FIG. 1 depicts a digitally controlled precision pump suitable for liquid chromatography, according to the prior art.

In FIG. 2A, like element reference numerals refer to components that can be identical to what was described with respect to the prior art pump system 10 shown in FIG. 1. In FIG. 2A, a pump system 100 includes a digital control system 128 with a digital signal processor central processing unit ("CPU") 130, a set of algorithms comprising artificial intelligence or fuzzy logic 150, attendant memory 132, an interface CPU 136 located within a control panel unit 138 that includes operator usable keys, trackball and other input devices 134, and a monitor 140. In the preferred embodiment, monitor 140 can present a Windows™ or similar format menu permitting the system user to change pump parameters and to monitor pump performance.

Using a monitor displayed menu or a mechanical switch, system 128 permits the system user to select whether pump system 100 should operate in a flow mode or in a pressure mode, and to command the desired flowrate through output port 12. These commands may be issued using the input devices 134. If desired, system 128, control panel 134 and display 136 may include a personal computer or a work station unit, wherein the algorithms implementing artificial intelligence 150 may be loaded or stored.

With reference to FIG. 2A, DSP CPU 130 preferably is an Analog Devices embedded digital signal processing unit number ASDP 2105 that communicates with other portions of digital control system 128 through a parallel bus. Analog system input signals such as a tachometer voltage from tach 22, output pressure from transducer 40, motor current from motor 18 are digitized by an analog-to-digital converter and presented to the parallel data bus. Also presented are an optional vacuum degas pressure that allows system 100 to degas the input fluids before a run. A 1.00 V reference voltage is also presented for diagnostic purposes.

In FIG. 2B, signals to and from the interface CPU 136 travel by bus and a backplane bus. Various signals are bus-coupled to the motor drive circuit, shown generically in FIG. 2A as amplifier driver 20, which outputs a signal that determines the rotational speed ω of motor 18. Other signals from DSP CPU 130 are coupled out to solenoid drivers that can electrically operation the various check valves shown in FIG. 2A.

In the preferred embodiment, interface CPU 136 is an Intel 80186 single board computer unit used primarily to handle user input and user display tasks. The architecture and use of DSP CPU 130 and interface CPU 136 (or equivalent components) are well known in the art. Motor 18 preferably is a Yasgowa model Minertia gear motor, with a ±12 V control input voltage range, although other motors may be used instead. In the preferred embodiment, applicant's artificial intelligence (see APPENDIX 1) comprises 1,000 words each comprising 24 bits or 3 bytes. The algorithm is stored in 3 KB of flash memory associated with the interface CPU 136. The algorithm could, however, be stored in the digital control system 128, or stored elsewhere.

Figure 3:
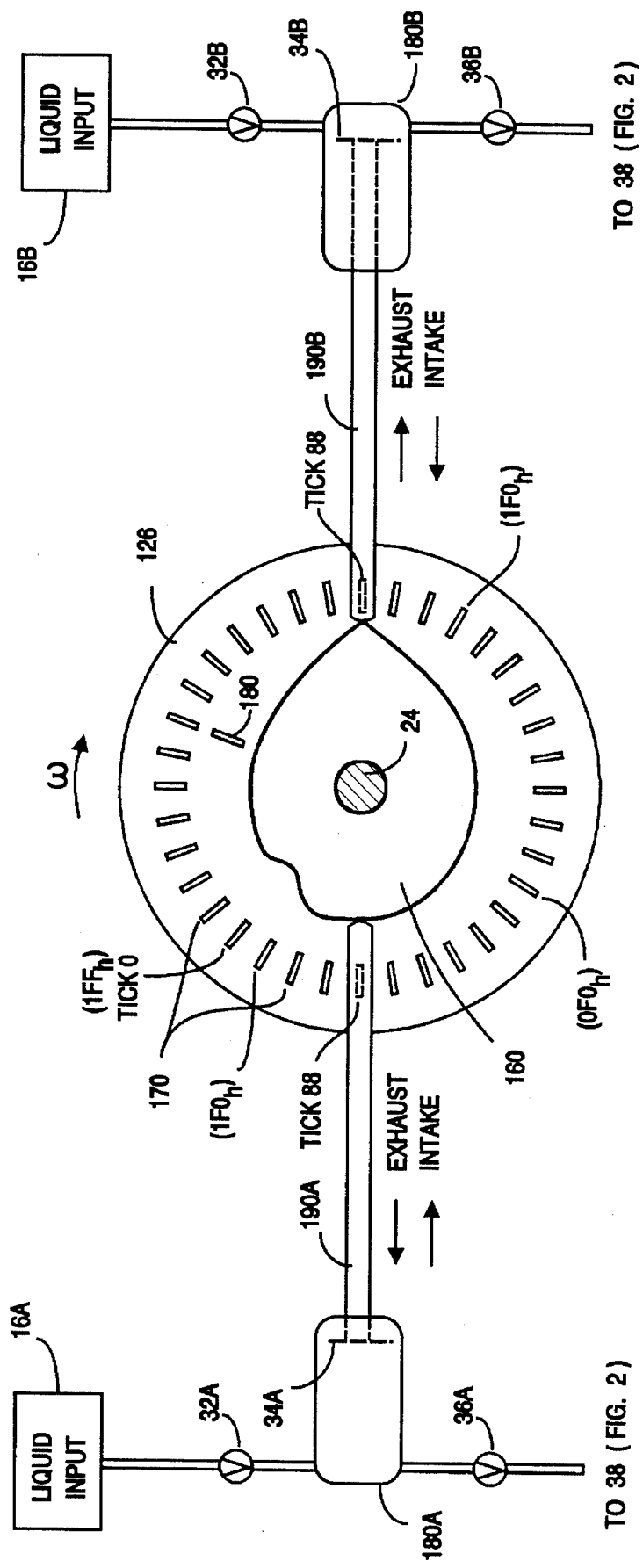
FIG. 3 schematically depicts a cam mechanism used to generate reference tick counts for use with the present invention.

As shown by FIG. 2A, one input to the digital control system 128 is the output from a high resolution incremental encoder disk 126 (to be described further with respect to FIG. 3). As best seen in FIG. 3, the encoder disk 126 is mounted to the shaft of motor 18, as is a cam 160.

Among the many advantages provided by the present invention is that the rotational speed of motor 18 may be precisely regulated over a range of about 256:1, and that this range may be changed by changing the pistons and cylinders to a different size (e.g., standard bore of 100 μl/cylinder displacement, and microbore of 25 μl/cylinder displacement). The ability to change cylinders will permit a standard bore system flowrate of 0.04 ml/minute to 10 ml/minute, and a microbore flowrate of 0.01 ml/minute to 2.5 ml/minute.

In the preferred embodiment shown in FIG. 2A, mechanism 30 employs a cam 160 (described more fully with respect to FIG. 3), to translate rotational motor action to reciprocating motion that drives first and second cylinder piston heads or ends 34A, 34B. However, the present invention may also be practiced where motor 18 drives a mechanism 30 that includes a pair of lead screw mechanisms.

Those skilled in the art will appreciate that such lead screw mechanisms would receive liquid through valves 32A, 32B and deliver the pumped liquid through outlet valves 36A, 36B, a "T"-connector proportioning valve 38, through a pressure transducer 40 to the column or other load 14. It is also understood that the various valves shown in FIGS. 2A and 3 preferably are solenoids operating under control of digital control system 120. Because lead screw mechanisms are well known in the art, no further description of their use with the present invention will be given.

As shown in FIG. 2A, pump system 100 also uses a pressure transducer 40 to monitor pressure at the pump output port 12, which pressure data is used by digital control system 128 to rapidly derive flowrate on a short term basis. A pressure transducer is because inexpensive real time basis flowrate measurement devices do not exist for the low flowrate regimes used in liquid chromatography at not available. Further, because pump system 100 may operate at pressures exceeding 5,000 psi, transducer 40 provides a mechanism for monitoring the safety of the equipment being used, and can also provides meaningful data concerning pressure leaks to digital control system 120.

With reference to FIG. 3, a high resolution incremental encoder disk 26A' is firmly locked to a cam 160 and the shaft 34 of rotary mechanism 18. Cam 160 is associated with a suitable mechanism 30 for translating rotational to reciprocal motion.

Figure 6A:
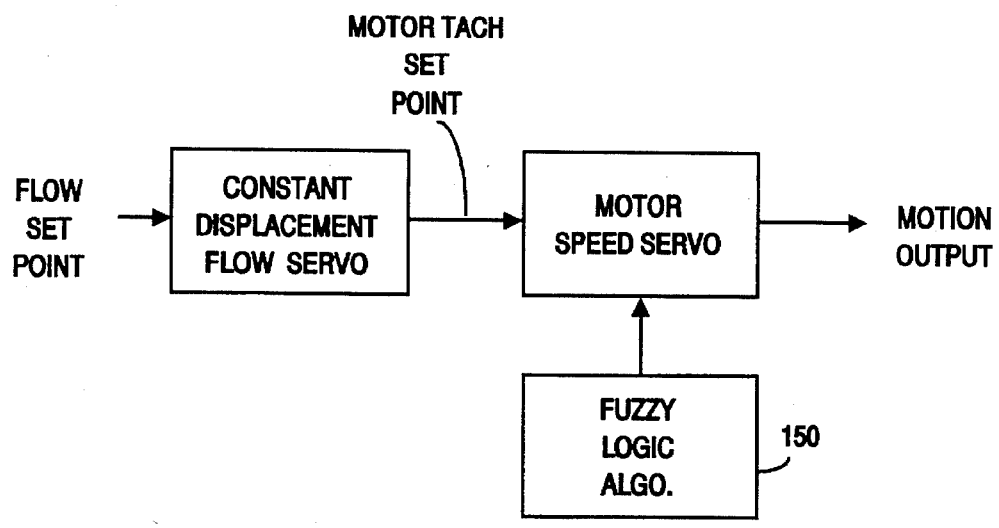
FIG. 6A is a block diagram showing the two feedback stage implementation of flow mode, according to the present invention.
Figure 6B:
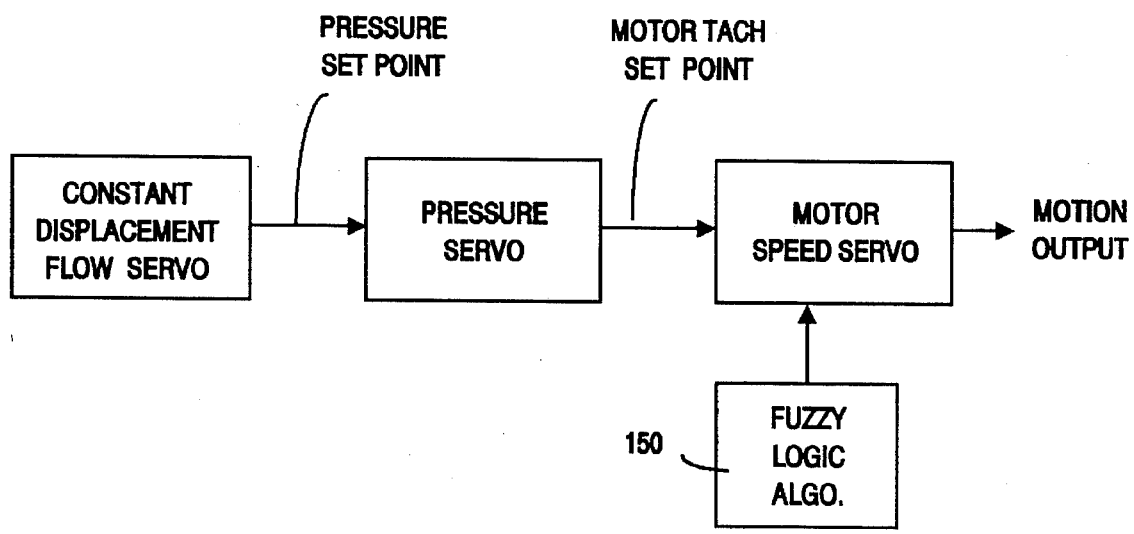
FIG. 6B is a block diagram showing the three feedback stage implementation of pressure mode, according to the present invention.

In pressure mode, the present invention derives flowrate from a constant displacement flow measurement, and adjusts the system by changing the pressure set point once per cam revolution in a sampled feedback configuration (see FIG. 6B). The pressure set point is the pressure at which pump system 100 is operating.

In flow mode, the present invention derives flowrate from a similar constant displacement flow measurement, and adjusts the system by changing the motor speed set point twice per cam revolution (see FIG. 6A).

In FIG. 3, cam 160 is shown at a cross-over point for piston head 34B, which is at the end of the exhaust stroke for piston 34B and beginning of its intake stroke. Because the cam is not symmetrical, piston 34A will also remain in the exhaust portion of its cycle before commencing its intake stroke.

Thus, FIG. 3 depicts an overlap condition, wherein both piston heads have simultaneously moved outward in an exhaust stroke. Some overlap is necessary to prevent a pressure decrease during the intake stroke of any given piston and there is a concomitant decrease in motor speed to provide constant pressure. It will be appreciated that pump system 100 is at any time in either an intake regime or an overlap regime, which in the preferred embodiment represent, respectively, 151° and 29° of cam rotation. The exhaust stroke represents 180° plus 29°, or 209° and is not descriptive of a unique event.

If pressure is examined during overlap, a slight increase or decrease in pressure is observed, depending upon the extent and timing of the overlap. The prior art attempts to design a pump system 10 with sufficient overlap that, at maximum pressure (e.g., perhaps 5,000 psi), there will be almost perfect cancellation in pressure with only a small pressure or flowrate ripple exhibited. But at lower pressures, a pressure peak is present at overlap, which must be compensated for by the control system. Alternatively, some prior art designs are optimized for a nominal pressure, above which there will be a pressure dip and below which there will be a pressure peak at overlap. However the compromises, prior art pump systems exhibit pressure peaks or dips during experiments, with result noise and poor performance. Unfortunately, no prior art systems can maintain a pressure characteristic free of peaks or dips over the range 300 psi to 5,000 psi.

With further reference to FIG. 3, the cross-over point of piston 34B does not represent a stable time for digital control system 128 to sample system parameters as the piston pressure and motor speed are changing. By contrast, stable data is sampled when one of the pistons is halfway through its exhaust stroke, whereat the piston will be fully pressurized, pressure and motor speed will be constant, and fluid will flow linearly.

APPENDIX 1, attached, is a computer printout in assembly language code of applicant's fuzzy logic algorithm 150 for digital control system 128. With respect to APPENDIX 1, pages 39–42 contain code setting up procedures used for applicant's flow mode (see page 42 therein), and pressure mode (see page 42 therein, continuing to page 43). At APPENDIX 1, pages 39–43, code implementing applicant's positive displacement flow control is set forth, which code is used in both flow mode and pressure mode operation.

The present invention measures the time for the last fourth of the intake cycle, wherein pressure and motor speed are stable, to indirectly determine flowrate. If control system 128 is set for one motor stroke every six seconds, the cam should require 1.50 seconds to traverse one-fourth the stroke. Assume that the cam took X% too long for the quarter stoke. In pressure mode, control system 128 will increase the pressure set point by the same X% to compensate during the next cam revolution. However in flow mode, control system 128 will increase the motor speed set point by the same X% to compensate during next piston stroke. In this fashion, the pressure set point is directly altered once per cam revolution in pressure mode, or once per piston stroke in flow mode, as needed, to indirectly alter motor speed in a sampled feedback configuration.

In pressure mode, the size of the constant displacement angle preferably small, e.g., less than 45°. But in flow mode, the pressure feedback cannot compensate for system compliance, resulting in a longer term effect. Thus, the constant displacement measurement angle preferably is wider to cover almost the entire intake stroke. This permits adequately accounting for the compliance. A good comprise for operating in both pressure and flow mode was found to be about 135°, e.g., from 070 hex to 1F0 hex.

As shown in FIG. 3, disk 26A' carries a ring of 1024 precisely defined, equi-spaced slots 170 that will define a first information channel (channel A), and also carries a single index slot 180 defining a second information channel, channel B. While a number different than 1024 may be used, 1024 slots provides adequate resolution to control pump 150 both in LC and HPLC modes of operation. These slots are used with two light emitting detector ("LED") and sensor pairs 26B to communicate to applicant's fuzzy logic module 150 the absolute position of the motor rotary shaft 24, and thus the absolute position of cam 160.

With reference to APPENDIX 1, page 34, in a manner known to those skilled in the art of digital circuit design, the detected light from the first information channel is coupled to up- and/or down-counters that may be reset with the output from the detected light from the second information channel. In FIG. 3, the "0" reference position is denoted as "TIC 0" and within the digital control system 128 is identified as hex-based count $1F0_h$.

In FIG. 3, head 34A and 34B are respectively coupled to piston shafts 190A, 190B whose distal ends include rollers (not shown) that contact the perimeter of the rotating cam 160. Piston head 34B, shown within cylinder 180B, is shown in a position terminating its exhaust cycle and beginning its intake cycle. Conversely, since it is 180° out of phase, piston head 34A, operating within cylinder 180A, is terminating its intake cycle and commencing its exhaust cycle. As is common in the art, a minimum of two heads are used in precision applications to ensure there is no dead zone with respect to refilling the cylinders with fluid during the intake/exhaust strokes. While the present invention will function with more than two heads, doing so adds to the cost of the overall pump system.

As shown in APPENDIX 1, page 34, part of the code defines index 180 and correlate its location relative to the cam 160, permitting determination of the point whereat a piston crosses on a trough as cam 160 rotates. The point where a piston crosses, at the end of the intake stroke, will be deemed "0", as shown by "TICK 0" on FIG. 3, which point will also be the start of overlap in that both heads will then move outward.

In the present invention, an edge-sensing down counter is set to the cam encoder offset, which is a number of counts (or "TICKS") from the encoder index slot 180 to the zero point on the cam mechanism 160. This offset is set to the cam encounter alignment factor value, e.g., to 180, which is the number of ticks from the index to the point where cross-over begins. When the down counter decrements to 0, it sets a second tick-synchronized counter to 0, from which the second counter increments with each tick. As reflected by APPENDIX 1, only the first nine bits are read on the second (up) counter, but all sixteen bits are read on the down-counter. Thus, when the rotating cam is at angular position 1FF hex, the next TICK will reset the up-counter to zero. The down-counter, of course, does not reset until the index 180 is read, at which point the down-counter is reset to the cam encoder offset value as provided by the system user.

At the digital control system control panel 134, the system user may enter a cam encoder offset number, which permits compensating for production variations associated with the mechanism itself. The use of two counters advantageously permits the routine to function, even if the index is missed after synchronization is acquired, even if the encoder misses counts, or has extra counts due to signal glitches. In the preferred embodiment, the down-counter is a 16-bit device, and the up-counter is a 9-bit device.

Thus, the digital control system 128 knows how many ticks on channel A exist between the index mark on channel B to the Zero point ("TICK 0") whereat one of the pistons crosses the zero point. This cam encoder offset value is also referred to as the alignment value. As such, the first part of applicant's code tracks where at a given point in time the cam mechanism is relative to index 0, the end of the intake stroke, with respect to piston head position.

It is important to appreciate that when the pump system is first started (or if the user desires), the routine commands a flow mode (as contrasted to pressure mode). Flow mode results in that there is no real time reliance upon output pressure data feedback, and motor 18 is operating at a constant rotational speed. Although transducer 40 provides pressure data, real time control of the speed of motor 18 is not dependent upon such data. By contrast, in a pressure mode of operation, pump 100 can make real time use of output pressure data.

Reference is now made to APPENDIX 1, pages 43–44. As will be described, fuzzy logic 100 intelligently permits pump system 100 to commence operation in a default flow mode. In default, system 100 is initialized to attain the system working pressure for the user-selected system flowrate. The user may wish to remain in flow mode, especially if runs involving varying viscosity are to be performed. On the other hand, pressure mode may be selected from the control panel if the user wishes to attain the advantage of lower pressure ripple.

However, even if pressure mode is user selected, the system will first default to flow mode and switch to pressure mode only after flowrate is determined to be established within a desired threshold, preferably ±3% of a nominal value, and the system operating pressure has been achieved. Whenever the threshold flowrate value is exceeded, the control system automatically reverts to flow mode operation until the flowrate is again maintained within the desired threshold tolerance. As such, system 100 can autonomously switch back and forth between flow mode, a mode best suited for compensating for rapid viscosity changes, and pressure mode, a mode best suited to reduce pressure ripple.

In the set up procedures at pages 36–37 of APPENDIX 1, the execution code at page 38, and the get data code at pages 44–47, a learning algorithm portion of applicant's fuzzy logic 150 is described, as well as a positive displacement flow control. By way of background, assume that the motor 18 is running at an arbitrary speed $\omega 1$ during the intake stroke, wherein one piston, e.g., 34A is exhausting, and that system 100 is functioning ideally with no leakage, compliance, or other variations.

As shown in FIG. 3, at cross-over, both pistons move outward in exhaust with both piston head areas pumping liquid. Thus, to maintain constant flowrate with both pistons exhausting, the motor speed must be reduced to approximately 0.5 $\omega 1$. In practice, reduction may readily be controlled between about 0.4 $\omega 1$ to 0.6 $\omega 1$. APPENDIX 1 sets forth the constant displacement control code at pages 39–42 and 36–39, with applicable fuzzy logic at pages 44–47.

Applicant's fuzzy logic 150 permits maintaining constant flowrate in a flow mode (e.g., without any pressure feedback) by operating motor 18 at a constant full speed during the intake stroke, and halving the speed during overlap. By definition, overlap starts when a piston crosses the center of the notch in cam 160, which notch is located approximately opposite position 1FF hex in FIG. 3. Overlap ends when the opposite piston moves over the cam nose, which nose is at the right-hand TICK 88 in FIG. 3. This flow mode operation controls output port 12 flowrate within about ±1% with very little ripple.

In practice, it is difficult to predict where in the motor cycle overlap actually commences and ends, during which time the motor speed should be halved, relative to an ideal motor speed during intake. For example, if motor 18 is optimized for 4,000 psi pressure such that motor speed is halved at two specific points during cam rotation, the pump 100 will exhibit substantial ripple at other than 4,000 psi. Further, even at 4,000 psi, if a change in pressure, liquid viscosity occurs, or a bubble is present, there will be substantial ripple in the output flowrate.

It is understood that during overlap, both cylinders are exhausting. However, one cylinder will be almost fully exhausted, whereas the other cylinder will just be starting its exhaust stroke. For the almost fully exhausted cylinder, the corresponding outlet check valve (e.g., valve 36A for cylinder 34A) will have been open, whereas the outlet check valve for the new cylinder just starting its exhaust stroke will now be opening.

The present invention recognizes that pistons 34A and 34B will never be identical in practice. For example, if examined on a diagnostic display, each piston would exhibit its own characteristic pressurization points, also called "p-points".

Pressurization points are numbers that represent where, in TICK count, a piston first becomes pressurized and thus active. With reference to FIG. 3, this will be where in the cam stroke (in terms of TICK location) the cylinder that is just beginning its exhaust stroke will actually start to pump liquid.

Pressurization-point characteristics can differ piston-to-piston due to production variations, seal variations, as well as the presence of bubbles, among other variables. Pressurization point numbers can range from 0–76 TICKS, with a wide discrepancy between pressurization numbers from cylinder to cylinder implying a leaky or otherwise defective cylinder or head.

A relatively larger pressurization point implies more compressibility, perhaps due to the presence of a bubble. A larger pressurization point number would thus indicate that the piston goes farther into the stroke to attain pressure within that cylinder. A relatively smaller pressurization point number implies less compressibility, and thus a higher pressure. At a higher pressure set point (e.g., system operating pressure), the number of TICKS required to pressurize a cylinder increases with a positive co-efficient. Thus, under ideal conditions, the pressurization point will be increased with increasing system pressure.

Applicant's fuzzy logic analytically determines the pressurization point for each cylinder using data from transducer 40 and from the disk encoder 126. With reference to FIG. 3, the pressurization point is the number of ticks relative to TICK 0 (e.g., from start of overlap) to the angular position whereat the rotational speed of motor 18 is slowed. As noted, the slowed velocity will be fixed at about 50% of the intake motor velocity within the cross-over, with a maximum pressurization-point occurring where overlap ends. In flow mode, motor speed is one of two fixed values, whereas in pressure mode, as overlap is entered the motor speed is momentarily reduced to 50% of nominal flow mode speed, and the pressure servo is reset at the pressure point. In contrast to flow mode, motor speed can continuously vary during pressure mode.

Thus, fuzzy logic 150 predicts for each piston when overlap occurs, permitting mechanism 30 to regulate the speed of each piston to achieve good flow mode operation. In flow mode, output flowrate will be relatively consistent as a function of motor speed. By flow mode monitoring pressurization-points and the constant displacement for each piston, applicant's digital control system 128 provides a useful diagnostic tool. Normally, the characteristics of each piston should be within some nominal range of each other (typically a few percent), and a widely deviating detected characteristic is indicative of a piston problem. This control system diagnostic capability simply does not exist in prior art pump systems.

A portion of applicant's fuzzy logic 150 predicts when the exhaust check valve will start moving for the piston that is going into the exhaust stroke, for example valve 36A for piston 34A. This prediction is based upon count ticks of detected cam slots 170. As was noted with respect to FIG. 3, cam index 180 tick 0 represents the start of overlap. In an ideal system (e.g., non-compressible liquid, no bubbles, and no system compliance deviation), the 0 tick would consistently represent the point at which the motor speed should be halved.

For example, at 300 psi, the pressurization-point display would show a number close to tick 0, perhaps 5 or 6. But at 4,000 psi, the p points would be higher, perhaps 70. In this manner, system compliance can be reflected by the pressurization-point readings for the different piston heads, materials, seals, fluids, and so on. For example, the presence of a bubble in the system will increase compliance, and the piston cylinder containing the bubble will exhibit higher pressurization-points than the other fluid path.

Thus, in a flow mode operation, without using pressure feedback, the present invention can compensate for variables such as fluid compressibility variations, compliance, leakage, a bubble. Not only can the present invention detect such variables, but they may be identified as to where in the system they are occurring. Further, in the case of a bubble, applicant's fuzzy logic 150 can actually approximate the bubble size, and discern the value of the pressurization-point relative to the other portion of the system.

Applicant's use of pressurization-point information permits flow mode operation of pump system 100, wherein a constant flowrate is maintained without having to use data from pressure transducer 40 for real time compensation of the speed of motor 18. Because it ignores real time pressure feedback data, flow mode operation permits pump system 100 to maintain flowrate even during sudden viscosity changes, or during analytical gradient runs. Such viscosity changes appear to have only a second effect upon flowrate, which effect is adequately compensated for by moving pressurization-points. Thus, in the preferred embodiment, flow mode is the default mode of operation.

Although flow rate mode advantageously is relatively insensitive to viscosity gradients, pressure mode under steady state conditions has the advantage of running a pump system 100 with less ripple. In applications such as ion detection or conductivity detection, the reduced pressure variation provided in pressure mode is advantageous.

To provide the best of both worlds, pump system 100 will automatically switch from flow mode to pressure mode operation whenever two conditions are met: (a) the constant displacement flow measurement time is within a threshold, preferably 3%, of the commanded flowrate, and (b) the piston being measured is at a higher pressure than the remaining piston. Condition (a) is determined mathematically by comparing the number of tick degrees and associated time to the commanded flowrate speed. Condition (b) is simply a matter of comparing pressures within each piston, since in flow mode both pistons are monitored. Typically transition from default flow mode to pressure mode occurs within about four piston strokes, which is two cam 360° cycles. Applicable code appears in APPENDIX 1 at pages 43 and 44.

Once transition from flow mode to pressure mode occurs, the piston determined in flow mode to provide higher pressure (e.g., the piston associated with less leakage) is the only piston referenced with regard to the constant displacement during pressure mode. Thus, if in flow mode piston 34A was determined to have a higher pressure than piston 34B, upon entering pressure mode only the constant displacement of piston 34A will be considered, and piston 34B will be ignored. Please see APPENDIX 1, pages 45 and 46.

Thus, in stark contrast to the prior art, this discrimination between pistons permits system 100 to function properly, and compensate for the occurrence of a defective piston. Understandably, the higher pressure of the two (or more) pistons will be the piston that will better operate at the constant motor speed associated with pressure mode operation.

Assume then that the conditions for exiting flow mode have been met, and pump system 100 is now in pressure mode, with piston 34A having been determined in flow mode to be the higher pressurized piston. In pressure mode, each time the cam makes one revolution, the time required for the cam to move through the last 45° (e.g., $170_h$ to $1F0_h$ w2) of the intake stroke of piston 34A is measured by a counter within digital control system 128. This 45° region corresponds to the arc between points A and B on came 160 in FIG. 3.

With reference to APPENDIX 1, page 44, the measured time is compared to the commanded flow time and the control system decides whether to continue in pressure mode or to change to flow mode. In the preferred embodiment, if the flowrate error exceeds 3%, flow mode operation is resumed, using parameters that were in effect when pressure mode was entered. Once back in flow mode, the preferred embodiment causes four more cam strokes to occur to re-equilibrate the pump to begin anew to meet the two conditions necessary to leave flow mode. On the other hand, if the error is less than 3%, pressure mode continues. The pressure set point is changed to maintain the proper time and flow rate.

Applicant's pressurization-point algorithm uses artificial intelligence or fuzzy logic routine, wherein instead of using a model and formulas, measurements are made of a group or an event, and are placed in one of two membership sets. A decision is then based on which membership set the information is in, the decision being where to put the pressurization-point.

In the preferred embodiment, the pressurization-point algorithm is a core element in implementing the flow mode, but is also active during pressure mode operation. The pressurization-point algorithm is denoted as AI (for artificial intelligence) in APPENDIX 1.

The summary of the AI routine appears at pages 44 to 47 of APPENDIX 1 herein. The AI routine requires five different break points or tick counts, based on the zero tick count noted in FIG. 3. With further reference to FIG. 3, while there are 1024 ticks defining the perimeter of disk 126, the tick count need only go from count 1 to 511 to be able to pick up the opposite piston. As such, count 0 can mean that either piston 34A or 34B is starting its overlap point, other means being used within the code to track the piston.

With reference to FIG. 3, the tick count is relative to tick 0 and can be for either piston 34A or 34B. There is a mechanical overlap that goes from tick count 0 to a count corresponding to 29° (overlap), which is approximately count 88. However, there also exists a hydraulic overlap that represents the pressurization-point count, which can vary from 0 to 29°.

A portion of the code within logic 150 is directed to the process of determining at what point in the travel of cam 126 rotational speed of motor 18 should be slowed to reduce and control cross-over. Proper control of crossover reduces overlap ripple, and thus pressure and flowrate ripple. Reducing cross-over is used in both flow mode and in pressure mode operation.

In pressure mode, at higher flowrates system delays and other factors can prevent the system from responding to the pressure peak caused by the overlap. One advantage of the applicant's algorithm is that the feedback is augmented such that the cross-over ripple is reduced even at higher pump speeds and under dynamic system conditions.

Under many steady state conditions with normal pump speeds, even prior art pressure feedback can reduce pressure ripple effectively. However, under dynamic conditions, due to viscosity changes, high speed operation, rapid change in system parameters as in switching columns or during an injection, the present invention reduces cross-over ripple, whereas prior art techniques cannot.

With reference to APPENDIX 1, pages 33–52, 1FF hex represents the end of the intake stroke stoke and is next to the 0 tick shown in FIG. 3 (however, the 0 tick is associated with piston 34B, whereas 1FF is associated with piston 34A), while 1F0 hex represents tick count 88, the cross-over point for piston 34B.

In the preferred embodiment, as shown at pages 45–47 in APPENDIX 1, an average intake pressure is formed. This value is formed by averaging pressure when one piston is in intake and the other one piston is late within the exhaust stroke but before overlap (e.g., before the first piston also begins exhausting). Pressure samples are taken for each count tick and are averages on a piston as the system goes into overlap at a time period surrounding the pressurization point.

Window 1 is an overlap pressure average window, and is centered about the pressurization-point number. Window 1 begins a fixed integer m, e.g., m=8, and ends a fixed integer n, e.g., n=24, after the p-value. Thus if the pressurization-point=20, the start of the window 1 averaging will be 20−8 or 12, and the end of the window 1 averaging will be 20+24=48. As such, the width of the window is constant (e.g., 32 tick width) and window relative position, with reference to p-position, is constant (e.g., a constant offset from the p-position).

An average of pressure taken during this window 1 period is compared with an average taken within the stable, good pressure portion of the stroke wherein one piston was running smoothly (window 2). The reference window 2 sample will always be taken just before tick 0, e.g., while the new piston is still in its intake stroke and thus in a non-overlap, steady-state portion of the cam cycle.

Figure 4A:
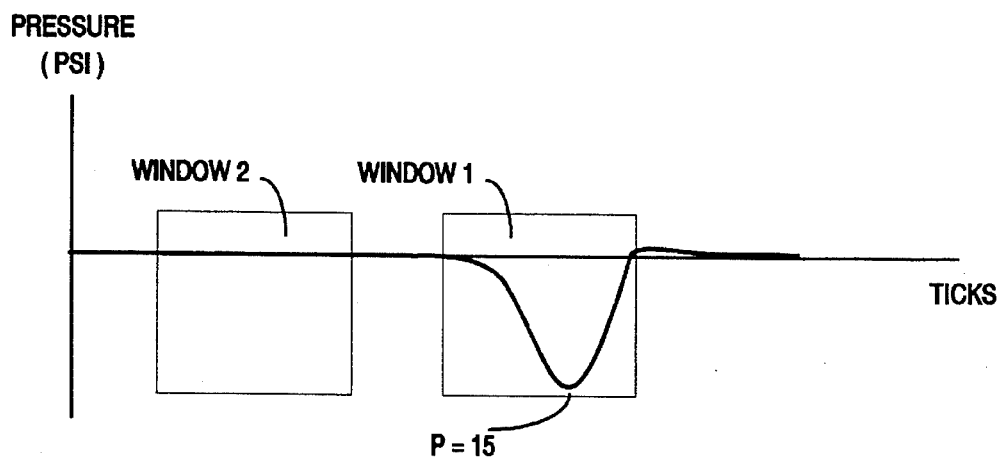
FIGS. 4A–4C depict pressure ripple and its reduction by advancing or regarding pressure points, according to the present invention.
Figure 4B:
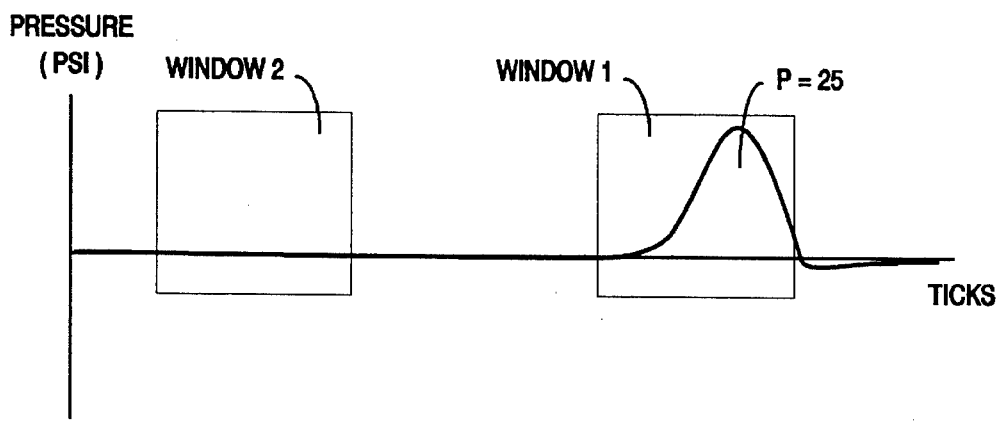
Figure 4C:
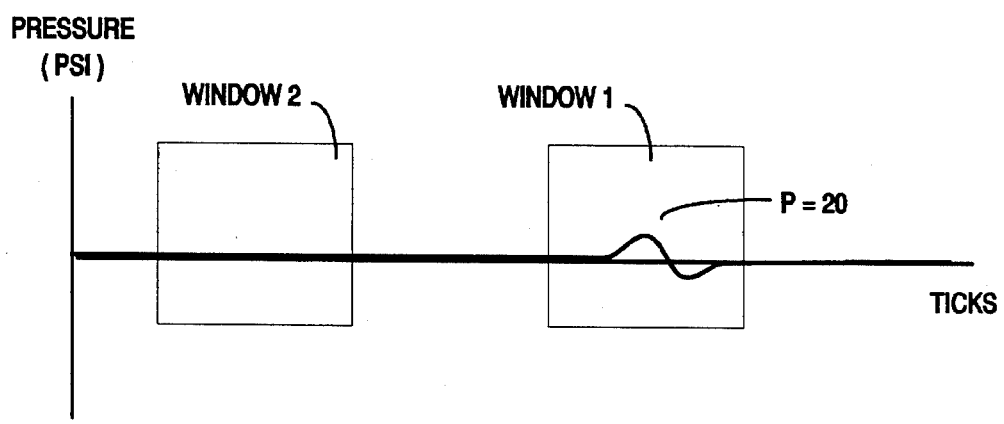

As shown in FIGS. 4A, 4B, 4C, reference window 2 is static in the sense it always starts and ends at the same point in the cam travel. In practice, the angular width of window 2 may be from about 12.5° to about 135° of cam rotation, although applicant has found 12.5° to be a good compromise value that tends to equalize flowrate for pressure mode and for flow mode. With respect to FIG. 3, if window 2 were 90° of cam travel, it would start at 0F0 hex (TICK 240) and would end at 1F0 hex (TICK 496). More preferably, window 2 is about 12.5° of cam travel, and would start at 1D0 hex (TICK 464) and extend to 1F0 hex (TICK 496). As such, reference window 2 may be fixed in size at 32 TICKS, since it is known where on the cam travel the good performance data should occur.

For reference window 2, pressure is averaged by sampling the running pressure at each TICK from TICK 1D0 hex to 1F0 hex, and then dividing the resulting sum by 32. Please see APPENDIX 1, page 49, AVTIME routine, wherein this is set up. The OVAVG routine at pages 50–51 in APPENDIX 1 executes the averaging operation.

By contrast, the overlap pressure average window 1 is centered about the predicted pressurization point as predicted by the fuzzy logic algorithm (see APPENDIX 1) using output pressure information from transducer 40. The window 1 sample will occur just past tick 0 and, as shown in FIGS. 4A–4C, may move about, in terms of TICK location, in contrast to the static reference window 2. In FIG. 4A, for example, window 1 is centered about a predicted pressurization point of 15. As shown in APPENDIX 1, page 47, in the preferred embodiment, window 1 and window 2 are each 32 TICKS wide, although the windows need not be equal in size.

With reference to APPENDIX 1, pages 46–47, the routine is shown that provides a one stroke delay to the p-point update (referred to as a "modifier" in the code listing). This routine also assigns the start and stop points for window 1. The OVFLW routine picks up the left-right flag (LRFLG), which it uses to assign the correct p-point to the appropriate piston. This is handled by controlling an address pointer in the OVFLW routine. In APPENDIX 1 at page 47, window 1 is set up, and starts 8 TICKS before the p-point value, with a start point limit of 0 established by the routine. Thus, if the p-point is 4, the start point will be 0, not −4. Similarly, the stop or end point of window 1 is set to 24 TICKS after the p-point value, with no maximum limit imposed by the routine.

Comparing these two window 1, window 2 averages, fuzzy logic 150 decides whether to retard or to advance the pressurization point to vary the rotational speed of motor 18.

With reference to FIGS. 4A, 4B, and 4C, FIGS. 4A and 4B show, respectively, a pressure dip with an associated pressurization-point number of 25, and a pressure peak with an associated pressurization-point number of 15. However, by suitable retarding or advancing, a nearly ripple-free pressure curve is arrived at in FIG. 4C with an associated pressurization-point value of 20. As noted, the pressurization-point represents the number of ticks from 0 to where motor speed is halved within the cross-over region.

In FIG. 4A, a pressure dip is shown, representing a ripple component. According to the present invention, an average pressure measurement in taken within window 1, associated with an overlap transient piston region, and within an equal-sized window 2, associated with the last part of the stable intake piston stroke. In FIG. 4A, the pressure in window 1 is too low, which implies that motor 18 is slowly down too soon. Thus, it is desired to delay the slow down of motor 18 to advance the pressurization-point (e.g., to move it rightward in the figure) to a value higher than the p=15 shown.

By contrast, FIG. 4B shows a pressure peak, wherein too high an average pressure occurs during window 1 relative to the average pressure read within window 2. The excess pressure in window 1 implies that the motor 18 is being sped-up too soon, the correction for which is to retard (e.g., move leftward in the figure) the pressurization-point from the p=25 value shown.

In FIG. 4C, motor 18 is commanded by control system 128 at approximately the correct time because there is a cancellation of a pressure peak with a corresponding pressure dip. A comparison between the average pressure readings within windows 1 and 2 is essentially even. When the comparison is essentially even, applicant's algorithm by default will advance the pressurization-point. This default advance is desired because if the system is operating at low motor speed and the feedback system can respond quickly enough to compensate and remove the ripple transients, the pressurization-point is increased to the overlap limit point, e.g., the end of overlap. This, in essence, eliminates the adjustment, since the motor speed is to be increased at end of overlap, thus cancelling the motor speed change. Eliminating the adjustment reverts to a prior art mode, namely slow speed with steady pressure.

The above-described technique wherein averages are taken between tightly coupled window 1, window 2 samples resulted from many months of experimentation wherein no alternative technique for arriving at a suitable correction under actual operating conditions was discovered. For example, attempting to use the pressure at the pressurization-point to make correction leads to difficulties under various conditions due to the delay between the actual and sensed pressure.

Further, system gain must be reasonably low to prevent oscillation when motor speed is running fast, which further complicates the p-value correction process. Even attempting to compensate by more than one tick for relatively large differences between window 1 and window 2 data was considered and rejected in that the absolute value of the window 1 peak magnitude is not readily related to the number of corrective ticks. In short, the above-described window-average, wherein the sample window 1 moves about with the pressurization-point appears to represent the best solution discovered by applicant for practical applications.

In pressure mode with the pump 100 running under steady-state conditions, pressure gain is not known. Pressure gain is the amount of real-time correction that the motor speed is commanded by control system 128 to take for a given pressure variation. Further, no adequate model is known from which pressure gain may be derived in pressure mode, apparently due to large compliance changes. The inability to predict pressure mode pressure gain precludes swapping piston heads 34A, 34B in the prior art, for example, to change from a standard pump to a microbore pump system.

In the present invention, logic 150 includes an algorithm that sets the pressure gain to an optimum value each time pressure mode is entered. The relevant code sections appear at APPENDIX 1, pages 49 to 50 (see intime routine).

According to the present invention, pressure gain is initially set to a default high level such that under most conditions, pump system 100 may begin to oscillate, especially under conditions of low pressure and low compliance. The relevant algorithm monitors pressure and checks for oscillation during the intake portion of the pump cycle. Oscillation is detected by looking for a pressure peak greater than 3% above a set point, followed by a pressure dip exceeding 3% less than the set point, the set point being determined by the pump operation. Of course, the presence of oscillation could be confirmed in a reverse sensing direction as well, e.g., a dip followed by a peak.

Oscillation monitoring is only during intake as too many changes may occur simultaneously during overlap that could generate a pressure ripple that interferes with such monitoring. Also, since both pistons are pumping, the pressure gain is different during overlap.

If oscillation is detected during intake, logic unit 150 decrements system pressure gain by a small amount. If oscillation continues to be detected during intake, the pressure gain continues to be reduced until eventually no oscillation is monitored during intake. In this manner, a highest stable system pressure gain is ascertained and dynamically maintained on the fly. By contrast, in the prior art, pressure gain was manually preset using toggle switches to program in known compensation. However the compensation known to provide suitable pressure gain when the pump system was first used did not necessarily continue to provide good compensation as the pump aged, or the piston head materials were changed.

The above-described ability to optimize pump pressure gain on the fly permits great flexibility in manufacturing pump system 100. The materials and tolerances with which the pump system is fabricated may now be changed with great leeway. Further, piston heads and head sizes, as well other components may be field replaced and logic unit 150 will continue to maintain the requisite flowrate tolerance by automatically optimizing pump pressure.

Figure 5:
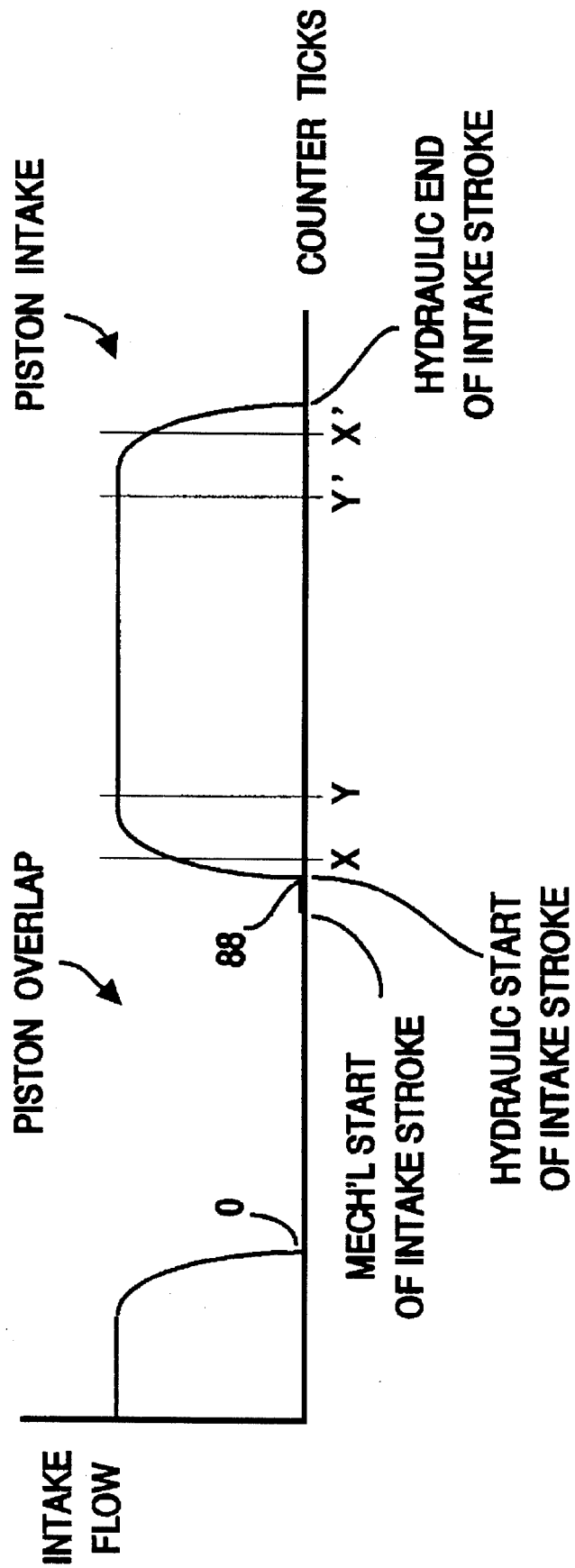
FIG. 5 depicts intake flow into the piston heads and the constant intake flow portion thereof used by the present invention.

With reference to APPENDIX 1, pages 47–49, FIG. 5 depicts intake flow into the piston heads as a function of time. Using piston head 34A as an example, at time 88, exhaust check value 36A closes, intake check valve 32A opens and liquid from source 16A is drawn into the cylinder as the piston head withdraws. When the check valve 32A opens, intake flow begins and continues for a period of time until the piston starts forward, closing check value 32B and opening exhaust valve 36A at tick 0, when overlap commences. While the time duration of the intake flow can vary with a pump system configuration, the duration is typically on the order of perhaps 5 seconds at about 1 ml/minute.

FIG. 5 demonstrates, however, that there is not an instantaneous change from zero flow to full intake flow and vice versa. When the mechanical start of intake commences, intake flow will remain zero while system compliance is taken up, and after additional delay the hydraulic start of intake will commence. While the mechanical start of intake is known from the encoder disk (albeit somewhat inaccurately known), hydraulic start of intake is an unknown. At hydraulic start of intake a gradual transition up to constant intake flow occurs. At the end of intake, there will similarly be a gradual transition down to zero intake flow. These gradual transitions each represent perhaps 2% of the total intake time period (about 7 TICKS), or perhaps 0.1 seconds. The slow transition results from delay in opening the input check valves, from the hydraulics associated with the acceleration of the liquid entering the piston cylinder to reach a maximum velocity, among other factors.

It will be appreciated that during the transition time, for example at TICK X, the intake flow and thus the flowrate are changing and are unknown. However, at TICK Y, intake flow is stabilized and the flowrate will be a known constant.

It is evident that when running a gradient or a proportioned isocratic mixture, the gradual transition characteristics shown in FIG. 5 will result in poor analytical results. In a mixture, the component liquids are proportioned into the cylinders during the intake stroke. However, during the curved portion of the intake, the flowrate is unknown, which uncertainty causes a variability in the composition of the piston volume that will be pumped and provided through the output port 12. By contrast, proportioning during over later than TICK Y will take place when intake flow and thus flowrate are constant.

The prior art attempts to cope with the flowrate transition by imposing a fixed time delay from start of intake before commencing proportioning. However, the fixed time delay will work well only within a limited pressure regime, for example approximately 2,000 psi. However, when using a prior art system at another pressure, perhaps 500 psi, the fixed time delay no longer ensures that proportioning occurs during the fixed intake flow regime. Even if an assortment of toggle switches are provided to change the delay according to historical data, changes that may have been effective with a prior art pump system was new will not necessarily be effective when the pump has aged, or components have been changed.

By contrast, the present invention dynamically correctly compensates for the transitioning intake flow independently of the pressure. Since pump 100 does not include a sensor to discern start of hydraulic flow, empirical methods are provided by logic 150. The empirical data were generated over several actual chromatography runs at several pressures for each of several heads, and an appropriate compensation factor was noted as the pressure was changed.

A proper compensating factor depends upon the length of the intake hydraulic stroke, and a knowledge of when the hydraulic stroke actually starts. The intake stroke length is needed to control portioning Assume, for example, that the control system CPU commands a 75%:25% proportioning, e.g.,input from liquid source 16A for 75% of the intake cycle, and from liquid source 16B for 25%. It is therefore necessary that check valve 36B be opened for 25% of the tick length of the stable portion of the hydraulic intake cycle, and check valve 36A for 75% of the tick length. (It will be appreciated from FIG. 5 that since TICK error can accumulate from the mechanical start, that more accurate proportioning will occur by flowing the larger here 75%, proportion of the liquid first and last in the intake cycle, and the smaller, here 25%, in the center.)

With reduced pressure, the start of hydraulic flow will move leftward in FIG. 5, e.g., have a smaller number TICK assignment, and thus have a positive co-efficient. However, when pressure increases, the stroke length decreases, which gives a negative co-efficient. Applicant's algorithm causes the location of TICKS Y and Y' to move about as pressure changes, to maintain a constant intake flow regime for proportioning.

This dynamic, on the fly compensation uses data from output pressure transducer 40 for a reference. The portion of logic unit 150 providing this correction also makes use of the window 2 reference pressure described with respect to FIGS. 4A, 4B and 4C. This dual use is possible because the window 2 reference pressure information is derived at the end of the intake stroke. This information is then used to set up the end of the next intake stroke.

Thus the CPU associated with digital control system 128 issues a command for the start of each intake stroke, before which command the window 2 reference data will have already been processed. From the reference 2 average data, the intake stroke length and corresponding number of TICKS may be derived for each check valve breakpoint (e.g., when the valve is to start to move).

The preferred embodiment has been described with respect to a liquid chromatography pump system 100 manufactured by assignee Dionex Corporation, Sunnyvale, Calif., and marketed as Dionex Model DX500/GP40 gradient pump. However, those skilled in the art will recognize that the present invention may be used to control a precision pump in applications unrelated to liquid chromatography.

Those skilled in the art will appreciate that the default flow mode is implemented as a two stage servo system such as depicted in FIG. 6A, and comprises a constant displacement flow servo loop and a motor speed servo loop. With reference to FIG. 6A, flow set point data that is time sampled from the encoder disk 126 is input to the constant displacement loop, which loop is updated once per piston stroke. This first loop outputs a motor tachometer set point as input to the motor speed servo loop, which is coupled to applicant's digital control system fuzzy logic 150 (see APPENDIX 1). In flow mode, the fuzzy logic algorithm updates once per piston stroke, but delays by one piston stroke (see APPENDIX 1, page 45–47). The digital signal processing code for the operation of the overlap speed adjust routine appears in APPENDIX 1 at page 38. This portion of the routine provides adjustment for both flow and pressure modes of operation.

This inner motor speed servo loop compares the motor tachometer speed with the motor drive voltage. As has been described, the fuzzy logic sets the time at which the rotational speed of motor 18 is changed (by approximately 2:1) to vary between first and second motor speeds to accommodate overlap. The output of the second loop is the mechanical rotation of shaft 24, which is coupled to mechanism 30. Thus, acting together these two loops regulate flowrate without real-time use of pressure output data during flow mode.

Referring to APPENDIX 1, page 38, applicant's adjust routing is set forth, wherein the first few instructions take the nominal motor speed set point (e.g., the motor operating set point during intake), and multiplies this speed by a STRTSP coefficient. The product yields a new set point for motor speed operation during the actual pump overlap period. When the overlap period is completed the routine is run again to restore the set point to the intake nominal value.

By contrast, the pressure mode operation is a three stage servo system as shown by FIG. 6B. In pressure mode, the motor speed tachometer set point is input to an inner motor speed servo as was above-described. This tachometer set point is controlled by the output from a pressure servo, and the pressure set point is determined by constant displacement by a constant displacement flow servo.

The constant displacement flow servo updates once per two piston strokes, whereas the fuzzy logic algorithm updates once per piston stroke but delays one piston stroke (see APPENDIX 1, page 36–39). It will be appreciated that in pressure mode, instead of a constant motor speed (as in flow mode), the pressure set point at which the system is running controls the motor speed set point.

In pressure mode, using well known techniques, the motor speed set point is determined by a servo algorithm that includes a filter (see APPENDIX 1, page 58). In this algorithm, the error is the input and the output is the output and the algorithm operates recursively. The next time that it is run, the new error value becomes the error, whereas the old error value becomes the delayed error. Further, the new output value is the output, and the old output value becomes the delayed output. The next time after that, the old delayed values are discarded and replaced by the old values.

The result is that motor speed may vary widely as the pressure servo attempts to maintain constant pressure. In pressure mode, applicant's OVADJ routine initializes the pressure servo each time that it runs. The first two routine steps force the motor speed to the flow mode overlap or intake value, and the next two steps clear the pressure servo delayed error value to minimize transients. After this routine runs, the pressure servo is again free to change the motor speed to maintain the pressure setpoint, even during overlap.

Modifications and variations may be made to the disclosed embodiments without departing from the subject and spirit of the invention as defined by the following claims.

```
{
PUMP RUN PAGE DSP CODE
}
{
REV 208 ADDS BALLS TO WALL BIT
DISABLE FOR SPEEDS HIGHER THAN AROUND
30 RPM
REV 207 ADDS IMPROVED PRESSURE
FEEDBACK SAMPLING AND FILTERING
ALGORITHM; CPU PRESSURE IS
DIVORCED FROM SERVO FEEDBACK PRESSURE
AND CPU PRESS HAS TIME CONSTANT
OF 600 MS ALSO 207 HAS PRESSURE
SAMPLE PERIOD AT END OF INTAKE
DIVORCED FROM TIMING PERIOD  TIMING
PERIOD INCREASED TO 90 DEGREES
REV 206 ADDS STATUS REQUEST STROBE
AND DIRECT DEGAS CONTROL
REV 205 ADDS DUMMY READ FOR ADC
ADDRESS SETUP
REV 204 IMPROVES MOTOR SAMPLE ROUTINE
BY ADDING A STROBE TO OBTAIN MOTOR
SAMPLE BEFORE PROCESSING IT
REV 203 ENHANCES BALLS TO WALL BIT
SETUP TO FIX TIMING TO END OF EXHAUST
STROKE
REV 202 PROVIDES BALLS TO WALL
MOTOR RUNAWAY INDICATOR BIT  ALSO
REV 202 CHANGES DEGAS ON/OFF INDICATOR
TO DETECT STATE RATHER THAN CHANGEOVER
REV 200 ADVANCES AI ALGORITHM ROUTINE
INTELLIGENCE TO PROVIDE GOOD FLOW MODE
LEARNING IN COMPLIANT SITUATIONS
REV 196 PROVIDES FOR P-POINT INITIALIZATION
DIFFERENCES BETWEEN HEAD TYPES
REV 194 AND 195 ADDED VARIABLE P-POINT
INITIALIZATION
REV 193 FIXED BUG IN PROPORTIONING
COMPLIANCE COMPENSATION ROUTINE
REV 192 CHANGES THE PISTON BIAS ROUTINE
SO THAT THE SLICES RATHER THAN THE
MIDDLE IS AFFECTED
REVS 188-191 ADDED DIAGNOSTIC FEATURES
AND FIXED BUGS FOUND DURING MANUFACTURING
REVS 185-187 PROVIDED IMPROVED RIPPLE
PERFORMANCE.
V184 ADDS A NUMBER OF FEATURES IN
ORDER TO CUT PRESSURE RIPPLE DOWN
FIRST THE INTAKE GAIN RESTORATION
WAS MOVED TO ENCODER ROUTINE AND
ONLY EXECUTES WHEN OSC DET PERIOD STARTS
SECOND THE OVERLAP GAIN WAS INCREASED
THIRD THE OVADJ ROUTINE WAS MODIFIED
TO ADD PRESSURE SERVO DEL INPUT
RESET.  THIS DRAMATICALLY REDUCED
```

RANDOM SPIKING AT OVERLAP START.
FOURTH, A FUDGE FACTOR WAS ADDED
TO HELP THE LEARNING ALGORITHM
PICK THE CORRECT POINT TO CUT MOTOR
SPEED. THIS CUT THE NARROW SPIKES
DOWN QUITE A BIT.
V183 MOVES OVERLAP GAIN REDUCTION
TO POINT WHERE OSCILLATION DETECTION IS
INITIATED
V180 RE-ACTIVATES PRE OVERLAP GAIN REDUCTION
REDUCES OVERLAP SPEED SLIGHTLY
INCREASES PRESSURE GAIN
ADDS ABSOLUTE CLAMP OF 500 TO OSC DETECT
CLAMP.
V2170 MOVES ACTUATION OF GAIN CHANGE
FOR OVERLAP TO STATIC FEATURE POINT
V2160 OPERATES QUIET MODE XYLINX
PROMWARE.
TWEAKS ON 2152 FOR QUIET MODE
ELIMINATES OLD VELOCITY MODE BUG
DATING TO V100 FOR SMOOTHER STEADY
STATE OPERATION.
V2152 RELEASED TO ALPHA 4-23-93
V2152 HAS SEVERAL UPGRADES
FIRST THE LEARNING ALG IS
IMPROVED.
1) DELAY IS ELIMINATED; OVERLAP AVERAGING
   IS SPLIT FROM INTAKE AVERAGING
2) THE AVERAGING PERIOD IS SHORTENED
3) THE AVERAGING PERIOD MOVES TO
   FOLLOW THE OVERLAP START POINTS
   FOR EACH PISTON
4) THE INCREMENT IS 1
   SECOND A PISTON PICKER IS ADDED
1) HIGHER PRESSURE PISTON IS USED AS
   REFERENCE FOR PRESSURE MODE OPERATION
2) IN PRESS MODE FLOW IS CHECKED ONLY
   FOR HIGHER PRESS PISTON
THIRD THE SLIDE FACTOR ADJUSTS
CROSSOVER SPEED AS PRESSURE CHANGES
FOURTH THE PRESSURE SETPOINT FOR
TRANSITION FROM FLOW TO PRESS MODE
IS THE AVERAGED INTAKE PRESSURE
FIFTH THE FLOW TIMING ANGLE WAS REDUCED
BY 50% ONCE AGAIN.
V2151 HAS OPENED UP VELOCITY
SERVO ERROR CLAMP AND INCREASED
PRESSURE FEEDBACK.
V2150 ADDS FLOW MODE FEATURE
FLOW MODE
o HAS INTELLIGENT INITIALIZATION o KICKS IN FOR VISCOSITY CHANGE OR
  COLUMN SWITCH.
o ADJUSTS NOMINAL SPEED TO PRECISELY
  MATCH COMMANDED FLOW RATE.

o ADJUSTS PRESSURE SETPOINT FOR
  SMOOTH TRANSITION TO PRESSURE
  FEEDBACK MODE AND MINIMIZED UPSET
  DURING VISCOSITY CHANGE OR COLUMN
  SWITCH
o REQUIRES NO SPEED CLAMPS
V2140 RELEASED TO ALPHA 01-28-93
V2140 IS THE PUMP RUN PAGE WHICH IS
INTEGRATED AND LINKED TO THE DSP BIOS
V2140 ALSO FEATURES NEW ADAPTIVE
CROSSOVER COMPENSATION ALGORITHM WHICH
WAS TO BE PLACED IN V2150
}
{SET UP AS FIRST BOOT PAGE}
{
STATUS WORD BIT ASSIGNMENT:
BIT 0 POWER UP STATUS. CLEARED WHEN CAL
COMMAND IS GIVEN BY CPU
BIT 1 ENCODER INDEX NOT LOCATED. CLEARED
WHEN INDEX IS FOUND.
BIT 2 SET WHEN IN FLOW MODE
BIT 6 HI PRESS LIMIT TRIP SET WHEN OVPRESS
OCCURS CLEARED WHEN FLOW COMMAND RECEIVED
BIT 7 LO PRESS LIMIT TRIP BEHAVES SAME AS
BIT 6.
BIT 3, 4.   PUMP PROGRAM
            00=BIOS
            01=CALIBRATION
            10=PUMP RUN
            11=DIAGNOSTICS
}
{
AN EXPLANATION OF THE I REG USES:
I0: ^FILTER; ENCODER ROUTINE DATA MEM CACHE
I0: ^FILTER; TIMER ROUTINE TIMER DATA
I0: ^FILTER; COMM ROUTINE FLOW COMMAND
I0: ^VALV_BRK; COMM VALVE BREAKPOINTS
I1: ^FILTER; MOTOR ROUTINE DATA MEM CACHE
I2: ^VALV_BRK; E. R. VALVE BREAKPOINTS
I3: ^ADC; MOTOR ROUTINE ADC PORT
I4: ^COEFF; M. R. LOOKUP DATA
I5: ^VALVS; E. R. VALVE SETTINGS
I6: ^COEFF; E. R. LOOKUP DATA
I6: ^VALVS; C. R. VALVE BREAKPOINTS
I7: ^COMWD; USED IN DIAGNOSTICS

```
}
{
INTERRUPTS ARE NESTED:
MOTOR_SAMPLE HAS HIGHEST PRIORITY AND
RUNS ALL THE WAY THROUGH WITHOUT
INTERRUPTION ONCE STARTED. MOTOR_
SAMPLE RUNS ON SECONDARY REGISTERS.
ENCODER ROUTINE MAY BE INTERRUPTED
BY MOTOR SAMPLE AT ANY TIME. THERE-
FORE IT RUNS ON SEPARATE IREGS AND

ON PRIMARY DREGS.
TIMER ROUTINE HAS LOWER PRIORITY
BUT IS BRIEF AND INFREQUENT. THERE-
FORE IT BLOCKS INTERRUPTION FOR
THE DURATION.
COMM ROUTINE HAS LOWEST PRIORITY.
IT BLOCKS OUT INTERRUPTS WHEN ACTIVE
AND ENABLES INTERRUPTS WHILE IDLE.
COMM RUNS ON PRIMARY DREGS AND SHARES
IREGS WITH ENCODER AND COMM ROUTINES
EXCEPT I2 AND I5 WHICH ARE USED BY
ENCODER ROUTINE TO SEQUENCE THE
PROPORTIONING VALVES  I3 IS
AVAILABLE FOR USE BY THE COMM ROUTINE
SINCE THE COMM ROUTINE BLOCKS OUT
THE MOTOR SAMPLE WHILE IT IS ACTIVE
}
{
DECLARE CONSTANTS
}
{
  DATA CONSTANTS
  }
 {SERIAL PORT 1 CONTROL SETTING:
INTERNAL SERIAL CLOCK GENERATION SET
FRAME SYNC REQUIRED
SYNC ON SAME CYCLE AS FIRST DATA BIT
INTERNAL FRAME SYNC REQUIRED
ACTIVE HIGH FRAME SENSE
16-BIT WORD LENGTH}
{EEEE SET TO 001B FOR 2105
SYSTEM CONTROL SETTINGS
SERIAL PORT 1 DISABLED
SERIAL PORT 0 ENABLED
BOOT PAGE 0
3 WAIT STATES FOR BOOT MEM
3 WAIT STATES FOR PROG MEM}
{ALL TO 1 WAIT; 1 WAIT = 1249}
{
```

```
TIMER CONSTANTS; SET UP INTERNAL TIMER
}
{FULL SCALE}
{23 US PER COUNT}
{INITIALIZE COUNT}
{
 LOOP CONSTANTS
}
{WAIT FOR ADC SAMPLE}
{WAIT FOR MOTOR SAMPLE}
{
POINTER CONSTANTS.  THESE POINTERS INDICATE
MEMORY-MAPPED CONTROL REGISTER LOCATIONS
}
{SERIAL CLOCK DIV MOD}
{RX FRAME SYNC MOD}

{SERIAL PORT CONTROL}
{SERIAL PORT CONTROL}
{RX FRAME SYNC MOD}
{SERIAL CLOCK DIV MOD}
{DATA MEMORY WAIT}
{SYSTEM CONTROL}
{SET INTAKE STROKE LENGTH}
{SET OVERLAP SPEED}
{SET PRESSURE SERVO PATH GAIN}
{SET OVERLAP SLIDE FACTOR}
{SET FLOW MODE DELAY TIME FACTOR}
{SET OVERLAP AI GAIN FACTOR}
{
VARIABLE DECLARATIONS
}
{
PROGRAM MEMORY COEFFICIENTS REQUIRED TO
EXECUTE MOTOR VOLTAGE CONTROL LOOP AND
ENCODER ROUTINES
}
{
COEFF IS A CATCH-ALL; THESE ARE ACTUALLY
CONSTANTS USED TO PERFORM VARIOUS OPERATIONS
WITHIN THE VARIOUS ROUTINES.  I4 AND I6 ARE
SET UP TO A LOCATION WITHIN THIS STRING TO
RUN EACH ROUTINE
}
0X828000,0X7D8C00,0X800000,0X007F00,0X006000,
0X910000,0X700000,0X800000,0X020000,0X010000,
0X01FF00,0X001000,0X007000,
0X007000,0X01F000,0X7FFF00,0X800000,0X000000,
0X0FFF00,0X1FFF00;
{PRESSURE ERROR CLAMP (1FF)
```

```
PRESSURE PATH GAIN (FFFF)
PRESS ERROR COEFF (8280)
PRESS DELAYED ERROR COEFF (7D8C)
PRESS DELAYED ERROR COEFF (8000)
SPEED ERROR CLAMP (07F)
SPEED PATH GAIN (60)
SPEED ERR COEFF (9100)
SPEED DEL ERR COEFF (7000)
SPEED DEL OUTPUT COEFF (8000)
MOTOR SHIFT VALUE, DEAD TOGG MASK (0200)
ENABLE MASK, ENC INDEX MASK 1&2(0100)
EDGE COUNT 3 MASK (1FF)
HYDRAULIC OVERLAP START (10)
START OSCILLATION DETECT COUNT (080)
START FLOW TIMER COUNT (0F0)
STOP FLOW TIMER COUNT (1F0)
TIMER CLAMP (7FFF)
TIMER INVERT NUM MSB (8000)
TIMER INVERT NUM LSB (0000)
FLOW ERROR CLAMP (0FFF)
FLOW PATH GAIN (3FFF)}
{

THE COMM TABLE IS A LIST OF COMMAND CODES
USED IN THIS PROGRAM.
}
0X006000,0X000300;
{PROPORTION CONTROL COMMAND 7
INJECT CONTROL COMMAND 30
FLOW CONTROL COMMAND 10
PRESSURE LIMIT SET COMMAND 60
BOOT COMMAND 3}
{
DATA MEMORY CACHE REQUIRED TO EXECUTE
MOTOR VOLTAGE CONTROL LOOP AND ENCODER
ROUTINES
}
{FILTER IS DATA MEMORY CACHE:
HI PRESS LIM
LO PRESS LIM
COMP DELAYED INPUT VALUE
COMP DELAYED OUTPUT VALUE (SPEED COMMAND)
NOMINAL SPEED COMMAND
NOMINAL SPEED OFFSET
ADC SAMPLE FLAG
SPEED FEEDBACK CACHE
DELAYED SPEED ERROR VALUE
DELAYED SPEED OUTPUT VALUE
DEADMAN TOGGLE VALUE
CAM-ENCODER ALIGNMENT FACTOR
```

EDGE COUNT 2
EDGE COUNT 3
TIMER VALUE MSB'S
FLOW COMMAND
FLOW UPDATE FLAG
FLOW CHANGE TIMEOUT COUNTER MSB'S
INJECT TIMEOUT OR FLOW CNTR LSB'S}
{
FILTFLOW SETS UP THE PRESSURE AVERAGING
ROUTINE
}
{FILTER COUNT
ACCUMULATED VALUE
PRESSURE OFFSET
CORRECTED PRESSURE
LEFT P-POINT
RIGHT P-POINT}
{
SPEEDSET IS A TOOL USED TO
TROUBLESHOOT AND OPTIMIZE
AND STUDY VARIOUS PARAMETERS
}
{.VAR/CIRC SPEEDSET(0X40);}
{
VALVS IS THE ARRAY FOR THE PROP VALVE
SETPOINTS WHICH ARE RECEIVED FROM THE
COMM ROUTINE.  THE FIRST FOUR LOCATIONS
ARE THE SETPOINT FACTOR REFERENCE, THE

SETPOINT FACTOR, THE FIRST VALVE OFFSET
REF AND VALUE.  THE NEXT FIVE VALUES ARE
THE FOUR VALVE BREAKPOINTS, EXPRESSED
IN ENCODER TICS FROM THE CAM FEATURE OR
END OF INTAKE OF THE OPPOSITE PISTON.
FIVE VALUES ARE REQUIRED BECAUSE THE
FIRST VALVE TO BE ACTUATED IN THE INTAKE
STROKE IS ACTUATED TWICE; ONE-HALF OF
ITS PERCENTAGE IS ACTUATED FIRST AND
THE OTHER HALF LAST, AFTER ALL OTHERS
ARE DONE AT THE END OF THE INTAKE STROKE
THEN THE NEXT FOUR VALUES ARE THE NEW
BREAKPOINTS RECEIVED FROM THE COMM
ROUTINE WHICH ARE PASSED TO THE BREAK-
POINT VALUES ONLY AFTER A GOOD CHECKSUM
IS VERIFIED.

VALVS LOCATIONS 4-8 ARE ALSO USED TO
ACTUATE THE COLUMN SWITCHING, AND THE
'DING-DONG' LED.
}

```
{LENGTH FACTOR REFERENCE
LENGTH FACTOR
FIRST VALVE OFFSET REFERENCE
FIRST VALVE OFFSET (HYDRAULIC LAG)
WORKING SETTING 1
WORKING SETTING 2
WORKING SETTING 3
WORKING SETTING 4
WORKING SETTING 5
RECEIVED VALVE SET 1
RECEIVED VALVE SET 2
RECEIVED VALVE SET 3
RECEIVED VALVE SET 4}
{
VALVE DRIVE CHANGEOVER POINTS
THESE ARE ALSO DETERMINED IN THE COMM
ROUTINE
}
{WORKING BREAKPOINT 1
WORKING BREAKPOINT 2
WORKING BREAKPOINT 3
WORKING BREAKPOINT 4
BREAKPOINT BACKBOARD
RECEIVED BREAKPOINT 1
RECEIVED BREAKPOINT 2
RECEIVED BREAKPOINT 3
RECEIVED BREAKPOINT 4}
{
COMM_DATA IS THE COMM ROUTINE DATA
CACHE.
}
{BYTE COUNT STASH
CHECKSUM STASH
COMMAND BYTE STASH

RECEIVED CHECKSUM STASH
HI PRESS LIM STASH
LO PRESS LIM STASH
REV LEVEL
PUMP LEAK DETECT
OVEN LEAK DETECT
STATUS
OLD INJECT CONTROL VALUE
NEW INJECT CONTROL VALUE
FLOW CHANGE TIMEOUT FLAG
FLOW COMMAND STASH
BOOT PAGE CACHE
PRESSURE SETPOINT
DEGAS ON VALUE
SPEED CAL CACHE
```

```
CAM-ENCODER CAL CACHE
HYDRAULIC LAG CACHE
PRESSURE OFFSET CACHE
DEGAS PUMP OFF POINT
PISTON SIZE CACHE}
{
COMWD IS A DIAGNOSTIC TOOL USED
TO STUDY COMMUNICATIONS WITH THE CPU
}
{
DATA ACQUISITION PORT;
AN INTEGRATED MUX/ADC UNIT
IS ADDRESSED AT 16 LOC'S
BEGINNING WITH 0X2000
}
{
ADC BIT 4 IS DIFFERENTIAL SET
ADC BIT 3 IS BIPOLAR SET
ADC BITS 0-2 ARE ANALOG MUX CHANNEL
CH 0 IS VACUUM DEGAS PRESSURE
CH 1 IS NOT USED
CH 2 PUMP HIGH PRESSURE
CH 3 PUMP LEAK DETECT
CH 4 MOTOR CURRENT
CH 5 REMOTE LEAK DETECT/POT
CH 6 MOTOR VOLTAGE +
CH 7 MOTOR VOLTAGE -
}
{
  PORT DECLARATIONS
  }
{
THIS IS THE BEGINNING OF THE ACTUAL CODE
THE FIRST 1C (28) WORDS ARE INTERRUPT
VECTOR ARRAYS; 7 ARRAYS OF 4 WORDS
EACH.  STARTING WITH ADDRESS 0
THEY ARE IN THE ORDER OF THEIR
PRIORITY; IE RESET INTERRUPT VECTORED
TO ADDRESS 0 HAS THE HIGHEST PRIORITY
AND TIMER INTERRUPT VECTORED TO ADDRESS 18 (24) HAS LOWEST.
}
{
FIRST ARRAY IS RESET VECTOR
ADDRESSES 0-3
INDICATES AN EMULATOR INTERRUPT
MASK VALUE WHICH MUST BE CHANGED BY
SUBTRACTING 8 FROM THAT VALUE TO
PROVIDE PROPER 2105 OPERATION.
```

```
}
        IMASK = 0X00;
{EEEENABLE ONLY EMULATOR INTERRUPTS}
        SET FLAG_OUT;
{       NOP;}
        JUMP  MAIN;      {POWER UP RESET JUMP}
        NOP;
{
SECOND ARRAY IS INT2 DRIVEN
BY THE HARDWARE COUNTER AT
1/2048 THE INSTRUCTION CYCLE RATE
ADDRESSES 4-7
ENABLED BY BIT 5 OF IMASK}
        IMASK = 00;
{ALLOW EEEEMULATOR TO BREAK IN THIS}
        CALL MOTOR_SAMPLE;     {IRQ2}
        DIS SEC_REG;
        RTI;
{
THIRD ARRAY IS SPORT 0 TX
RESERVED FOR EMULATOR
ADDRESSES 8-B
ENABLED BY BIT 4 OF IMASK
MUST ALWAYS BE SET TO ZERO
}
        NOP;     {RESERVED FOR EMULATOR}
        NOP;     {RESERVED FOR EMULATOR}
        NOP;     {RESERVED FOR EMULATOR}
        NOP;     {RESERVED FOR EMULATOR}
{
FOURTH ARRAY IS SPORT 0 RX
RESERVED FOR EMULATOR
ADDRESSES C-F
ENABLED BY BIT 3 OF IMASK
MUST BE SET TO ONE FOR EMULATOR
MUST BE SET TO ZERO FOR 2105
}
        NOP;     {RESERVED FOR EMULATOR}
        NOP;     {RESERVED FOR EMULATOR}
        NOP;     {RESERVED FOR EMULATOR}
        NOP;     {RESERVED FOR EMULATOR}
{
FIFTH ARRAY IS INT1
DRIVEN BY INDEX CHANNEL OF PUMP
ENCODER
ENABLED BY BIT 2 OF IMASK

ADDRESSES 10-13
}
        CALL ENCODER_ROUTINE;      {IRQ1 }
```

```
        NOP;
        RTI;
        NOP;
{
SIXTH ARRAY IS INTO
USED FOR ENCODER INDEX
ENABLED BY BIT 1 OF IMASK
ADDRESSES 14-17
}
        IMASK = 00;
{EEEE DO AS NON-NESTED INTERRUPT}
        CALL INDEX_ROUTINE;
        RTI;                    {IRQ0}
        RTI;
{
SEVENTH ARRAY IS TIMER INTERRUPT
INTERNAL TIMER COUNTING DOWN TO ZERO
ACTUATES THIS
ENABLED BY BIT 0 OF IMASK
ADDRESSES 18-1B
}
        IMASK = 00;
{EEEE DO AS NON-NESTED INTERRUPT}
        CALL TIMER_ROUTINE;     {TIMER}
        RTI;
        NOP;
{
INITIALIZATION ROUTINE
}
{
SET UP SYSTEM CONTROL REGISTERS
}
MAIN:   ICNTL=0X17;
{       IFC = 0X23;}
{CLEAR ALL INT'S EXCEPT EMULATOR}
{THE FOLLOWING SETS UP THE
EMULATOR COMMENT IT OUT TO RUN
2105}
        AX0 = CTRLS_DATA;
        DM(CTRLS_POINT) = AX0;
        AX0 = SYSCNT_DATA;
        DM(SYSCNT_POINT) = AX0;
        AX0 = DMWAIT_DATA;
        DM(DMWAIT_POINT) = AX0;
        AX0 = TPERIOD_DATA;
        DM(TPERIOD_POINT)=AX0;
        AX0 = TSCALE_DATA;
        DM(TSCALE_POINT) = AX0;
{
THE M REGISTERS CHANGE OR MODIFY
THE INDEX BY THE VALUE TO WHICH
THEY ARE SET.  A STANDARD SETUP
```

```
WAS CHOSEN LONG AGO WHICH STILL
SERVES WELL.  M0-M3 GO WITH I0-I3
AND M4-M7 GO WITH I4-I7 EXAMPLES
ARE
DM(I2,M0) DATA MEM ADDRESS=I2;
          CHANGE I2 BY M0 OR 1
          AFTER MEMORY I0
DM(I3,M1) DM ADDRESS = I3 THEN
          CHANGE I3 BY M1 OR -1
DM(I4,M6) DM ADD = I4 THEN CHANGE
          I4 BY M6 OR 0
PM(I5,M4) PM ADD = I5 THEN I5=I5+1
(I4-I7 USED TO ADDRESS BOTH PM AND DM)
PM(I0,M2) NO GOOD;I0-I3 FOR DM ONLY
DM(I0,M4) NG; M4 FOR I4-I7 ONLY
}
        M0 = 1; {INCREMENTAL STEP}
        M1 = -1; {GO BACK 1}
        M2 = 0; {STAY PUT}
        M3 = 2; {DOUBLE STEP}
        M4 = 1; {INCREMENTAL STEP}
        M5 = -1; {GO BACK 1}
        M6 = 0; {STAY PUT}
        M7 = 2; {DOUBLE STEP}
{
LENGTH REGISTERS SET BOUNDARY
FOR ADDRESS REGISTER VALUE.
LOWER END OF BOUNDARY IS
ADDRESS DIVISABLE BY POWER OF
2 EQUAL TO OR GREATER THAN
CURRENT IREG SETTING AND LOWER
THAN SETTING UPPER BOUNDARY IS
AS DESCRIBED ABOVE EXCEPT HIGHER
THAN IREG SETTING.  IF MREG
SETTING CAUSES IREG TO CROSS
BOUNDARY ADDRESS FOLDS BACK TO
OPPOSITE END (EX 01230123)
THE .VAR/CIRC ASSEMBLER COMMAND
SETS THE VARIABLE ADDRESS TO THE
APPROPRIATE POWER OF 2. A LENGTH
OF ZERO DISABLES THE BOUNDARY
FEATURE.
EEEE}
        L1 = 0;{ET LENGTH REGISTER
        L1 = 0X200;}
        L2 = 0; {SET LENGTH REGISTER}
        L3 = 0; {SET LENGTH REGISTER}
        L4 = 0; {SET LENGTH REGISTER}
        L5 = 0; {SET LENGTH REGISTER}
        L6 = 0; {SET LENGTH REGISTER}
        L7 = 0X80; {SET LENGTH REGISTER}
{
IREG INITIALIZATION IS MOSTLY HANDLED
IN THE BODY OF THE CODE.
}
```

```
        I5 = ^VALVS+4; {VALVE BRK INIT}
        I2 = ^VALV_BRK; {VALVE BREAKPOINTS}
{
NOW WE INITIALIZE VARIABLES
USED TO CONTROL PUMP OPERATION
EEEE
        I1=0X3800;
        AR=PASS 0;
        CNTR=0X200;
        DO CLEAR UNTIL CE;
CLEAR:  DM(I1,M0)=AR;
        DM(VDL)=AR;
        L1=0;
        MR=0;
        AX0=0X200;
        DM(MDL)=AX0;
        DM(0X383F)=AX0;
        AX0=INLENGTH;
        DM(0X382E)=AX0;
        AY0=22222;
        DM(0X3855)=AY0;
        AY0=0X5100;
        AX0=0X4F00;
        DM(0X3854)=AX0;
        DM(DEGAS)=AY0;
        DM(GASON)=AX0;
        AY0=174;
        DM(0X380B)=AY0;
        AY0=105;
        DM(0X3830)=AY0;
        AY0=0X6C50;
        DM(0X3800)=AY0;
        AY0=OVERLAP_SPEED;
        DM(STRTSP)=AY0;
        DM(OVLSPD)=AY0;
        AY0=0X1000;
        DM(OSPMUSH)=AY0;
        AY0=0X1400;
        DM(INMUSH)=AY0;
        AY0=63974;
        DM(HYDMUSH)=AY0;
        AY0=0X4800;
        DM(OVLGN)=AY0;
        AY0=350;
        DM(ENDOVL)=AY0;
EEEE}
        AX0=0X0026;
{INITIALIZE STATUS WORD
o POWERUP = 0
o ENCODER NOT FOUND = 1
o FLOW MODE = 1
``` o PAGE VALUE = 2
o ALL OTHERS = 0}
        DM(OX384D)=AX0;
{STORE STATUS}

AX0=2208;
{LOAD REV NUMBER TO AX0}
        DM(OX384A)=AX0;
{REV NUMBER STORED}
{
THE FOLLOWING ROUTINE SETS UP AN OVERLAP
STOP REFERENCE FOR THE STOP SLIDER.
}
{       I6=^COEFF+13;}
{I6 PTG OVERLAP STOP}
{       AY0=PM(I6,M6);}
{LOAD STOP REF AY0}
{       DM(OVST_REF)=AY0;}
{STORE REF}
IDLER:  ENA TIMER;
{START THE TIMER}
{
THE COMM ROUTINE OPERATES THE PARALLEL LINK
TO THE 8188 CPU ACCORDING TO THE PROTOCOL SET
ON 12-91.  THIS ROUTINE IS USED FOR ALL DSP
CODE PAGES BUT DETAILS DIFFER ACCORDING TO
THE FUNCTION OF THE PAGE.  A MEMO LAST
UPDATED ON 1-93 DESCRIBES SOFTWARE DETAILS
}
COMM_ROUTINE:
        IMASK = 00;
{EEEE DISABLE INT'S DDDD}
        I7 = ^COMWD;
{SET I7 TO MONITOR COMM BYTE TRANSFER}
        AR=PASS 0;
{RESET VALUE TO AR}
        DM(OX3844)=AR;
{RESET BYTE COUNT}
        DM(OX3845)=AR;
{RESET CHECKSUM}
        CALL STRTUP;
{GET FIRST BYTE}
        AY1=OX55;
{LOAD HEADER 1 TO AY1}
        AF=SR0 XOR AY1;
{CHECK FIRST WORD}
        IF NE JUMP NAK;
{IF HEADER NO GOOD, JUMP OUT}
        CALL REPLY;
{REPLY TO CPU COMM}
```

```
        AY1=0XAA;
{LOAD HEADER 2 TO AY1}
        AF=SR0 XOR AY1;
{CHECK FIRST WORD }
        IF NE JUMP NAK;
{IF HEADER NO GOOD, JUMP OUT}
        CALL REPLY;
{REPLY TO CPU COMM}
        I6=^COMM;
{I6 PTG PROPORT COMMAND}

AY0=PM(I6,M4);
{PROP CMD AY0 I6 PTG INJ CMD}
        AR=SR0 XOR AY0,AY0=PM(I6,M4);
{SEE IF COMMAND IS PROPORTION
AY0=INJECT I6 PTG FLOW COMMAND}
        IF EQ JUMP PROPO;
{DO PROPORTION IF MATCH}
        AR=SR0 XOR AY0,AY0=PM(I6,M4);
{SEE IF COMMAND IS INJECT
AY0=FLOW I6 PTG PRESSURE LIM COMMAND}
        IF EQ JUMP INJEC;
{DO INJECT CONTROL IF MATCH}
        AR=SR0 XOR AY0,AY0=PM(I6,M4);
{SEE IF COMMAND IS FLOW
AY0=PRESS LIM I6 PTG BOOT COMMAND}
        IF EQ JUMP FLOW;
{DO FLOW CONTROL IF MATCH}
        AR=SR0 XOR AY0,AY0=PM(I6,M4);
{SEE IF COMMAND IS PRESS LIM AY0=CALIB}
        IF EQ JUMP PRESS;
{DO PRESS LIM IF MATCH}
{       AR=SR0 XOR AY0,AY0=PM(I6,M6);}
{SEE IF COMMAND IS CALIB AY0=BOOT}
{       IF EQ JUMP CALIB;}
{DO CALIB IF MATCH}
        AR=SR0 XOR AY0;
{SEE IF COMMAND IS BOOT}
        IF EQ JUMP BOOTC;
{DO BOOT IF MATCH}
        JUMP NAK;
{TERMINATE IF NO MATCH}
{
FOLLOWING IS THE PROPORTION CONTROL
SETPOINT ALGORITHM
}
PROPO:  RESET FLAG_OUT;
{CLEAR INT4}
        CALL REPLY;
{MSG LENGTH MSB'S}
```

A-60293/DJB/MAK     APPENDIX 1     -page 15-

```
        CALL REPLY;
{MSG LNGTH LSB'S}
        CALL REPLY;
{PRIMARY VALVE SET}
        AR=PASS 1,SE=SR0;
{PREPARE TO SET VALVE}
        SR=LSHIFT AR(LO);
{VALVE SETTING IN SR0}
        AR=PASS SR0;
{CHECK FOR STATUS CALL}
        IF GE JUMP OVSTSC;
{JUMP OVER STATUS COMMAND IF POSITIVE}
        CALL REPLY;
{GET CHECKSUM MSB'S}
        CALL CHKSM;
{DO CHECKSUM}

IF NE JUMP NAK;
{JUMP OUT IF NO MATCH}
        JUMP STATUS;
{DO STATUS REPLY}
OVSTSC: SR=LSHIFT SR0 BY -1(LO);
{ADJUST VALVE SETTING TO MATCH CPU
INPUT FORMAT}
        DM(0X3837)=SR0;
{STORE VALVE SETTING}
        MY1=^VALV_BRK+5;
{PRIMARY VALVE BRK MY1}
        CALL WRDAS;
{ASSEMBLE VALVE BREAK WORD}
        I6=^VALVS+1;
{I6 PTG INTAKE STROKE LENGTH FACTOR}
        MY0=DM(I6,M7);
{MY0 FACTOR, I6 PTG SETPOINT OFFSET}
        ENA M_MODE;
{CUT PRIMARY IN HALF}
        MR=SR0*MY0(UU),AY0=DM(I6,M6);
{ADJUSTED SETPOINT MR1, OFFSET AY0}
        AR=MR1+AY0;
{SETPOINT IN AR}
        DM(I0,M2)=AR;
{STORE PRIMARY SETPOINT}
        AR=PASS SR0;
{CHECK VALVE PERCENTAGE}
        AY0=DM(0X3827);
{VALVE SETTING TO AY0}
        IF NE AR=PASS AY0;
{PASS SETTING TO AR IF % NOT 0}
        DM(0X3827)=AR;
{UPDATE VALVE SETTING}
```

```
        CALL REPLY;
{GET NEXT BYTE}
        MY1=^VALV_BRK+6;
{MX1 SET TO 2ND VALVE BRK (I0)}
        MX1=^VALVS+10;
{MY1 SET TO 2ND VALVE SET(I6)}
        CALL PROPV;
{DO A VALVE}
{
FOLLOWING IS THE IMPROVED FUDGE
ROUTINE.  THIS MAKES UP FOR CAM
NONLINEARITIES AND MECHANISM
AND HYDRAULIC EFFECTS.
}
        I6=^VALV_BRK+6;
{I6 PTG 2ND VALVE BREAK}
{       AR=DM(LRFLG);}
{GET L-R FLAG}
        AY0=DM(INFUDGE);
{GET FUDGE FACTOR}
        {AR=PASS AR,}AX0=DM(I6,M5);
{CHECK L-R FLAG NEW BRKPOINT AX0}

{       IF EQ JUMP OVRTL;}
{BIAS LEFT ONLY}
{       AR=DM(ENDOVL);}
{BIAS FUDGE TO AR}
OVRTL:  {AF=AR+AY0,}AY1=DM(I6,M4);
{AF=FUDGE AY1=OLD BRKPOINT}
        AR=AX0-AY0;
{FUDGE NEW BRKPOINT}
        AF=AR-AY1;
{CHECK THAT FUDGED BP IS
GREATER THAN OLD}
        IF LE JUMP OVFDG;
{SKIP OUT IF FUDGED BP IS
LESS THAN OR = OLD BP}
        DM(I6,M6)=AR;
{STORE FUDGED BP}
OVFDG:  MY1=^VALV_BRK+7;
{MX1 SET TO 3RD VALVE BRK}
        MX1=^VALVS+11;
{MY1 SET TO 3RD VALVE SET}
        CALL PROPV;
{DO A VALVE}
        MY1=^VALV_BRK+8;
{MX1 SET TO 4TH VALVE BRK}
        MX1=^VALVS+12;
{MY1 SET TO 4TH VALVE SET}
        CALL PROPV;
```

```
{DO A VALVE}
        CALL CHKSM;
{DO CHECKSUM}
        IF NE JUMP NAK;
{JUMP OUT IF NO MATCH}
{
CPU COMM VERIFIED, IT'S TIME
TO UPDATE THE VALVE SETTINGS
}
        MY0=^VALVS+4;
{MY0 TO WORKING SETTING 1}
        MY1=^VALVS+9;
{MY1 TO RECEIVED VALVE SETTING 1}
        MX0=^VALV_BRK;
{MX0 TO OLD 1ST VALVE BRK}
        MX1=^VALV_BRK+5;
{MX1 TO NEW 1ST VALVE BRK}
        CALL VLVUD;
{UPDATE A VALVE}
        DM(VDL)=AR;
{DRIVE THE PRIMARY VALVE NOW}
        MY0=^VALVS+5;
{MY0 TO WORKING SETTING 2}
        MY1=^VALVS+10;
{MY1 TO RECEIVED 2ND VALVE SET}
        MX0=^VALV_BRK+1;
{MX0 TO OLD 2ND VALVE BRK}
        MX1=^VALV_BRK+6;

{MX1 TO NEW 2ND VALVE BRK}
        CALL VLVUD;
{UPDATE A VALVE}
        MY0=^VALVS+6;
{MY0 TO WORKING SETTING 3}
        MY1=^VALVS+11;
{MY1 = RECEIVED VALVE SET 3}
        MX0=^VALV_BRK+2;
{MX0 TO OLD 3RD VALVE BRK}
        MX1=^VALV_BRK+7;
{MX1 TO NEW 3RD VALVE BRK}
        CALL VLVUD;
{UPDATE A VALVE}
        MY0=^VALVS+7;
{MY0 TO WORKING SETTING 4}
        MY1=^VALVS+12;
{MY1 TO RECEIVED 4TH VALVE SET}
        MX0=^VALV_BRK+3;
{MX0 TO OLD 4TH VALVE BRK}
        MX1=^VALV_BRK+8;
{MX1 TO NEW 4TH VALVE BRK}
```

```
        CALL VLVUD;
{UPDATE A VALVE}
        MY0=^VALVS+8;
{MY0 TO LAST WORKING SETTING}
        MY1=^VALVS+9;
{MY1 TO FIRST RECEIVED VALVE SET}
        MX0=^VALV_BRK;
{MX0 TO OLD 1ST VALVE BRK}
        MX1=^VALV_BRK+5;
{MX1 TO NEW 1ST VALVE BRK}
        CALL VLVUD;
{UPDATE A VALVE}
{
FOLLOWING IS THE STATUS RETURN
MESSAGE
}
STATUS: AX0 = 0;
{CLEAR AX0}
        DM(0X3845)=AX0;
{CLEAR CHECKSUM}
        AR=0X07;
{HEADER TO AR REG}
        CALL DSPTX;
{TRANSMIT HEADER}
        AR=0X15;
{MESSAGE LGTH TO AR}
        CALL DSPTX;
{DO DSP REPLY BOILERPLATE}
        MY1=^FILTER+7;
{FLOW STATUS ADDRESS TO MY1}
        CALL PRSTS;
{SEND STATUS WORD}
        MY1=^CPU_PRES;
{PRESSURE STATUS ADDRESS TO MY1}

CALL PRSTS;
{SEND STATUS WORD}
        MY1=^FILTFLOW+5;
{L POS DIS STATUS ADDRESS TO MY1}
        CALL PRSTS;
{SEND STATUS WORD}
        MY1=^FILTFLOW+4;
{R POS DIS STATUS ADDRESS TO MY1}
        CALL PRSTS;
{SEND STATUS WORD}
        MY1=^COMM_DATA+9;
{MISC STATUS ADDRESS TO MY1}
        CALL PRSTS;
{SEND STATUS WORD}
        MY1=^COMM_DATA+6;
```

```
        {REVISION LEVEL ADDRESS TO MY1}
        CALL PRSTS;
{SEND STATUS WORD}
        MY1=^COMM_DATA+7;
{PUMP LEAK DET VALUE TO MY1}
        CALL PRSTS;
{SEND STATUS WORD}
        MY1=^COMM_DATA+8;
{OVEN LEAK DET VALUE TO MY1}
        CALL PRSTS;
{SEND STATUS WORD}
        MY1=^CPU_VAC;
{VACUUM READING VALUE TO MY1}
        CALL PRSTS;
{SEND STATUS WORD}
        AR=DM(0X3845);
{CHECKSUM TO AR}
        CALL SINOFF;
{SEND CHECKSUM}
{
THE FOLLOWING ROUTINE CHANGES THE STATE OF
THE DINGDONG LED
}
        AY0=0X1000;
        AR=0X23C0;
        CALL SETVLV;
{
SET THE ENCODER INDEX NOT FOUND BIT
}
        AY1=2;
{PREPARE TO SET ENCODER IDX NOT FOUND BIT}
        CALL SETSTS;
{CALL THE ROUTINE}
        JUMP COMM_ROUTINE;
{THAT'S IT FOR PROPORTIONING}
{
INJECT CONTROL ROUTINE FOLLOWS
}
INJEC:  CALL REPLY;
{MSG LGTH MSB'S TO SR0}

CALL REPLY;
{MSG LGTH LSB'S TO SR0}
        CALL REPLY;
{CONTROL BYTE TO SR0}
        DM(0X384F)=SR0;
{NEW INJECT CONTROL WORD TO DM}
        CALL REPLY;
{CHECKSUM MSBS TO SR0}
        CALL CHKSM;
```

```
{DO CHECKSUM}
        IF NE JUMP NAK;
{JUMP OUT IF NO MATCH}
        AR=0X30;
{LOAD ACK VALUE TO AR}
        CALL SINOFF;
{SEND ACK TO CPU}
{
TRANSACTION COMPLETED, NOW UPDATE
THE INJECT CONTROL
}
        MR0=DM(0X384F);
{INJECT CONTROL BYTE TO AR}
        AY0=0XC0;
{PREPARE TO PICK OUT DEGAS BITS}
        AR=MR0 AND AY0;
{PICK OUT DEGAS BITS}
        SR=LSHIFT AR BY 9(LO);
{SHIFT OFF INDICATOR BIT}
        DM(0X384F)=SR0;
{STORE DEGAS CONTROL}
        IF NE JUMP COMM_ROUTINE;
{EXIT ROUTINE IF DEGAS IS SET}
        AY0=0X011D;
{2.5 SEC PULSE TO AY0}
        DM(0X3812)=AY0;
{SET TIMER FOR 2.5 SEC}
        SR=LSHIFT MR0 BY 4(LO);
{POSITION INJECT CONTROL BITS}
        AY0=0XFF0F;
{INJECT CONTROL MASK TO AY0}
        AR=0X2380;
{AND INSTRUCTION}
        CALL SETVLV;
{SET VALVES}
        AY0=SR0;
{INJECT CONTROL MASK TO AY0}
        AR=0X23A0;
{OR INSTRUCTION}
        CALL SETVLV;
{SET VALVES}
        JUMP COMM_ROUTINE;
{THAT'S IT FOR INJECT ROUTINE}
{
THE FLOW CONTROL ROUTINE FOLLOWS
}

FLOW:   CALL REPLY;
{GET MSG LNGTH MSB'S}
        CALL REPLY;
```

```
{GET MSG LNGTH LSB'S}
        MY1=^COMM_DATA+13;
{FLOW COMMAND PTR MY1}
        CALL WRDAS;
{ASSEMBLE FLOW COMMAND WORD}
        CALL REPLY;
{GET CHECKSUM MSB'S}
        CALL CHKSM;
{DO CHECKSUM}
        IF NE JUMP NAK;
{JUMP OUT IF NO MATCH}
        AR=0X10;
{LOAD ACK TO AR}
        DM(NOMOFF)=AR;
{SET NOMINAL OFFSET}
        CALL SINOFF;
{SEND ACK}
{
THE CALIBRATION WILL BE DONE IN THE COMM
ROUTINE, CPU FOR 1 ML PER MINUTE IS 7D0.
1 ML PER MINUTE IS 4D9680 COUNTS.
THIS IS DIVIDED BY 100 BY THE TSCALE
LEAVING A COUNT OF 4D96.  THE ROUTINE
FURTHER DIVIDES THIS BY 10, LEAVING A
VALUE OF 04D9.  THE INVERSION ROUTINE
TAKES THIS AND GIVES US D34.  THE INPUT
MUST THEREFORE BE MULTIPLIED BY 1.B0A4
TO CALIBRATE IT TO THE INVERTED TIMER
VALUE.  FOR 10 MHZ THE MULTIPLIER IS
1.09D0, PROVIDED BY A VALUE OF 84E8
AND THE INHERENT LEFT SHIFT OF 1 WHEN THE
M_MODE IS DISABLED
}
{
CLEAR PRESSURE ALARMS
}
        AY1=0XFF3F;
{PREPARE TO CLEAR PRESS LIM ALARMS}
        CALL CLRSTS;
{EXECUTE CLEAR}
{
THE STATE CHANGE IS ACTUATED BY THE VLVCLR
ROUTINE IN THE MOTOR SAMPLE ROUTINE.  THERE
MAY BE A DELAY OF UP TO 1.5 SEC TO ACTUATE

THE CALIBRATION ROUTINE FOLLOWS.
}
        I0=^COMM_DATA+13;
{I0 PTG RECEIVED FLOW CMND}
{
THIS IS THE PRIME FUNCTION ROUTINE
IF THE CPU SENDS B15=1 ALONG WITH
```

THE FLOW THE DSP DISABLES THE FLOW
CHANGE COUNTER DECREMENT, KEEPING
THE PUMP IN FLOW MODE AND DISABLING
PRESSURE FEEDBACK  V123 ADDS THE
REDUNDANT FLOW REJECT FEATURE  V2150
ADDS SETUP FOR INTELLIGENT INITIALIZATION
AND FLOW MODE OPERATION WITH PRESSURE
LIMITS FUNCTIONAL
}
```
        AY0=DM(FLOW_SET);
{LOAD OLD FLOW VALUE AY0}
        AY1=0X8000;
{SET PRIME MASK TO AY0}
{       DM(ENDSP)=AY1;}
{RESTORE END SPEED TO FLOW MODE VALUE}
{       AR=PASS 0;}
{PREPARE TO CLEAR AI GAIN}
{       DM(AI_GAIN)=AR;}
{CLEAR AI_GAIN}
        AF=AY1-1,MR0=DM(I0,M2);
{FLOW MASK TO AF, FLOW COMMAND AR}
        AR=MR0 XOR AY0,AY0=AY1;
{CHECK FOR FLOW CHANGE FLOW MASK AY1}
        IF EQ JUMP COMM_ROUTINE;
{JUMP OUT IF REDUND FLOW COMMAND
HAS BEEN RECEIVED}
{
SET FLOW MODE STATUS BIT
}
        AY1=0X0004;
{PREPARE TO SET FLOW MODE BIT}
        CALL SETSTS;
{EXECUTE SET BIT}
        DM(FLOW_SET)=MR0;
{UPDATE OLD FLOW COMMAND}
        AR=MR0 AND AY0;
{EXTRACT PRIME BIT}
        DM(PRIME)=AR;
{STORE PRIME BIT}
        MY0=0XC2BD;
{C2BD; CAL VALUE FOR 6.144 MHZ}
        DIS M_MODE;
{MULT WILL LEFT SHIFT BY 1}
        I0=^COMM_DATA+17;
{I0 PTG SPEED CAL}
        AR=MR0 AND AF,MY1=DM(I0,M2);
{SPEED CAL MY1 }
        MR=AR*MY0(UU);
{UPDATED FLOW COMMAND IN MR1}
        SE=EXP MR1(HI);
{NORMALIZE FLOW COMMAND}
        SR=NORM MR1(LO),AY0=SE;
{FLOW CMD NORM SE TO AY0}
        DM(MAG_SPEED)=AY0;
{STORE MAGNITUDE OF SPEED COMMAND}
```

```
        SR=LSHIFT SR0 BY -3(LO);
{OPTIMIZE FOR FLOW RATE OF 1}
        I0 = ^FILTER+15;
{I0 PTG FLOW COMMAND}
        AX0=3;
{GET CORRECTION VALUE FOR SE}
        AR=AX0+AY0;
{SE VALUE IS FIXED}
        DM(FLCORR)=AR;
{STORE FLOW CORRECTION VALUE}
{
THE FOLLOWING ROUTINE UPDATES THE
FLOW COMMAND AND THE NOMINAL SPEED
VALUE  NOMINAL SPEED IS USED TO
START AND STOP THE PUMP.
}
        DM(I0,M3)=SR0,MR=MR1*MY1(UU);
{FLOW COMMAND DM I0 PTG FLOW CTR
NOM SPEED TO MR1}
        SR=LSHIFT SR0 BY -5(LO);
{GET FLOW CHANGE VALUE}
        DM(FLOCH)=SR0;
{STORE FLOW CHANGE VALUE}
{
SET THE 3 FLAGS ASSOC WITH NEW FLOW CMD
FLOW CHANGE FLAG SYNCS SERVO WITH CMD
FLOW CHANGE TIMEOUT SETS UP FOR LO PRESS
LIM DELAY
FC FLAG FORCES SERVO INTO FLOW MODE UNTIL
MOTOR SPEED IS CALIBRATED
}
        SR0=FLOW_TIME;
{CLOCK SET VALUE TO SR0}
        DM(I0,M2)=SR0;
{STORE FLOW CHG SYNCH}
        DM(FCFLAG)=SR0;
{SET FLOW CHANGE FLAG}
        DM(0X3850)=SR0;
{STORE FLO CHG TIMEOUT FLAG}
DNFSC:  DM(0X3804)=MR1;
{STORE NEW NOM SPEED}
        DM(NOM_SPEED)=MR1;
{UPDATE NOMINAL SPEED COMMAND}
{
HERE WE SET UP THE OVERLAP AVERAGING
ROUTINE OVERLAP BREAKPOINTS
}
{
THIS ROUTINE RESTORES THE PRESSURE
SERVO GAIN WHICH MAY BE REDUCED IF
OSCILLATION IS DETECTED
```

```
}       AY0=PRESS_PATH;
{GET NOMINAL PATH GAIN}
        DM(PATH_1)=AY0;

{RESTORE PATH GAIN REFERENCE}
        I6=^COEFF+1;
{I6 PTG PATH GAIN 1}
        PM(I6,M6)=AY0;
{RESTORE PATH GAIN 1}
        MY0=DM(ENDOVL);
{P-POINT PRESET TO MY0}
        MX0=DM(0X3848);
{HI PRESS LIM TO MX0}
        MR=MX0*MY0(UU);
{P-POINT INIT TO MR1}
        DM(0X3818)=MR1;
{STORE LEFT P-POINT}
        DM(0X3817)=MR1;
{STORE RIGHT P-POINT}
        JUMP COMM_ROUTINE;
{FLOW ROUTINE COMPLETED}
PRESS:  CALL REPLY;
{GET MSG LNGTH MSB'S}
        CALL REPLY;
{GET MSG LNGTH LSB'S}
        MY1=^COMM_DATA+04;
{HI PRESS LIM PNTR TO MY1}
        CALL WRDAS;
{ASSEMBLE HI PRESS LIM WORD}
        MY1=^COMM_DATA+05;
{LO PRESS LIM PNTR MY1}
        CALL WRDAS;
{ASSEMBLE LO PRESS LIM WORD}
        MY1=^FILTFLOW+2;
{PRESS OFFSET PTR MY1}
        CALL WRDAS;
{ASSEMBLE PRESS OFFSET WORD}
        CALL REPLY;
{GET CHECKSUM MSB'S}
        CALL CHKSM;
{DO CHECKSUM}
        IF NE JUMP NAK;
{JUMP OUT IF NO MATCH}
        AR=0X60;
{LOAD ACK VALUE TO AR}
        CALL SINOFF;
{SEND ACK}
        I0=^FILTER;
{I0 PTG HI PRESS LIM}
```

```
        I6=^COMM_DATA+04;
{I6 PTG HI PRESS LIM CACHE}
        MX0=DM(I6,M4);
{MX0=NEW PRESS LIM VALUE
I6 PTG LO PRESS LIM CACHE}
        MY0=22718;
{SET MY0 TO PRESS LIM MANTISSA}
        MR=MX0*MY0(UU),MX0=DM(I6,M6);
{MULT SETPOINT BY MANTISSA MX0=LO LIM}
        SR=LSHIFT MR1 BY 3(LO);
{PRESS SETPOINT CONV TO DSP UNITS}
        DM(I0,M0)=SR0,MR=MX0*MY0(UU);
{STORE HI PRESS LIM I0 PTG LO LIM
MULT SETPOINT BY MANTISSA}
        SR=LSHIFT MR1 BY 3(LO);
{PRESS SETPOINT CONV TO DSP UNITS}
        DM(I0,M2)=SR0;
{STORE NEW LO PRESS LIM}
        JUMP COMM_ROUTINE;
{THAT'S IT FOR PRESSURE LIMIT AND
OFFSET COMM ROUTINE}
{
FOLLOWING IS THE FORCE BOOT COMMAND
COMM ROUTINE
}
BOOTC:  CALL REPLY;
{GET MSG LNGTH MSB'S}
        CALL REPLY;
{GET MSG LNGTH LSB'S}
        CALL REPLY;
{GET BOOT PAGE}
        DM(0X3852)=SR0;
{STORE BOOT PAGE}
        CALL REPLY;
{GET CHECKSUM MSB'S}
        CALL CHKSM;
{DO CHECKSUM}
        IF NE JUMP NAK;
{JUMP OUT IF NO MATCH}
        AR=0X03;
{AR = ACK VALUE}
        CALL SINOFF;
{SEND ACK}
        SI=DM(0X3852);
{LOAD BOOT PAGE TO SI}
        SR=LSHIFT SI BY 6(LO);
{SHIFT BOOT PAGE TO BITS 6-8}
        AY0=0X0200;
{SET BOOT FORCE BIT 9}
```

```
        AX0=SYSCNT_DATA;
{MOVE SYSTEM CONTROL DATA TO AX0}
        AY1=0X1E3F;
{SET UP MASK TO CLEAR OLD BOOT PAGE}
        AR=AX0 AND AY1;
{CLEAR OLD BOOT PAGE}
        AF=AR OR AY0;
{BOOT PAGE AND BOOT FORCE TO AF}
        AR=SR0 OR AF;
{SYSTEEEEM CONTROL WORD TO AR
        JUMP COMM_ROUTINE;}
        DM(SYSCNT_POINT)=AR;
{FORCE THE BOOT}
{
IT IS NOT NECESSARY TO RETURN FROM
THIS ROUTINE, SINSE THE PROCESSOR
REBOOTS AT THIS POINT
}
{
COMM SUBROUTINES FOLLOW
}
{
WRDAS IS A BASIC ROUTINE WHICH
RECEIVES AND ASSEMBLES A WORD
FROM 2 BYTES RECEIVED ON THE BUS
MY1 IS THE DATA MEMORY POINTER
FOR THE WORD TO BE ASSEMBLED AND
STORED
}
WRDAS:  CALL REPLY;
{GET WORD MSB'S}
        I0=MY1;
{I0 PTG WORD STASH}
        DM(I0,M2)=SR0;
{STPRE MSB'S}
        CALL REPLY;
{GET WORD LSB}
        I0=MY1;
{I0 PTG MSB STASH}
        SI=DM(I0,M2);
{SI=MSB'S}
        SR=SR OR LSHIFT SI BY 8(LO);
{ASSEMBLE WORD}
        DM(WORD)=SR0;
        DM(I0,M2)=SR0;
{STORE WORD}
        RTS;
{RESUME COMM ROUTINE}
{
```

```
THIS ROUTINE DOES THE PROP VALVE
UPDATE.  SINCE THE ACTUAL VALVE
DRIVE IS ON BITS 0-3 OF THE VDL
THE REST OF THE VDL IS MASKED OFF
TO AVOID CORRUPTING THE OTHER
SOLENOID DRIVE SETTINGS WHEN THE
PROPORTIONING VALVES ARE SET
FOUR ADDRESS VARIABLES ARE SENT
DOWN TO RUN THIS ROUTINE.
MY0 IS OLD VALVE SET ADDRESS
MY1 IS NEW VALVE SET ADDRESS
MX0 IS OLD VALVE BRK ADDRESS
MX1 IS NEW VALVE BRK ADDRESS
}
VLVUD:  I6=MY0;
{I6 PTG OLD VALVE SET}
        I4=MY1;
{I4 PTG NEW VALVE SET}
        I0=MX0;
{I0 PTG OLD VALVE BRK}
        I1=MX1;
{I1 PTG NEW VALVE BRK}

AX0=DM(I1,M2);
        AY0=DM(I6,M6);
{NEW BRKPT AX0, OLD VALVE DRIVE AY0}
        AX1=0XFFF0;
{VALVE DR MASK AX1}
        AF=AX1 AND AY0,AX1=DM(I4,M6);
{CLEAR OLD PROP SET, NEW SET AX1}
        DM(I0,M2)=AX0,AR=AX1 OR AF;
{UPDATE VALVE BRK AR=NEW DRIVE}
        DM(I6,M6)=AR;
{UPDATE VALVE DRIVE}
        RTS;
{CONTINUE VALVE UPDATE}
{
THIS ROUTINE HANDLES THE
PUMP RUN STATUS WORD TRANSMIT
THE TRANSMIT WORD ADDRESS IS
SENT DOWN ON MY1
}
PRSTS:  I0=MY1;
{I0 PTG STATUS WORD}
        SI=DM(I0,M2);
{STATUS WORD TO SI}
        SR=LSHIFT SI BY 8(LO);
{SHIFT MSB'S TO SR1;}
        AR=SR1;
{MSB'S TO AR}
```

```
        CALL DSPTX;
{SEND MSB'S}
        I0=MY1;
{I0 PTG STATUS WORD}
        AR=DM(I0,M2);
{STATUS WORD TO AR}
        CALL DSPTX;
{SEND LSB'S}
        RTS;
{CONTINUE COMM REPLY}
{
THIS ROUTINE ASSEMBLES THE
RECEIVED PROP VALVE 3-BYTE
MESSAGE INTO DSP FORMAT  THE
SETTING ADDRESS IS SENT DOWN
ON MY1 THE SETPOINT ADDRESS
IS SENT DOWN ON MX1
}
PROPV:  AR=PASS 1,SE=SR0;
{PREPARE TO SET VALVE}
        SR=LSHIFT AR(LO);
{STOR CMD BYTE, VALVE SETTING IN SR0}
        SR=LSHIFT SR0 BY -1(LO);
{ADJUST VALVE SETTING TO MATCH CPU
INPUT FORMAT}
        I6=MX1;
{I6 PTG VALVE SETTING}
        AX0=SR0;

DM(I6,M6)=AX0;
{STORE VALVE SETTING}
        CALL WRDAS;
{ASSEMBLE BREAKPOINT WORD}
        I6=^VALVS+1;
{I6 PTG VALVE SETPOINT FACTOR}
        MX0=DM(I0,M1);
        MY0=DM(I6,M4);
{MODIFY I0 PTG PREVIOUS BRKPT
MY0 FACTOR, I6 PTG SETPOINT OFFSET}
        MR=SR0*MY0(UU),AY0=DM(I0,M0);
{ADJUSTED SETPOINT MR1, OFFSET AY0
I0 PTG PRESENT SETPOINT}
        AR=MR1+AY0;
{SETPOINT IN AR}
        DM(I0,M2)=AR;
{STORE PRIMARY BRKPOINT}
        AR=PASS MR1;
{CHECK VALVE PERCENTAGE}
        AY0=DM(0X3837);
{VALVE SETTING TO AY0}
```

```
            IF GT JUMP OV1;
{OVERWRITE SETTING WITH PRIMARY VALUE
IF % = 0}
            I6=MX1;
{I6 PTG VALVE SET}
            DM(I6,M6)=AY0;
{UPDATE VALVE SETTING}
OV1:    CALL REPLY;
{GET NEXT BYTE}
            RTS;
{JUMP OUT OF ROUTINE}
{
THE SINOFF ROUTINE IS COMMON TO ALL
COMM
}
NAK:    AR=0XFF;
{LOAD REPLY TO AR}
            CALL SINOFF;
{SEND REPLY}
            JUMP COMM_ROUTINE;
SINOFF: DM(TXL)=AR;
{SEND REPLY}
            IMASK = 0X27;
{EEEE DO PENDING INTERRUPTS}
STXWT:  IF NOT FLAG_IN JUMP STXWT;
{WAIT FOR CPU REPLY}
            IMASK = 0X00;
{DISABLE INTERRUPTS}
            SI=DM(RXS);
{RESET MASTER STATUS FF}
            RTS;
{BUZZ OFF}
{
DSPTX IS USED TO TRANSMIT
PUMP RUN STATUS.  THE BYTE
IS SENT TO THIS ROUTINE IN
THE AR REGISTER
}
DSPTX:  AY0=DM(0X3845);
{CHECKSUM TO AY0}
            AF=AR+AY0;
{UPDATED CHECKSUM TO AF}
            DM(TXL)=AR;
{MOVE BYTE TO BUSDDDD}
            DM(I7,M4)=AR;
{STORE BYTE TO COMM WORD ARRAY}
            AR=PASS AF;
{MOVE CKSUM TO AR}
            DM(0X3845)=AR;
```

```
{STORE UPDATED CHECKSUM}
        IMASK = 0X27;
{EEEE DO PENDING INTERRUPTS}
TXWT:   IF NOT FLAG_IN JUMP TXWT;
{WAIT FOR CPU REPLY}
        IMASK = 0X00;
{DISABLE INTERRUPTS}
        SI=DM(RXS);
{RESET MASTER STATUS FFDDDD}
        DM(I7,M4)=SI;
{PASS REPLY TO COMM WORD ARRAY}
        RTS;
{CONTINUE COMM ROUTINE}
{
CHKSM IS USED BY ALL COMM ROUTINES
IT HANDLES THE RECEIVED CHECKSUM
WORD.  NO VARIABLES ARE PASSED TO
THIS ROUTINE, REPLY ROUTINE ADDS
UP THE CHECKSUM  THIS ROUTINE GETS
THE CHECKSUM COMPUTED PRIOR TO
RECEIVING THE CHECKSUM
}
CHKSM:  I0=^COMM_DATA+1;
{I0 PTG CHECKSUM STASH}
        DM(I0,M3)=AY0;
{OVERWRITE OLD CKSUM TO STASH
I0 PTG RX CHECKSUM STASH}
        DM(I0,M2)=SR0;
{WRITE RECEIVED CHECKSUM TO DM}
        CALL REPLY;
{GET CHECKSUM LSB'S}
        SI=DM(0X3847);
{RECEIVED CKSUM MSB'S TO SI}
        SR=SR OR LSHIFT SI BY 8(LO);
{ASSEMBLE RECEIVED CHECKSUM}
        AF=SR0 XOR AY0;
{CHECK SUM. AY0 HAS OLD CHECKSUM
FROM BEFORE CHECKSUM WAS RECEIVED}
        RTS;
{CONTINUE COMM ROUTINE  }

{
REPLY IS ANOTHER COMM ROUTINE
WHICH IS COMMON TO ALL COMM
THIS BASIC ROUTINE HANDLES
TASKS WHICH ARE COMMON TO
RECEIVING A BYTE FROM THE BUSS.
}
REPLY:  DIS M_MODE;
{DO LEFT SHIFT IN MULTIPLY}
```

```
        IO=^COMM_DATA;
{IO PTG COUNT STASH}
        AR=PASS 1, AY0=DM(I0,M2);
{PREPARE TO INCREMENT COUNT}
        AR=AR+AY0;
{COUNT INCREMENTED}
        DM(TXL)=AR;
{SEND REPLY TO BYTE}
        DM(I0,M2)=AR;
{STORE INCREMENTED COUNT}
STRTUP: IMASK = 0X27;
{EEEE ENABLE INTERRUPTS}
BYTE:   IF NOT FLAG_IN JUMP BYTE;
{IDLE OR DO PENDING INT'S}
        IMASK = 0X00;
{DISABLE INT'S}
        SI=DM(RXS);
{LOAD RECEIVED COMM WORD TO SI}
        SR=LSHIFT SI BY 8(LO);
{SHIFT OFF MSB}
        SR=LSHIFT SR0 BY -8(LO);
{BYTE IS PREPAREDDDD}
        DM(I7,M4)=SR0;
        IO=^COMM_DATA+1;
{IO PTG CHECKSUM STASH}
        AY0=DM(I0,M2);
{CHECKSUM TO AY0}
        AR=SR0+AY0;
{UPDATE CHECKSUM}
        DM(I0,M2)=AR;
{STORE NEW CHECKSUM      }
        RTS;
{PROCESS COMM BYTE}
{
FOLLOWING IS A ROUTINE TO
PROVIDE STANDALONE OPERATION
FOR EBCS AND IGP-DSP HARDWARE
}
{
THE CALIBRATION WILL BE DONE IN THE COMM
ROUTINE, CPU FOR 1 ML PER MINUTE IS 7D0.
1 ML PER MINUTE IS 4D9680 COUNTS.
THIS IS DIVIDED BY 100 BY THE TSCALE
LEAVING A COUNT OF 4D96. THE ROUTINE
FURTHER DIVIDES THIS BY 10, LEAVING A
VALUE OF 04D9. THE INVERSION ROUTINE
TAKES THIS AND GIVES US D34. THE INPUT
MUST THEREFORE BE MULTIPLIED BY 1.B0A4
TO CALIBRATE IT TO THE INVERTED TIMER
```

VALUE. FOR 10 MHZ THE MULTIPLIER IS
1.09D0, PROVIDED BY A VALUE OF 84E8
AND THE INHERENT LEFT SHIFT OF 1 WHEN THE
M_MODE IS DISABLED
}
{
TIMER ROUTINE CAN BE USED TO PROVIDE
DOUBLE LENGTH TIMER VALUES
}
TIMER_ROUTINE:
        AY0=DM(0X380E);
{LOAD MSB TO AY0 I1 PTG TIM MSB}
        AR=AY0+1;
{INCREMENT MSB}
        DM(0X380E)=AR;
{STORE MSB}
        RTS; {RETURN FROM SUBROUTINE}
{
INDEX ROUTINE SETS EC2 COUNTER TO
FEATURE VALUE
}
INDEX_ROUTINE:
        AY0=DM(0X380B);
{LOAD FEATURE VALUE AY0}
        DM(0X380C)=AY0;
{STORE FEATURE VALUE EC2}
        AY0=DM(0X384D);
{LOAD STATUS TO AY0}
        AY1=0XFFFD;
{CLEAR INDEX NOT FOUND BIT FROM STATUS}
        CALL CLRSTS;
{EXECUTE CLEAR STATUS.}
{
CLEAR THE LEFT-RIGHT FLAG
}
        AR=PASS 0;
{CLEAR AR REG}
        DM(LRFLG)=AR;
{STORE IN L-R FLAG LOCATION}
        RTS; {RETURN FROM SUBROUTINE}
{
THE ENCODER ROUTINE RUNS VELOCITY
CONTROL AND PROPORTIONING
}
ENCODER_ROUTINE:
{
FIND THE INDEX. THIS ROUTINE WILL WORK
EVEN IF THE ENCODER MISSES COUNTS OR HAS
EXTRA COUNTS DUE TO GLITCHES
}
        DIS M_MODE;
{DO LEFT SHIFT IN MULTIPLY}

```
        I0=^FILTER+12;
{I0 PTG EDGE COUNT 2}
        I6=^COEFF+12;
{I6 PTG EC3 MASK}
{
THIS SECTION DOES THE PROPORTIONING
FUNCTION. THE INDEX SETS THE EDGE COUNT
2 TO THE CAM-ENCODER ALIGNMRNT FACTOR VALUE.
WHEN EDGE COUNTER 2 HITS ZERO, EDGE COUNTER 3
IS RESET TO ZERO.  EDGE COUNTER 3 COUNTS
UP; IT IS THE REAL EDGE COUNT, REFERENCED
TO THE CAM, JUST LIKE OUR OLD BAT WING.
THUS THROUGH THE MAGIC OF THE DSP, AN
ORDINARY ENCODER IS TRANSFORMED INTO A
DIONEX BAT WING, ABLE TO LEAP TALL
BUILDINGS AND RUN THE VALVES AND PRESSURE
FEEDBACK AND POSITIVE DISPLACEMENT FLOW
CONTROL. AX0 HAS FEATURE VALUE AND
AY0 HAS INDEX MASK.  I0 IS POINTING
TO THE EDGE COUNT 2.  THE QUESTION IS:
WHY NO EDGE COUNT 1?  WELL, OLDER, LESS
ELEGANT ENCODER ALGORITHMS ONCE HAD 3
EDGE COUNTERS; EC1 WAS FINESSED OUT.
}
        AY0=DM(I0,M0);
{LOAD EDGE COUNT 2 AY0
I0 PTG EDG CNT 3}
        AR=AY0-1,AX1=DM(I0,M1),AY1=PM(I6,M4);
{DEC EDGE CNT 2,AX1=EDG CNT 3
I0 PTG EDG CNT 2 AY1=EC3 MASK
I6 PTG FLOW START TIME}
{
NOW WE UPDATE THE EDGE COUNT 3
THE COUNT IS SET TO ZERO WHEN
THE DOWNCOUNTING EDGE COUNT 2
HITS ZERO.  THE MSB IS MASKED OFF
IN ORDER TO PICK UP THE OPPOSING
CYLINDER INTAKE
}
        DM(I0,M0)=AR;
{UPDATE EDGE COUNT 2, I0 PTG EC 3}
        IF NE AR=PASS AX1;
{UPDATE EDGE COUNT 3}
        AF=AR AND AY1,AX0=DM(I2,M2);
{MASK EC3, AX0=VLV BRKPNT}
        IF NE JUMP OVRST;
{IF EC3 NE 0 JUMP OVER START ROUTINE}
        SET FLAG_OUT;
{SET INT 4 TO CPU AT END OF INTAKE}
        I5=^VALVS+4;
{INITIALIZE VALVE SETTINGS}
        I2=^VALV_BRK;
{INITIALIZE VALVE BREAKPOINTS}
        AR=PASS 0;
{PREPARE TO INITIALIZE AVERAGING}
```

```
        DM(RUNAV)=AR;
{CLEAR SUM LSB'S}
        DM(MSBAV)=AR;
{CLEAR SUM MSB'S}
        {I7=^COMWD;}
OVRST:  AR=AX0-AF,AY0=DM(I5,M6);
{TEST BREAKPOINT, AY0 = VLV VAL}
        IF NE JUMP OVVNC;
{IF BKPT NOT HIT DONT ADVANCE}
        MODIFY (I5,M4);
{ADVANCE VALVE DRIVE SETTING}
        MODIFY (I2,M0);
{ADVANCE BREAKPOINT SETTING}
OVVNC:  DM(VDL)=AY0;
{DRIVE THE VALVES}
        AX0=DM(OVAV_STOP);
{GET OVERLAP AVERAGE STOP POINT}
        AR=AF-AX0;
{SUBTRACT REF FROM EC3}
        IF GT JUMP DOVAV;
{JUMP OUT IF BEYOND OVERLAP}
        IF LT JUMP SOVAV;
{CHECK FOR OVERLAP START IF
NOT YET AT STOP POINT}
        CALL OVAVG;
{DO OVERLAP AVERAGE}
        SI=DM(RUNAV);
{LOAD SI WITH PRESSURE AVERAGE LSB'S}
        SR = LSHIFT SI BY -5(LO);
{SHIFT LSB'S 6 TO THE RIGHT}
        SI=DM(MSBAV);
{GET PRESSURE AVERAGE MSB'S}
        SR=SR OR LSHIFT SI BY -6(HI);
{MOVE MSB'S TO ABUT LSB'S}
{       AY1=DM(ROUND);
        AR=AY1-1;
        DM(ROUND)=AR;
        AY1=0X2;
        AR=AR+AY1;
        IF GE JUMP OVBRK;
        NOP;
OVBRK:  NOP;}
{
FOLLOWING IS A ROUTINE WHICH
SLIDES A FUDGE FACTOR INTO THE
OVERLAP PRESSURE AVERAGE.
UNDOUBTEDLY THIS WILL VARY WITH
HEAD TYPE
}
{       MY0=0X7F80;}
{GET OVERLAP START KNEE FACTOR}
```

```
{       MR=SR0*MY0(UU);}
{MULTIPLY IT BY OVERLAP PRESS AVG}
        DM(PRESSOV)=SR0;
{STORE FUDGED PRESSURE SUM}

{       AR=DM(FCFLAG);}
{GET FLOW CHANGE FLAG}
{       AR=PASS AR;}
{CHECK FLAG}
{       IF EQ JUMP DOVAV; }
{DON'T LEARN IN PRESSURE MODE}
        AY1=DM(LRFLG);
{LEFT-RIGHT FLAG TO AY1}
{
NEXT IS THE LEARNING ALGORITHM REFERENCE
ADJUST ALGORITHM.  THIS COMPARES THE
CROSSOVER PRESSURE TO THE INTAKE PRESSURE
AND INCREMENTS THE REFERENCE IF THE INTAKE
PRESSURE IS HIGHER AND DECREMENTS THE REF
IF THE EXHAUST PRESSURE IS HIGHER.
}
{
FIRST CHECK TO SEE WHICH PISTON WE ARE ON
}
        I0=^FILTFLOW+4;
{I0 PTG FIRST MODIFIER}
        AY0=SR0,AR=PASS AY1;
{STASH PRESSOV CHECK FLOW UPDATE FLAG}
        IF NE JUMP OVSTF;
{JUMP OVER INCREMENT IF FALSE}
        MODIFY(I0,M0);
{PREP TO CLR FLAG INC I0}
{
THEN COMPARE THE INTAKE PRESSURE AVERAGE
WITH THE OVERLAP AVERAGE
}
OVSTF:  SR0=DM(PRESSIN);
{GET INTAKE PRESSURE}
        AR=PASS AF;
{STASH EC3}
        SR1=AR,AF=PASS 1;
{SUBTRACT REFERENCE FROM OVERLAP}
        AR=AY0-SR0,AX1=DM(I0,M2);
{MODIFIER IN AX1,DELTA IN AF}
        IF LE JUMP INCMD;
{INCREMENT MODIFIER IF OVERLAP IS LESS
THAN REFERENCE}
{
HERE WE DECREMENT THE MODIFIER
}
```

```
DECMD:  {AY0=AI_COEFF;}
{GET MODIFIER DELTA VALUE}
        AR=AX1-AF;
{DECREMENT MODIFIER}
        AF=AR-AF;
{CHECK IF BELOW CLAMP}
        IF LT AR=PASS 0;
{EXECUTE CLAMP}
        JUMP EXMOD;
{

HERE WE INCREMENT THE MODIFIER
}
INCMD:  {AY0=DM(AI_GAIN);}
{GET MODIFIER DELTA VALUE}
        AR=AX1+AF;
{INCREMENT MODIFIER}
        AY0=0X4C;
{SET CLAMP}
        AF=AR-AY0;
{CHECK CLAMP}
        IF GT AR=PASS AY0;
{EXECUTE CLAMP}
EXMOD:  DM(I0,M2)=AR,AF=PASS SR1;
{UPDATE MODIFIER}
{
NOW WE EXECUTE THE MODIFIER
}
SOVAV:  I0=^FILTER+13;
{I0 PTG EC3}
        AX0=DM(OVAV_START);
{GET OVLP AVG START POINT}
        AR=AF-AX0;
{SUBTRACT REF FROM EC3}
        IF LE JUMP DOVAV;
{JUMP OUT IF NOT AVG TIME YET}
        CALL OVAVG;
{DO THE OVERLAP AVERAGE}
DOVAV:  AR=AF+1, SR0=PM(I6,M4);
{INC EC3, LOAD OVERLAP START TO SR0
I6 PTG OSC STRT}
        AX0=77;
{OVERLAP STOP AX0}
        DM(I0,M0)=AR,AR=AF-AX0;
{STORE EC3 I0 PTG TIMER MSB
AR=EC3-FLOW STOP}
        IF GT JUMP OVOUT;
{DO TIMER IF COUNT BEYOND OVERLAP}
        IF EQ JUMP OVSTP;
{DO OVERLAP STOP IF EQ STOP}
```

```
        AR=AF-SR0;
{CHECK FOR START POINT}
        IF NE JUMP FLOUT;
{JUMP OUT IF NOT AT START POINT}
        MY0=DM(STRTSP);
{
THE FOLLOWING ROUTINE DOES THE
OVERLAP PERIOD SPEED REDUCTION
}
OVADJ:  MX0=DM(NOM_SPEED);
{NOMINAL SPEED TO SI}
        I0 = ^FILTER+4;
{I0 PTG NOM SPEED COMMAND}
        MR=MX0*MY0(UU);
{NOM SPEED IN MR1}
        DM(I0,M1)=MR1;
{LOAD NOM SPEED COMMAND TO DM
I0 PTG SPEED COMMAND}
        DM(I0,M1)=MR1,AR=PASS 0;
{STORE SPEED COMMAND ADJ PATH GAIN
I0 PTG DEL PRES ERR}
        DM(I0,M2)=AR;
{CLEAR PRES ERR}
        JUMP FLOUT;
{EXIT ROUTINE}
OVSTP:  MY0=0X8000;
{SET SPEED MULTIPLIER FOR NON OVLAP}
        JUMP OVADJ;
{DO OVERLAP SPEED ADJUSTMENT}
OVOUT:  AX0=PM(I6,M7);
{OSC START TO AX0 I6 PTG REF STOP}
        AR=AF-AX0;
{AR=EC3-OSC START}
{
CHECK TO SEE IF WE ARE AT FLOW
TIMER START POINT
}
        IF LT JUMP FLOUT;
{GET OUTTAHERE IF NOT YET TIME}
        IF GT JUMP CKSTP;
{GO TO FLOW STOP ROUTINE IF COUNT GREATER
THAN REF START POINT}
{
FOLLOWING ROUTINE EXECUTES OSCILLATION
DETECT ROUTINE AND THE SETUP OF THE FLOW
CONTROL ALGORITHM
}
{
SET GAIN TO NON-OVERLAP VALUE
```

```
        I6=^COEFF+1;
{I6 PTG PRESS PATH GAIN}
        AR=DM(PATH_1);
{GET NOMINAL PRESS GAIN}
        PM(I6,M6)=AR;
{NOM GAIN TO PRESS GAIN LOC}
{
NOW WE DO THE REFERENCE PRESSURE AVERAGING
ROUTINE SETUP
}
        AY0=0;
{PREPARE TO RESET TIMER COUNT}
        DM(HIFLAG)=AY0;
{RESET OSCILLATION DETECT HI FLAG}
        DM(RUNAV)=AY0;
{CLEAR AVERAGING LSB}
        DM(MSBAV)=AY0;
{CLEAR AVERAGING MSB}
        DM(I0,M2)=AY0,AR=AY0-1;
{RESET TIMER MSB'S; FFFF IN AR}
        DM(TCOUNT_POINT)=AR;

{RESET TIMER LSB'S}
{
THE FOLLOWING ROUTINE EXECUTES THE
POSITIVE DISPLACEMENT FLOW CONTROL. ONCE-
AROUND VELOCITY FLUCTUATIONS IN MOTOR SPEED
ARE COMPENSATED FOR BY SELECTING A PERIOD
WHICH IS A MULTIPLE OF THE ONCE AROUND.
}
{
CHECK THE BALLS TO WALL FLAG AND SET
STATUS
}
        AY1=DM(BALLS_FLAG);
{GET FLAG}
        AR=PASS AY1;
{CHECK FLAG}
        IF GT CALL SETSTS;
{SET BIT IF FLAG POSITIVE}
        IF LT CALL CLRSTS;
{CLEAR BIT IF FLAG NEGATIVE}
        JUMP INTIME;
{DO OSC DET ROUTINE AND EXIT}
CKSTP:  AX0=PM(I6,M4);
{LOAD TIMER STOP POINT TO AX0
I6 PTG TIMER CLAMP}
        AR=AF-AX0;
{CHECK IF TIMER STOP POINT REACHED}
```

```
        IF LT JUMP AVTIME;
{RUN AVTIME IF END POINT NOT REACHED}
        IF GT JUMP FLOUT;
{JUMP OUT IF PAST STOP POINT}
{
NOW WE ARE AT THE COUNT OF 1F0
THIS IS THE END OF THE GOOD PART
OF THE STROKE
}
        AY1=DM(0X3850);
{GET LOW PRESS LIM TIMEOUT FLAG}
DNBAL:  AR=AY1-1;
{DECREMENT FLAG}
        IF LT AR=PASS 0;
{CLAMP FLAG}
        DM(0X3850)=AR;
{STORE FLAG}
        AR=DM(0X3811);
{LOAD FLOW CHANGE FLAG TO AR}
        AR=PASS AR;
{CHECK FLAG}
        IF EQ JUMP DOFLO;
{JUMP OUT IF NO FLAG}
        AR=PASS 0;
{PREPARE TO CLEAR FLAG}
        DM(0X3811)=AR;
{CLEAR FLAG}
        JUMP FLOUT;

{BYE BYE}
DOFLO:  {AR=AI_COEFF;}
{SET AI GAIN}
{       DM(AI_GAIN)=AR;}
{GAIN SET}
        SI=DM(RUNAV);
{LOAD SI WITH PRESSURE AVERAGE LSB'S}
        SR = LSHIFT SI BY -5(LO);
{SHIFT LSB'S 6 TO THE RIGHT}
        SI=DM(MSBAV);
{GET PRESSURE AVERAGE MSB'S}
        SR=SR OR LSHIFT SI BY -6(HI);
{ASSEMBLE AVERAGED INTIME PRESS}
        DM(PRESSIN)=SR0;
{UPDATE PRESSIN}
        AX0=DM(TCOUNT_POINT);
{LOAD CNTR LSB'S TO AX0}
        AR=-AX0,SI=DM(I0,M2);
{NEGATE THE COUNTER LSB'S
CNTR MSB'S TO SI; I0 PTG CNTR MSB'S}
        SR=LSHIFT SI BY -7(HI);
```

A-60293/DJB/MAK  APPENDIX 1  -page 40-

```
{CNTR MSB'S TO BITS 08-14 OF SR0}
        SR = SR OR LSHIFT AR BY -7(LO);
{CNTR LSB'S TO BITS 0-07 OF SR0}
        SE=DM(FLCORR);
{GET FLOW CORRECTION VALUE}
        SR=LSHIFT SR0(LO);
{CORRECT FOR NORMALIZED FLOW}
        AR=PASS SR0,AY0=PM(I6,M4);
{COUNT TO AR, CLAMP TO AY0 I6 PTG NUM MSB}
        IF LT AR=PASS AY0;
{EXECUTE CLAMP}
{
INVERT THE TIMER VALUE
}
        SE = EXP AR(HI), AY0=PM(I6,M4);
{GET DENOM MAGNITUDE, NUM MSB'S TO AY0
I6 PTG NUM LSB'S}
        SR = NORM AR(HI);
{FIRST SIG BIT OF TIMER IN B14}
        AF = PASS AY0, AY0=PM(I6,M4);
{PREPARE NUMERATOR I6 PTG ERROR CLAMP}
        I0 = ^FILTER+15;
{I0 PTG FLOW COMMAND INPUT}
        ASTAT = 0;
{PREPARE TO DIVIDE}
        CNTR = 16;
        DO DIVY UNTIL CE;
DIVY:   DIVQ SR1;
{EXECUTE THE DIVISION}
        SI=AY0;
{PREPARE TO DENORMALIZE}
        SR = LSHIFT SI BY 8(LO);
{GET MSB'S TO SR1}
        AR = SR0, SR = NORM SR1 (HI);

{LSB'S TO AR, DENORMALIZE MSB'S}
        SR = SR OR NORM AR (LO),AY1=DM(I0,M0);
{DENORMALIZE LSB'S; FLOW COMMAND TO AY1
I0 PTG FLOW UPDATE FLAG}
        AR = AY1-SR1,AY0=PM(I6,M4);
{ERROR IN AR REG ERR CLMP TO AY0
I6 PTG FLOW PATH GN}
{
APPLY ERROR CLAMP. AN IMPROVED
ROUTINE IS USED FOR THIS
}
        AF=AR-AY0,MY0=PM(I6,M4);
{CHECK UPPER CLAMP; PATH GAIN TO MY0
I6 PTG PATH GAIN 2}
        IF GT AR=PASS AY0;
```

```
{EXECUTE UPPER CLAMP}
        AF=AR+AY0;
{CHECK LOWER CLAMP}
        IF LT AR=-AY0;
{EXECUTE LOWER CLAMP}
{
NOW WE EXECUTE THE PATH GAIN MULTIPLICATION
}
        DM(RAWERR)=AR;
{STORE RAW ERROR}
        MR=AR*MY0(SU),AX0=DM(I0,M2),MY0=PM(I6,M6);
{MULTIPLIED ERROR IN MR1
PATH GAIN MY0 I6 UPDATE FLAG AX0}
{       MR=MR0*MY0(SU);}
{ERROR IN MR1}
        AF=AX0 XOR AY0;
{UPDATE FLOW UPDATE FLAG}
        MR0=DM(PRES_SET);
{PRESS COMMAND MR0}
        AR=DM(FCFLAG);
{GET FLOW MODE CHANGE FLAG}
        AR=PASS AR;
{CHECK FLAG}
        IF EQ JUMP ORFLO;
{DO PRESS MODE IF FLAG NOT SET}
        MR0=DM(NOMOFF);
{LOAD NOM SPEED OFFSET TO AY0}
        SE=DM(FLCORR);
{LOAD FLOW CORRECT VAL SE}
        AY0=MR1,SR=NORM MR0(LO);
{CORRECT OFFSET, ERROR TO AY0}
        AR=SR0+AY0;
{NEW OFFSET AR}
        SR=ASHIFT AR(LO);
{FIX OFFSET}
        DM(NOMOFF)=SR0;
{STORE OFFSET}
        JUMP OVFLO;
{JUMP OUT, FLOW MODE DONE}
ORFLO:  AR=PASS AF;

{CHECK UPDATE FLAG}
        DM(0X3810)=AR;
{STORE FLAG}
        IF NE JUMP OVFLW;
{JUMP OUT IF FLAG SET}
        AF=PASS MR0;
{PASS OLD SETPOINT TO AF}
        AX0=0XFFFB;
{LOAD CLAMP VALUE TO AX0}
```

```
        SE=EXP MR0 (HI);
{GET MAGNITUDE OF SPEED OR PRESS}
        AY0=SE;
{TRANSFER SE TO AY0}
        AR=AX0-AY0;
{CHECK SE VALUE}
        AR=AY0;
{MOVE EXP VALUE TO AR}
        IF GT AR=PASS AX0;
{EXECUTE CLAMP}
        SE=AR;
{PASS CLAMPED SE VALUE TO SE}
{       SR0=DM(RAWERR);}
{INCREASE PRESSURE MODE FLOW GAIN}
        SR=ASHIFT MR1(LO);
{ADJUST ERROR TO CORRECT LOOP GAIN}
{       MR0=DM(NOM_SPEED);}
{LOAD SPEED TO MR0}
{       AX0=0XFFFC;}
{LOAD CLAMP VALUE TO AX0}
{       CALL GAINC;}
{CORRECT LOOP GAIN FOR SPEED VARY}
{       SR=NORM SR0(LO);}
{ADJUST ERROR TO CORRECT LOOP GAIN}
{       MR0=DM(NOM_SPEED);}
{LOAD SPEED TO MR0}
{       AX0=0XFFFE;}
{LOAD CLAMP VALUE TO AX0}
{       CALL GAINC;}
{CORRECT LOOP GAIN FOR SPEED VARY}
{       SR=NORM SR0(LO);}
{ADJUST ERROR TO CORRECT LOOP GAIN}
{
NOW, A SIMPLE INTEGRATING CONTROL
COMPENSATION IS APPLIED.
}
        AR=SR0+AF,AX1=SR0;
{NEW SETPOINT AR, MOVE ERROR TO AX1}
{
CLAMP THE SERVO OUTPUT
}
        IF LT AR=PASS AF;
{CLAMP IS EXECUTED}
        DM(PRES_SET)=AR;
{UPDATE PRESSURE COMMAND}
{
```

THE NEXT ROUTINE SETS UP A FLOW
CHANGE FLAG. ITS FUNCTION HAS BEEN
GREATLY EXPANDED IN V2150. NOW THIS

```
CONTROLS CHANGEOVER FROM FLOW TO PRESSURE
MODE AND FROM PRESSURE TO FLOW FLAG
KICKS IN IF FLOW ERROR EXCEEDS 1/32 FLOW
}
OVFLO:  AX0=DM(RAWERR);
{GET RAW ERROR}
        AR=DM(FLOCH);
{GET FLOW CHANGE VALUE}
        AF=ABS AX0;
{GET ABSOLUTE VAL ERROR}
        AF=AF-AR;
{SUBTRACT FLOW CHANGE VALUE FROM FLOW}
        IF LE JUMP NOFCH;
{JUMP OUT IF FLOW CHANGE SMALL}
        AY1=4;
{PREPARE TO SET BIT 2}
        CALL SETSTS;
{UPDATE STATUS WORD}
        AY1=FLOW_TIME;
{SET FLAG CLAMP VALUE}
        DM(FCFLAG)=AY1;
{UPDATE FLOW CHANGE FLAG}
NOFCH:  AY1=DM(PRIME);
{GET PRIME FLAG}
        AR=AY1-1;
{CHECK FLAG}
        IF AV JUMP OVFLOW;
{JUMP OUT IF IN PRIME MODE}
        AY1=DM(FCFLAG);
{GET FLAG}
        AR=AY1-1;
{DECREMENT FLAG}
        IF LT JUMP OVFLW;
{JUMP OUT IF ALREADY IN PRESS MODE}
{
THE AI OR ARTIFICIAL INTELLIGENCE ROUTINE
FOLLOWS.  THIS ROUTINE PROVIDES SMOOTH
OVERLAP START TRANSITION AND DIAGNOSTIC
INFORMATION.
5 BREAKPOINTS ARE REQUIRED.
TIC COUNT =  A)  HYD OVERLAP START
             B)  OVERLAP AVERAGE STOP
             C)  HYD AND MECH OVERLAP STOP
             1D0 INTAKE AVERAGE START
             1F0 INTAKE AVERAGE STOP
A) IS ACTUAL POINT AT WHICH CROSSOVER
   SLOWDOWN IS APPLIED.  THIS VARIES
   AND HAS A VALUE FOR EACH PISTON.
B) IS FIXED AT 0X10 PAST A)  AVERAGING
   ROUTINE IS APPLIED 10 TIMES AFTER A)
   MOTOR SPEED IS SLOW AT THIS TIME
C) THE POINT AT WHICH THE SPEED IS INCREASED
```

TO EITHER THE FLOW OR PRESSURE MODE END OF
OVERLAP SPEED VALUE.
1D0-1F0 THE TIMING PERIOD AND THE INTAKE
AVERAGING TIME. TIMING PERIOD PROVIDES
THE FEEDBACK TO SET THE PROPER FLOW RATE
AVERAGING TIME ACQUIRES THE INTAKE AVERAGE
FOR BOTH MODES OF OPERATION AND THE PRESSURE
SETPOINT FOR FLOW MODE OPERATION.
IN OPERATION THIS ALGORITHM
1) AVERAGES THE PRESSURE BETWEEN 1D0 AND 1F0
   AT 1F0
2) AVERAGES THE PRESSURE BETWEEN A) AND B)
   AT B)
3) AT B) AVERAGE 1 IS COMPARED TO AVERAGE 2
4) IF 1 GREATER THAN 2 A) IS DECREMENTED
   IF 2 GREATER THAN 1 A) IS INCREMENTED
   2 A) POINTS ARE STORED, ONE FOR EACH PISTON
5) AT 1F0 POINT A FOR OTHER PISTON IS FED TO
   BREAKPOINT ARRAY FOR PROCESSING
}
OVFLOW: SR0=DM(PRESSIN);
{LOAD NEW PRESSURE READING TO SR0}
        DM(PRES_SET)=SR0;
{PASS INTIME PRESSURE TO SETPOINT}
{
NOW SET UP FOR OVERLAP START MODIFIER
ADJUST ROUTINE
}
        MY0=DM(OSPMUSH);
{SLIDE FACTOR TO MY0}
        MR=SR0*MY0(UU),SR1=AR;
{OVERLAP SPEED CHANGE TO MR1
STASH FCFLAG TO SR1}
        AY1=DM(OVLSPD);
{GET NOMINAL OVERLAP SPEED}
        AR=MR1+AY1,MR0=SR1;
{STRTSP IN AR}
        DM(STRTSP)=AR;
{STORE START SPEED}
        AY0=DM(OLD_PRESSIN);
{GET OLD INTAKE PRESSURE VALUE}
{
THIS IS THE HEART OF THE PISTON PICKER
ALGORITHM. WE WANT TO DELAY THE SWITCHOVER
FROM FLOW TO PRESSURE MODE IF THE PISTON
HAS LOWER PRESSURE
}
        DM(FCFLAG)=MR0;
{STORE FCFLAG}
        AR=PASS MR0;
{CHECK FLAG STASH NEW PRESSIN}
        IF GT JUMP OVPIK;
{JUMP OUT IF FLAG IS SET}
        AR=AY0-SR0,MR1=AY0;
{SUBTRACT NEW AVG FROM OLD AVG

```
L-R AVG TO MR1}
        IF GT AR=PASS 1;
{SET FLAG IF OLD GT NEW}
        IF LE AR=PASS 0;
{CLEAR FLAG OLD LE NEW}
        DM(FCFLAG)=AR;
{STORE FLAG}
        IF GT JUMP OVPIK;
{JUMP OUT IF NOT TIME}
        DM(0X3810)=AR;
{STORE FLOW UPDATE FLAG}
        AY1=0XFFFB;
{PREPARE TO CLEAR FLOW MODE BIT}
        CALL CLRSTS;
{CLEAR THE BIT}
{
THIS SECTION EXECUTES THE
OVERLAP START BREAKPOINT
}
OVPIK:  DM(OLD_PRESSIN)=SR0;
{UPDATE OLD INTAKE PRESSURE}
{
CUT PRESSURE GAIN BY 3 DB
}
OVFLW:  I6=^COEFF+1;
{I6 PTG PATH GAIN}
        MY0=DM(OVLGN);
{GAIN CHANGE FACTOR MY0}
        MX0=DM(PATH_1);
{NOMINAL GAIN MX0}
        MR=MX0*MY0(UU);
{ADJUST GAIN}
        PM(I6,M6)=MR1;
{STORE ADJUSTED GAIN}
        I0=^FILTFLOW+4;
{I0 PTG FIRST MODIFIER}
        AY1=DM(LRFLG);
{GET LEFT-RIGHT FLAG}
        AR=PASS AY1;
{CHECK FLOW UPDATE FLAG}
        AR=1;
{SET FLAG}
        IF EQ JUMP ORINC;
{JUMP OVER INCREMENT IF TRUE}
        AR=PASS 0,AY0=DM(I0,M0);
{INCREMENT INDEX}
ORINC:  DM(LRFLG)=AR;
{STORE FLAG}
        AR=DM(I0,M2);
{MODIFIER TO MR1}
        I6=^COEFF+13;
```

A-60293/DJB/MAK    APPENDIX 1    -page 46-

```
{I6 PTG OVERLAP START}
      PM(I6,M6)=AR;
{OPPOSITE MODIFIER TO OVERLAP START}
      AY0=0X08;

{SET UP OVERLAP START AVG WIDTH}
      AY1=0X018;
{SET UP OVERLAP STOP AVG WIDTH}
      AF=AR-AY0;
{SET UP CLAMP}
      IF LE AR=PASS AY0;
{EXECUTE CLAMP}
      MR1=AR,AR=AR+AY1;
{OVERLAP AVG STOP PT IN AR}
      DM(OVAV_STOP)=AR;
{STORE OVERLAP STOP POINT}
      AR=MR1-AY0;
{OVERLAP AVG STOP PT IN AR}
      DM(OVAV_START)=AR;
{STORE OVERLAP START POINT}
{
THAT'S IT FOR THE NEW ADAPTIVE OVERLAP
ROUTINE
}
{
NOW THAT THE PRESSURE COMMAND HAS BEEN
UPDATED IT IS TIME TO UPDATE THE INTAKE
STROKE LENGTH ADJUSTMENT  FOR OUR FIRST
SHOT THE LENGTH COEFF AND THE OFFSET
WILL BE EQUALLY ADJUSTED.  THE OFFSET
IS IN TICS AND THE COEFFICIENT CONVERTS
THE CPU PERCENTAGE INTO A PERCENTAGE OF
THE HYDRAULIC INTAKE STROKE IN TICS.
GOING THRU THE MATH... NOMINAL PRESSURE
IS 2000 PSI; THAT'S ABOUT 11 K COUNTS.
1000 PSI CHANGES BACK END OF STROKE BY
ABOUT 1.6% ASSUME FRONT END IS ALSO TO
BE MOVED BY 1.6% THEREFORE LENGTH CHANGE
IS 3.2%; THE SUM OF THE CHANGE OF THE
2 ENDS  THE ALGORITHM IS THEREFORE TO
TAKE PRESS READING, SUBTRACT IT FROM
NOMINAL 11 K, STORE DIFFERENCE, MULTIPLY
BY 6248, ADD RESULT TO 32768 AND MULTIPLY
COEFF BY RESULT OF ADDITION WITH M_MODE
DISABLED  OFFSET IS OBTAINED BY MULTIPLYING
THE DIFFERENCE BY -1562 AND AGAIN BY 406
AND ADDING THE RESULT TO THE NOMINAL OFFSET
}
      AY0=11000;
{GET NOMINAL PRESSURE}
```

```
        SR0=DM(PRESSIN);
{GET PRESSIN VALUE}
        AR=AY0-SR0;
{GET PRESSURE DIFFERENCE FROM NOM}
        MY0=DM(INMUSH);
{GET LENGTH CHANGE COEFF}
        MR1=0X8000;
{LOAD MR1 WITH VALUE OF 1}
        I6=^VALVS;
{I6 PTG LENGTH COEFF REFERENCE}

MR=MR+AR*MY0(SU),MY0=DM(I6,M4);
{LENGTH MULTIPLIER IN MR1 REF LENGTH
MY0 I6 PTG WORKING LENGTH COEFF}
        MR=MR1*MY0(UU);
{ADJUSTED LENGTH IN MR1}
{
NOW ADJUST OFFSET  OFFSET MUST BE ADJUSTED
IN OPPOSITE DIRECTION AS LENGTH SINSE
OFFSET MOVES FRONT END OF INTAKE STROKE
WHILE LENGTH MOVES THE BACK END  OPPOSITE
ENDS MOVE IN OPPOSITE DIRECTIONS LENGTHENING
STROKE WHEN PRESSURE IS LOW AND REDUCING
STROKE WHEN PRESSURE IS HIGH
}
        MY0=DM(HYDMUSH);
{OFFSET ADJUST COEFF 1 TO MY0}
        DM(I6,M4)=MR1,MR=AR*MY0(SS);
{STORE NEW LENGTH COEFF OFFSET ADJUST
MULTIPLIER IN MR1 I6 PTG OFFSET REF}
        MY0=0X0300;
{NOMINAL TICS TO MY0}
        MR=MR1*MY0(SS),AY0=DM(I6,M4);
{OFFSET ADJUST COUNT TO MR1 OFFSET
REF AY0 I6 PTG WORKING OFFSET}
{       AR=DM(LRFLG);}
{GET L-R FLAG}
{       AR=PASS AR;}
{CHECK L-R FLAG}
        {IF EQ JUMP OVHTB;}
{BIAS LEFT ONLY}
        {AR=DM(ENDOVL);}
{BIAS FUDGE TO AR}
OVHTB:  AR=MR1+AY0;
{UPDATE OFFSET}
        {AR=AR+AF;}
{FUDGE THE HYDRAULIC LAG}
        DM(I6,M6)=AR;
{STORE UPDATED OFFSET}
{       DM(I7,M4)=AR;
```

```
        I0=^FILTFLOW+1;
        AX0=DM(I0,M2);
        DM(I7,M4)=AX0;
        AY0=DM(COUNT);
        AR=AY0-1;
        DM(COUNT)=AR;
        IF GE JUMP FLOUT;
        NOP}
{
THE AVTIME ROUTINE DOES THE PRESSURE
AVERAGING ROUTINE FOR THE OVERLAP LEARN
ALGORITHM
}
AVTIME: AX0=0X1D0;
{GET PRESSURE AVERAGING START POINT}
        AR=AF-AX0;
```

```
{CHECK IF START POINT IS REACHED}
        IF LT JUMP INTIME;
{SKIP PRESS SUMMING IF NOT REACHED}
        CALL OVAVG;
{DO A SUMMING OPERATION}
{
THE INTIME ROUTINE RUNS THE OSCILLATION
DETECTION ALGORITHM AND SETS THE DEGAS
FLAG
}
INTIME: AR=PASS 0;
{PREPARE TO CLEAR DEGAS FLAG}
        DM(VAC_FLAG)=AR;
{FLAG CLEARED}
        I6=^COEFF+1;
{I6 PTG PRESS PATH GAIN}
        SR0=DM(NOM_SPEED);
{GET NOMINAL SPEED}
        MY0=0X4000;
{GET CLAMP MULTIPLIER}
        MR=SR0*MY0(UU);
{SET CLAMP RANGE FOR OSC DETECT}
        AY0=800;
{SET CLAMP CLAMP VALUE}
        AF=MR1-AY0,AR=MR1;
{SUB CLAMP FROM VALUE CLAMP TO AR}
        IF GT AR=PASS AY0;
{EXECUTE CLAMP}
        AY0=DM(0X3803);
{SPEED COMMAND TO AY0}
        AF=PASS SR0,MR0=AR;
{NOM SPEED AF CLAMPED CLAMP SR0}
        AR=DM(HIFLAG);
```

```
        {PREPARE TO CHECK FLAG}
            AR=PASS AR;
        {CHECK FLAG}
            IF NE JUMP LOOSC;
        {CHECK FOR LOW CONDITION IF SET}
            AR=MR0+AF;
        {SUM CLAMP AND NOM SPEED}
            AR=AR-AY0;
        {SUB SPEED CMD FROM SUM}
            IF GE JUMP FLOUT;
        {JUMP OUT IF OK}
            DM(HIFLAG)=AR;
        {SET FLAG}
            JUMP FLOUT;
        {JUMP OUT AFTER SETTING FLAG}
        {
        THIS ROUTINE REQUIRES A HIGH THEN A LOW
        IN ORDER TO TRIP.  THIS PREVENTS FALSE
        TRIPPING AND ALLOWS MORE SENSITIVITY
        }
        LOOSC:  AR=AF-MR0;
        {SUBTRACT CLAMP FROM NOM SPEED}

AF=AR-AY0;
        {SUBTRACT SPEED CMD FROM CLAMP}
            IF LE JUMP FLOUT;
        {JUMP OUT IF OK}
        OSC:    AR=PASS 0,SI=PM(I6,M6);
        {GET PATH GAIN}
            SR=LSHIFT SI BY -5(LO);
        {REDUCE THE GAIN}
            AY0=PM(I6,M6);
        {LOAD GAIN TO AY0}
            DM(HIFLAG)=AR;
        {RESET FLAG}
            AR=AY0-SR0;
        {REDUCE THE GAIN}
            PM(I6,M6)=AR;
        {STORE REDUCED GAIN}
            DM(PATH_1)=AR;
        FLOUT:  RTS;
        {
        THIS ROUTINE SUMS THE PRESSURE READINGS
        AT EACH ENCODER TIC
        }
        OVAVG:  AY1=DM(RUNAV);
        {LOAD LSB'S TO AY1}
            AR=PASS AF;
        {MOVE DATA OUT OF AF REG}
            MR1=AR;
```

```
{MOVE AF DATA TO MR1}
        AR=DM(0X3816);
{CURRENT PRESSURE TO AR
        DM(I7,M4)=AR;}
        AF=AR+AY1;
{ADD PRESS READING TO SUM}
        AY1=DM(MSBAV);
{LOAD MSB'S TO AY1}
        AR=AY1;
{INITIALIZE AR FOR MSB INCREMENT}
        IF AV AR=AY1+1;
{INCREMENT MSB IF LSB O'FLOWS}
        DM(MSBAV)=AR;
{STORE UPDATED MSB}
        AX1=0X7FFF;
{GET A MASK}
        AR=AX1 AND AF;
{STRIP SIGN BIT OFF LSB}
        DM(RUNAV)=AR;
{STORE LSB}
        AF=PASS MR1;
{RESTORE AF}
        RTS;
{SAY BYE-BYE}
CLRSTS: AX1=DM(0X384D);
{GET STATUS WORD}
        AR=AX1 AND AY1;
{CLEAR FLOW MODE STATUS BIT}

DM(0X384D)=AR;
{STORE STATUS}
        RTS;
{RETURN TO MAIN ROUTINE}
SETSTS: AX1=DM(0X384D);
{GET STATUS WORD}
        AR=AX1 OR AY1;
{SET STATUS BIT}
        DM(0X384D)=AR;
{UPDATE STATUS WORD}
        RTS;
{RETURN TO MAIN ROUTINE}
{
THE SET VALVE ROUTINE DRIVES THE
OUTPUT DEVICES ON THE VALVE DRIVE
LATCH.  THE ROUTINE REQUIRES THE
INSTRUCTION TYPE TO BE PASSED ON THE
AR AND THE MASK ON THE AY0 REGISTERS
}
SETVLV: SR1=I4;
{STORE I4 VALUE}
```

```
{0X02D1 FOR 2105}
        I4=0X02D1;
{POINT TO INSTRUCTION TYPEEEE}
        AX0=0X000F;
{SET AR TO DO PX VALUE}
        PX=AX0;
{SET VALUE OF PX REGISTER}
        PM(I4,M6)=AR;
{SET INSTRUCTION TYPE}
        I4=^VALVS+4;
{I6 PTG SOLENOID VALVE SET}
        CNTR=5;
{SET COUNTER TO DO 5 VALVE SETS}
        DO INSET UNTIL CE;
{SET DO LOOP TO EXECUTE INJECT SET}
        AX0=DM(I4,M6);
{VLV DRV VALU AX0}
        AR=AX0 AND AY0;
{DEFAULT INSTRUCTION TYPE}
INSET:  DM(I4,M4)=AR;
{STOR UPDAT INJ I3 PTG NEXT VSET}
DONST:  I4=SR1;
{RESTORE I4 VALUE}
        AX0=DM(I5,M6);
{GET CURRENT VALVE DRIVE VALUE}
        DM(VDL)=AX0;
{DRIVE INJECT VALVE}
        RTS;
{EXIT ROUTINE}
        RTS;
{
THE MOTOR_SAMPLE ROUTINE RUNS THE
PRESSURE SERVO AND THE MOTOR VELOCITY
SERVO.  THE PRESSURE SERVO UPDATES
```

AT 1/32 THE FREQUENCY OF THE MOTOR
VELOCITY SERVO
}
MOTOR_SAMPLE:
{
THE FOLLOWING ROUTINE GETS THE PRESSURE
SAMPLE AND FILTERS IT AND CLOSES A SERVO
LOOP AROUND IT.  THIS SERVO ACTUATES THE
SPEED SERVO.
}
        ENA SEC_REG;
{USE SECONDARY REGS FOR THIS ROUTINE}
{
THE FIRST READING IS NOT USED
BUT FOR GOOD STYLE IT IS SET UP

```
TO ALWAYS BE PUMP LEAK READING
}
        AR=DM(0X2002);
{MUX DATA SETUP FOR MAX180}
        AR=DM(0X802);
{STROBE PRESS AR=PUMP LEAK}
        SE=4;
{SET SHIFT EXP FOR ADC CONDITIONING}
        I4=^COEFF;
{I4 PTG ERROR CLAMP}
        CNTR=MOTWAT;
{SET COUNTER FOR MOTOR CONVERT}
{
MOTWAT IS A LONGER DELAY TO PROVIDE FOR
SETTLING OF MOTOR VOLTAGE
}
        DO WAIT3 UNTIL CE;
WAIT3:  SI=DM(0X200E);
{MUX DATA SETUP FOR MAX180}
        SI=DM(0X80E);
{PRESS TO SI STROBE MOT}
{
THE STROBE FOR THE MOTOR BACK EMF
HAPPENED ON ABOVE INSTRUCTION
}
        CNTR=ADCONV;
{SET UP COUNTER FOR NEXT CONVERT}
        DO WAIT63 UNTIL CE;
WAIT63: I1=^FILTER+7;
{I1 PTG SPEED FB}
        AR=DM(0X2003);
{MUX DATA SETUP FOR MAX 180}
        AR=DM(0X803);
{TAKE MOTOR STROBE PUMP LEAK}
{
THE THIRD AND FINAL VOLTAGE SAMPLE
IN THIS ROUTINE  NOW PREPARE THE
DATA FOR DSP ROUTINES
}.
        SR=LSHIFT AR(HI);

{FLAG CLEARED I1 PTG SPEED FB
PREP MOT VOLT READING TO SR1}
{
THE MOTOR VOLTAGE IS A BIPOLAR
READING SO THERE IS NO CLEARING
OF THE SIGN BIT AS IN ALL OTHER
DATA PREP
}
        DM(I1,M2)=SR1,SR=LSHIFT SI(HI);
```

```
{STORE MOT VOLT PREP PRESS READ TO SR1}
        SR=LSHIFT SR1 BY -1(HI);
{PREPARE PRESSURE READING}
        {DM(I7,M4)=SR1;}
{
PRESSURE READINGS ARE PASSED THROUGH
AN EXPONENTIAL FILTER
}
        SE=-3;
{SET UP FOR EXPONENTIAL FILTER}
        I3=^FILTFLOW+1;
{I3 PTG FILTERED PRESS VAL}
        SR=LSHIFT SR1(HI),AR=DM(I3,M1);
{SR1=NEW PRESS SAMPLE AR=OLD OUT
I3 PTG COUNT}
        AY1=SR1,SR=LSHIFT AR(LO);
{NEW SAMPLE AY1 OLD SAMPLE SR0}
        AF=AR+AY1,AY0=DM(I3,M3);
{AF=DEL PRESS - SHFTD DEL PRESS AY0=COUNT
I3 PTG PRESS OFFSET VAL}
        AR=AF-SR0,AY1=DM(I3,M1);
{SUBTRACT OLD SAMPLE NEW OUTPUT TO AR
OFFSET AY1 I3 PTG FILT PRESS VAL}
        DM(I3,M3)=AR,AR=AR-AY1;
{STOR NEW FILT PRESS AR=PRESS-OFFSET
I3 PTG CORR PRES VAL}
        SR0=AR;
{PASS NEW SAMPLE TO SR0}
        SE=-6;
{SET SE FOR CPU PRESSURE}
        AY1=DM(CPU_PRES);
{OLD OUTPUT TO AY1}
        SR=ASHIFT SR0(LO),SI=AY1;
{NEW SHFT SR0 OLD OUT SI
I3 PTG OFFSET VALUE}
        DM(I3,M1)=AR;AF=SR0+AY1;
{STORE DSP CORRECTED READING
DO FIRST FILTER OPERATION}
        SR=ASHIFT SI(LO);
{OLD SHFT SR0}
        AR=AF-SR0;
{AR HAS THE NEW VALUE NOW}
        DM(CPU_PRES)=AR;
{UPDATE CPU PRESSURE}
        AR=AY0-1;
{DEC COUNT}

{
THE COUNT IS FOR THE PRESSURE
SAMPLE UPDATE AND THE REAL-TIME
```

```
CLOCK
}
        IF LE JUMP DOSMP;
{DO SAMPLE IF COUNT IS EXPIRED}
        DM(0X3813)=AR;
{STORE COUNT}
        I1=^FILTER+3;
{I1 PTG SPEED COMMAND}
        MR1=DM(I1,M2);
{LOAD SPEED COMMAND MR1}
        I4 =^COEFF+5;
{I4 PTG SPEED ERR CLAMP}
        JUMP SPSMP;
{JUMP TO DO SPEED UPDATE}
{
FOLLOWING IS THE PRESSURE SAMPLE ROUTINE
FIRST THE AUXILLIARY VOLTAGE SAMPLES
ARE TAKEN.  THESE ARE THE LEAK DETECT
VOLTAGE VALUES AND THE VACUUM DEGAS
PRESSURE TRANSDUCER READING.
}
DOSMP:  CNTR=ADCONV;
{PREPARE TO GET MOTOR VOLTAGE}
        DO WAITLEK UNTIL CE;
WAITLEK:SI=DM(0X2005);
{MUX DATA SETUP FOR MAX 180}
        SI=DM(0X805);
{PUMP LEAK TO SI STROBE OVEN LEAK}
        CNTR=ADCONV;
{SET UP COUNTER FOR NEXT CONVERT}
        DO WAITVAC UNTIL CE;
WAITVAC:I1=^COMM_DATA+7;
{I1 PTG PUMP LEAK DET}
        AR=DM(0X2000);
{MUX DATA SETUP FOR MAX 180}
        AR=DM(0X800);
{OVEN LEAK TO AR STROBE DEGAS}
        SE=4;
{SET SHIFT EXPONENTIAL}
        SR=LSHIFT SI(LO);
{SHIFT PUMP LEAK}
        SR=LSHIFT SR0 BY -1(LO);
{CLEAR SIGN BIT OFF PUMP LEAK}
        DM(I1,M0)=SR0,SR=LSHIFT AR(LO);
{STORE PUMP LEAK SHIFT OVEN LEAK
I1 PTG OVEN LEAK}
        SR=LSHIFT SR0 BY -1(LO);
{CLEAR SIGN BIT OFF OVEN LEAK}
        CNTR=ADCONV;
{PREPARE TO GET DEGAS STROBE}
        DO WTVACU UNTIL CE;
WTVACU: AX0=0X08;
```

```
{PREPARE TO RESET COUNT VALUE}
        DM(0X3813)=AX0;
{COUNT VALUE STORED}
        SI=DM(0X2003);
{MUX DATA SETUP FOR MAX 180}
        SI=DM(0X803);
{DEGAS TO SI STROBE PUMP LEAK}
        DM(I1,M2)=SR0,SR=LSHIFT SI(LO);
{SHIFT BAD STUFF OUT STOR OVN LK}
        SR=LSHIFT SR0 BY -1(LO);
{SHIFT SIGN BIT DOWN}
        DM(CPU_VAC)=SR0;
{STORE CPU DEGAS READING}
        I3=^FILTFLOW+3;
{I3 PTG CORRECTED PRESSURE}
        AR=PASS 0,MR0=DM(I3,M2);
{CLEAR AR REG PRESS FEEDBACK MR0}
{
NEXT IS THE REAL-TIME CLOCK.
LSB'S ARE SET IN THE INJECT
COMM.
}
        AY1=DM(0X3812);
{CLOCK VALUE TO AY1}
        AR=AY1-1;
{DEC CLOCK VALUE}
        IF GT JUMP BYCNT;
{DO NOT CLEAR INJECT IF POS}
        AY0=0XFF0F;
{INJECT CONTROL MASK TO AY0}
        AR=0X2380;
{AND INSTRUCTION}
        CALL SETVLV;
{SET VALVES}
        AR=PASS 0;
{SET VALUE OF AR}
BYCNT:  DM(0X3812)=AR;
{STORE CLOCK VALUE}
        AX1=DM(CPU_PRES);
{LOAD CORR PRESS}
        I3=^FILTER;
{I3 PTG HI LIM}
        AF=PASS AX1,AX1=DM(I3,M0);
{HI LIM AX1 I3 PTG LO LIM}
{
WE CLAMP TO ZERO SO THAT THE
LOW PRESSURE LIMIT WILL NOT
TRIP IF A VALUE OF ZERO IS SET
BY THE CPU
}
        IF LE AF=PASS 0;
{CLAMP PRESSURE READING}
        AR=AF-AX1,AX1=DM(I3,M2);
{CHECK HI LIM AY1=LO LIM}
        AY1=0X40;
```

```
{SET HI PRESS TRIP BIT}
        IF GT JUMP PRSTA;
{UPDATE STATUS IF LIMIT IS TRIPPED}
        AR=AX1-AF;
{CHECK LO LIMIT}
        AX1=DM(0X3850);
{AX1=FLOW CHANGE FLAG}
        IF LE JUMP DNSTA;
{JUMP OUT IF LO LIM OK}
        AR=PASS AX1;
{CHECK TIME IF LO LIM TRIPPED}
        IF GT JUMP DNSTA;
{JUMP OUT IF TIMER NOT ZERO}
        AY1=0X80;
{SET LO PRESS LIM STATUS}
{
THE PRSTA ROUTINE SETS THE STATUS
BITS FOR HI AND LO PRESS LIM TRIP
IF FLOW IS ZERO OR IF COLUMN SWITCHING
IS ACTIVE THE ROUTINE IS DISABLED
}
PRSTA:  AX1=0XF0;
{SET COLUMN DRIVE MASK}
        I3=^VALVS+4;
{PREP TO GET COLUMN DRIVE STATUS}
        AF=PASS AX1,AX1=DM(I3,M2);
{COLUMN STATUS TO AR}
        I3=^FILTER+15;
{I3 PTG FLOW COMMAND}
        AR=AX1 AND AF,AX1=DM(I3,M2);
{CHECK COLUMN STATUS AX1=FLOW COMMAND}
        IF NE JUMP DNSTA;
{JUMP OUT IF COLUMN ACTIVE}
        AR=PASS AX1;
{CHECK FLOW COMMAND}
        IF EQ JUMP DNSTA;
{JUMP OUT IF FLOW IS ZERO}
{
NOW SET PRESS LIM TRIPPED STATUS
STATUS IS PASSED ON AX1
}
        CALL SETSTS;
{UPDATE STATUS}
DNSTA:  AY0=DM(PRES_SET);
{PRESS SETPOINT AY0}
        AR=AY0-MR0, AY0=PM(I4,M4);
{ERROR IN AR; ERROR CLAMP IN AY0
I4 PTG ERROR COEFF}
{
APPLY ERROR CLAMP.  AN IMPROVED
ROUTINE IS USED FOR THIS
```

```
        I1=^FILTER+2;
{I1 PTG DEL ERR VALUE}
NERR:   AF=AR-AY0,MX0=DM(I1,M2);
```

```
{CHECK UPPER CLAMP DEL ERR MX0}
        IF GT AR = PASS AY0;
{EXECUTE UPPER CLAMP}
        AF = AR+AY0,MY0=PM(I4,M4);
{CHECK LOWER CLAMP PATH GAIN TO MY0
I4 PTG ERR COEFF}
        IF LT AR = -AY0;
{EXECUTE LOWER CLAMP}
{
NOW WE EXECUTE THE PATH GAIN MULTIPLICATION
}
        DIS M_MODE;
{ONE LEFT SHIFT AFTER MULTIPLY}
        SR=ASHIFT AR BY 2(LO);
{SHIFT ERROR LEFT 2}
        MR=SR0*MY0(SU),MY0=PM(I4,M4);
{MULTIPLIED ERROR IN MR1 ERR COEFF
TO MY0 I4 PTG DEL ERR COEFF}
{
THE SERVO COMPENSATION IS PERFORMED
OUR SAMPLE RATE IS 100 HZ
THE FREQUENCY OF INTEREST IS 1 HZ; THIS
SETS THE OMEGA AT 6.  THAT IS SO FAR
FROM THE SAMPLING FREQUENCY THAT DAVE'S
QUICKIE CAN BE APPLIED:  GET THE RATIO OF
6 OVER 600; MULTIPLY BY 32K, GIVES US 320
OR 140 HEX.  START WITH 8000 HEX FOR THE THREE
COEFF'S, ADD 140 TO THE ERR COEFF, SUBTRACT 140
FROM THE DEL ERR COEFF AND LEAVE THE DEL OUTPUT
COEFF ALONE.  SO WE GET 8140, 7EC0 AND 8000
FOR OUR COEFFICIENT VALUES
}
        DM(I1,M2)=MR1;
{OVERWRITE DEL ERR VALUE IN DM}
        MR=MR1*MY0(SU),MY0=PM(I4,M4),AX0=DM(I1,M0);
{MULT ERR BY ERR COEFF RES IN MR1
SET UP MULT TO MULT DEL ERR BY ITS COEFF,
ERROR TO AX0
I1 POINTING TO DEL OUT VALUE
I4 POINTING TO DEL OUTPUT COEFF}
        MR=MR-MX0*MY0(SU),MY0=PM(I4,M4),MX0=DM(I1,M2);
{SUBTRACT DEL ERR * DEL ERR COEFF
FROM FIRST RESULT; VALUE IN MR1
LOAD DEL OUTPUT COEFF TO MY0
I4 PTG TO COMP INPUT COEFF
```

LOAD DEL OUTPUT VALUE TO MX0}
        MR=MR+MX0*MY0(UU);
{ADD DEL OUT * DEL OUT COEFF
TO SECOND RESULT}
{
THE FOLLOWING ROUTINE STOPS THE PUMP IF
STATUS INDICATES THAT PUMP HAS JUST
POWERED UP OR A PRESSURE LIMIT HAS TRIPPED
THESE BITS ARE CLEARED IN THE COMM ROUTINE
}

SPSMP:  I3=^COMM_DATA+9;
{I3 PTG STATUS WORD}
        AY1=DM(I3,M2);
{LOAD STATUS TO AY1}
        AX1=0X00C0;
{SEND A MASK TO AX1}
        AR=AX1 AND AY1;
{CHECK STATUS,SPEED COMMAND TO MR1}
        IF NE JUMP STOP1;
{STOP PUMP IF STATUS SET}
{
NOW WE RESUME MOTOR CONTROL
BY RUNNING THE VELOCITY SERVO
ROUTINE
}
{
THIS ROUTINE CHECKS FOR STOP CONDITION
}
        AR=DM(NOM_SPEED);
{CHECK NOM SPEED}
        AR=PASS AR;
{TEST SPEED}
        IF EQ JUMP STOP;
{STOP MOTOR IF ZERO}
{
THIS ROUTINE RUNS FLOW MODE
}
{
FIRST CHECK FLOW CHANGE FLAG
}
        AR=DM(FCFLAG);
{GET PRESS CH FLAG}
        AR=PASS AR;
{CHECK FLAG}
        IF EQ JUMP PUPDAT;
{JUMP OUT IF FLAG CLEAR}
{
NOW EXECUTE FLOW MODE.
THE NOM SPEED GETS PASSED TO THE

```
                SPEED COMMAND, FORCING THE MOTOR
                TO RUN AT CONSTANT SPEED
                }
        FLOMD:  MODIFY (I1,M0);
        {I1 PTG NOM SPEED}
                MR1=DM(I1,M1);
        {NOM SPEED VALUE AR I1 PTG SP CMD}
        PUPDAT: SE=EXP MR1(HI);
        {SEE HOW BIG DELAYED OUTPUT IS}
                AY0=SE;
        {PASS SE VALUE TO AY0}
                AF=PASS AY0,AR=MR1;
        {CHECK SE VALUE}
                AY0=DM(NOMOFF);
        {GET NOMINAL OFFSET VALUE}
                IF NE JUMP SMALL;

{THE DAMN THING IS SMALL}
                AX0=0X7FFF;
        {LOAD CLAMP VALUE TO AX0}
                AR=PASS AR;
        {CHECK SETPOINT}
                IF LT AR=PASS AX0;
        {EXECUTE CLAMP}
                DM(I1,M2)=AR,AR=AR+AY0;
        {SUM OFFSET AND SETPOINT}
                IF LT AR=PASS AX0;
        {EXECUTE CLAMP}
                JUMP PRDAT;
        {JUMP OUT}
        SMALL:  AY1=13;
        {LOAD CLAMP VALUE TO AY1}
                AF=AR-AY1;
        {CHECK SETPOINT}
                IF LT AR=PASS AY1;
        {EXECUTE CLAMP}
                DM(I1,M2)=AR,AR=AR+AY0;
        {STORE SPEED CMD SUM OFFST & SETPT}
                IF LT AR=PASS AY1;
        {EXECUTE CLAMP}
        PRDAT:  I1=^FILTER+7;
        {I1 PTG MOT FEEDBACK CACHE}
                AF=PASS AR,SR0=DM(I1,M0);
        {MOT VOLT READING SR0 SPEED COMMAND
        AF I1 PTG DEL SPEED ERR}
                AR=AF-SR0, AY0=PM(I4,M4);
        {ERROR IN AR; ERROR CLAMP IN AY0
        I4 PTG ERROR COEFF}
        {
        APPLY ERROR CLAMP. AN IMPROVED
```

```
ROUTINE IS USED FOR THIS
}
        AF = AR-AY0,AX0=DM(I1,M0);
{CHECK UPPER CLAMP; LOAD DEL ERR TO AX0
I1 PTG DEL OUTPUT VAL}
        DM(DEL_ERR)=AX0;
        IF GT AR = PASS AY0;
{EXECUTE UPPER CLAMP}
        AF = AR+AY0,MY0=PM(I4,M4);
{CHECK LOWER CLAMP PATH GAIN TO MY0
I4 PTG DEL ERR COEFF}
        IF LT AR = -AY0;
{EXECUTE LOWER CLAMP}
{
NOW WE EXECUTE THE PATH GAIN MULTIPLICATION
}
        ENA M_MODE;
{PROVIDE FOR UNSIGNED MULTIPLY}
        MR=AR*MY0(SU),MY0=PM(I4,M4);
{MULTIPLIED ERROR IN MR0 ERR COEFF
TO MY0 I4 PTG DEL ERR COEFF}
{
```

```
THE SERVO COMPENSATION IS PERFORMED
OUR SAMPLE RATE IS 750 KHZ
THE FREQUENCY OF INTEREST IS 30 HZ; THIS
SETS THE OMEGA AT 200. THAT IS SO FAR
FROM THE SAMPLING FREQUENCY THAT DAVE'S
QUICKIE CAN BE APPLIED: GET THE RATIO OF
200 OVER 1.5 K. THE THIRD COEFF IS 8000
HEX. ADD RATIO TO 1 AND MULTIPLY
BY THIRD COEFF (8000) TO GET THE FIRST.
THE SECOND IS OBTAINED BY SUBT RATIO FROM 1
AND MULT BY 8000.
SO WE GET 9110, 6FF0 AND 8000
FOR OUR COEFFICIENT VALUES
}
        AR=PASS AX0,AX0=DM(I1,M1);
{PASS DEL ERR TO AR; DEL OUTPUT TO AX0
I1 PTG DEL ERR}
        DM(I1,M2)=MR0;
{OVERWRITE DEL ERR VALUE IN DM
I1 PTG TO DEL ERR VALUE
PASS DEL OUTPUT TO AF}
        DIS M_MODE;
{PROVIDE FOR SIGNED MULTIPLY}
        MR=MR0*MY0(SU),MY0=PM(I4,M4),AX0=DM(I1,M0);
{FIRST FILTER COMPUTATION NOW IN MR1
SET UP MULT TO MULT DEL ERR BY ITS COEFF,
ERR TO AX0
```

```
I1 POINTING TO DEL OUT VALUE
I4 POINTING TO DEL OUTPUT COEFF}
        MR=MR-AR*MY0(SU),MY0=PM(I4,M7),MX0=DM(I1,M2);
{SECOND FILTER RESULT IN MR1 REG
I4 PTG TO MOTOR SHIFT/CLAMP VALUE
LOAD DEL OUTPUT COEFF TO MY0
LOAD DEL OUTPUT VALUE TO MX0
KEEP PTR AT DEL OUTPUT VALUE}
        MR=MR+MX0*MY0(SU),MY0=PM(I4,M5);AX1=DM(I1,M2);
{FILTER OUTPUT VALUE IN MR1
MOTOR SHIFT/CLAMP VALUE TO MY0
I4 POINT AT DEADMAN TOGGLE MASK
DEL OUT VAL TO AX1}
{EXECUTE CLAMP}
OVDRV:  DM(I1,M2)=MR1,AR=PASS AX1;
{STORE OUTPUT VALUE TO MEM
PASS OLD OUTPUT TO AR}
        SE=EXP AR(HI);
{CHECK MAGNITUDE OF OLD OUTPUT VALUE}
        MR0=SE;
{PASS MAGNITUDE TO MR0}
        AR=MR1,AF=PASS MR0;
{CHECK MAGNITUDE}
        IF NE JUMP UPDAT;
{JUMP OUT IF SMALL}
        AF=PASS AX0;
{CHECK SIGN OF ERROR}
        IF GE JUMP PDCLMP;

{JUMP TO POS MOTOR CLAMP IF ERR POSITIVE}
        AR = PASS MR1;
{CHECK OUTPUT VALUE}
        IF LE JUMP UPDAT;
{OK IF ERR AND OUT ARE NEG}
        AF=PASS AX1;
{CHECK DEL OUT}
        AX1=0X807F;
{SET CLAMP VALUE}
        IF GT JUMP UPDAT;
{IF ERR NEG & OUT + AND DEL OUT + OK}
CPDAT:  DM(I1,M2)=AX1;
{EXECUTE CLAMP}
        AR=0X200;
{PREPARE TO SET BIT 9}
        DM(BALLS_FLAG)=AR;
{SET BIT 9}
        AR=DM(MAG_SPEED);
{CHECK IF SPEED IS HIGH}
        AR=PASS AR;
{EXECUTE CHECK}
```

```
                IF EQ JUMP UPDAT;
{CLEAR BALLS FLAG IF SPEED HIGH}
                JUMP OVDAT;
{JUMP OUT OF CLAMP ROUTINE}
PDCLMP: AR=PASS MR1;
{CHECK OUTPUT}
                IF GT JUMP UPDAT;
{OK IF BOTH ERR AND OUTPUT ARE +}
                AF=PASS AX1;
{CHECK DEL OUT}
                AX1=0X7F80;
{SET CLAMP VALUE}
                IF GT JUMP CPDAT;
{IF ERR + & OUT - AND D OUT + CLAMP}
UPDAT:  AR=0XFDFF;
{PREPARE TO CLEAR BALLS TO WALL FLAG}
                DM(BALLS_FLAG)=AR;
{STORE FALG}
OVDAT:  AR=DM(I1,M0);
{NEW OUTPUT VALUE TO AR
I1 POINTING DEAD TOGGLE VALUE}
STDAT:  MR=AR*MY0(SU),AX0=DM(I1,M2),AY0=PM(I4,M4);
{MOTOR DRIVE IN MR1, DEADMAN TOG MASK AY
I1 PTG DEAD TOG VAL DEAD TOG VAL AX
I4 PTG FWD DIR MASK}
                AR = AX0 XOR AY0,AY0=PM(I4,M4);
{UPDATED DEAD VAL IN AR, AY0=ENA MASK
I4 EC 3 MASK}
                DM(I1,M2)=AR,AF = PASS MR1;
{TEST MOT DR VAL SE = FLTR EXP VAL
I4 PTG FLTR SAMPLE COUNT SET}
                IF GT JUMP FWDDR;
{JUMP OVER BRAKE COMMAND IF NE}
                AR=ABS MR1,AY0=DM(I1,M2);

{SET MOT DR VAL FOR NEG DRIVE}
                MR1=AR,AR=PASS AY0;
{MOVE MOT VAL MR1, DEAD VAL AR}
FWDDR:  AF=AR OR AY0;
{ADD DIR BIT TO DEAD VAL}
                AR=MR1 OR AF;
{FULL MOT DR TO AR, AX1 = SMPL CNT SET
I4 PTG ENC INDEX MASK, SI= OUTPUT VAL
I1 PTG 1 FLTR VAL}
                DM(MDL)=AR;
{OUTPUT MOTOR DRIVE}
                JUMP VACUUM;
{CHECK FOR VACUUM ALGORITHM}
{SCLMP: AR=PASS SR0;}
{APPLY CLAMPED SPEED TO SERVO}
```

```
{       JUMP PUPDAT;}
{DO MOTOR SERVO}
STOP1:  SET FLAG_OUT;
STOP:   CALL VACUUM2;
        AR=0;
        I4=^COEFF+10;
{I4 PTG DEAD TOGG MASK}
        I1=^FILTER+10;
{I1 PTG DEL SPEED OUTPUT}
        JUMP STDAT;
{EXECUTE MOTOR STOP}
VACUUM: AR=DM(VAC_FLAG);
{GET VACUUM DEGAS CHECK FLAG}
        AR=PASS AR;
{CHECK FLAG}
        IF NE RTS;
{JUMP OUT IF FLAG IS CLEAR}
VACUUM2:I1=^VALVS+4;
{SET I1 TO RUN DEGAS PUMP}
        AX0=DM(0X384F);
{PREPARE TO SET PUMP TO CPU COMMAND}
        AR=PASS AX0;
{CHECK PUMP STATE}
        IF NE JUMP VPON;
{SET STATUS BIT IF PUMP IS TO BE TURNED ON}
{
EXECUTE TURNOFF
}
        AY0=0X7FFF;
{INJECT CONTROL MASK TO AY0}
        AR=0X2380;
{AND INSTRUCTION}
        CALL SETVLV;
{SET VALVES}
{
SET STATUS BIT TO OFF
}
        AY1=0XFFF7;
{PREPARE TO CLEAR BIT 3}
        CALL CLRSTS;

{CLEAR BIT 3}
        JUMP VACOUT;
{SET VAC FLAG AND BYE BYE}
VPON:   AY1=8;
{SET BIT 3}
        CALL SETSTS;
{SET STATUS WORD BIT 3}
{
EXECUTE TURNON
```

```
}
        AY0=0X8000;
{INJECT CONTROL MASK TO AY0}
        AR=0X23A0;
{OR INSTRUCTION}
        CALL SETVLV;
{SET VALVES}
VACOUT: AR=PASS 1;
{SET AR FOR TIMER ROUTINE}
        DM(VAC_FLAG)=AR;
{SET VACUUM DONE FLAG}
        RTS;
{JUMP OUT OF SUBROUTINE}
    .ENDMOD;
```

What is claimed is:

1. A bimodal pump system for delivering a liquid at an output port with a user-commanded constant flowrate in either a flow mode or a pressure mode, comprising:

a motor with a rotating shaft;

a cam and encoder disk attached to said shaft;

position means for determining rotational position of said cam using said encoder;

a mechanism translating rotation of said shaft to reciprocating motion;

a first pump cylinder containing a first piston head and characterized by a first pressurization number, switcheably coupleable to a source containing at least a portion of said liquid; said first piston head coupled to said mechanism;

a second pump cylinder containing a second piston head and characterized by a second pressurization number that may equal said first pressurization number, switcheably coupleable to a source containing at least a portion of said liquid; said second pump piston coupled to said mechanism;

wherein said first piston head and said second piston head are moved by said mechanism through a pump cycle having an intake stroke portion, during which said first piston head is intaking said liquid and said second piston head is exhausting said liquid, and a overlap stroke portion during which said first piston head and said second piston head are both exhausting said liquid;

means for monitoring fluid pressure at said output port;

control means including means for determining from said position means and from said monitoring means when during said pump cycle said overlap stroke occurs, and for reducing rotational speed of said motor during said overlap stroke relative to rotation speed during said intake stroke, said control means having a first input coupled to an output of said means for monitoring, a second input coupled to an output of said means for determining, and an output coupled to a drive input of said motor;

wherein in a default flow mode, a substantially constant flowrate is maintained without using real-time output pressure information.

2. The pump system of claim 1, wherein said control means further includes means for identifying which of said first pump cylinder and said second pump cylinder is operating at higher pressure.

3. The pump system of claim 2, wherein said means for identifying so identifies using said first pressurization number and said second pressurization number.

4. The pump system of claim 2, wherein said control means further includes means for determining from said positioning means whether constant displacement flow measurement time for said first or second piston head is within a desired threshold of a said user-commanded flowrate, and for changing operation of said pump system from said flow mode to said pressure mode operation if said constant displacement flow measurement time is referenced to a higher pressure operating said first or second pump cylinder.

5. The pump system of claim 1, further including means for permitting a user to command a chosen one of said flow mode and pressure mode operation of said pump system.

6. The pump system of claim 1, wherein said control means further includes means for dynamically determining and dynamically maintaining a highest stable pressure gain within said pump system.

7. The pump system of claim 6, wherein said means for dynamically determining so establishes said highest stable pressure gain each time pressure mode is entered.

8. The pump system of claim 6, wherein said means for dynamically determining decrements pressure gain within said pump system when excessive oscillation is detected during a said intake stroke portion of a said pump cycle.

9. The pump system of claim 1, wherein said control means includes means for determining start and end of said intake stroke portion, and further includes means for causing a proportioning of said liquid to occur only between start and end of said intake stroke portion;

wherein proportioning occurs during a constant flowrate.

* * * * *